US012606555B2

(12) United States Patent
Johannes et al.

(10) Patent No.: US 12,606,555 B2

(45) **Date of Patent: *Apr. 21, 2026**

(54) CHEMICAL COMPOUNDS

(71) Applicant: ASTRAZENECA AB, Sodertalje (SE)

(72) Inventors: Jeffrey Wallace Johannes, Wilmington, DE (US); Sudhir Mahadeo Hande, Wilmington, DE (US); Sebastien Louis Degorce, Wilmington, DE (US); Martin John Packer, Cambridge (GB)

(73) Assignee: ASTRAZENECA AB, Södertälje (SE)

( * ) Notice: Subject to any disclaimer, the term of this patent is extended or adjusted under 35 U.S.C. 154(b) by 992 days.

This patent is subject to a terminal disclaimer.

(21) Appl. No.: 17/715,463

(22) Filed: Apr. 7, 2022

(65) Prior Publication Data

US 2022/0227768 A1 Jul. 21, 2022

Related U.S. Application Data

(63) Continuation of application No. 16/931,792, filed on Jul. 17, 2020, now Pat. No. 11,325,906.

(60) Provisional application No. 62/876,065, filed on Jul. 19, 2019.

(51) Int. Cl.

| | |
|---|---|
| ***C07D 471/04*** | (2006.01) |
| ***A61K 31/497*** | (2006.01) |
| ***A61K 31/498*** | (2006.01) |
| ***C07D 401/12*** | (2006.01) |
| ***C07D 401/14*** | (2006.01) |
| *A61P 35/00* | (2006.01) |
| *A61P 35/02* | (2006.01) |

(52) U.S. Cl.

CPC .......... *C07D 471/04* (2013.01); *A61K 31/497* (2013.01); *A61K 31/498* (2013.01); *C07D 401/12* (2013.01); *C07D 401/14* (2013.01); *A61P 35/00* (2018.01); *A61P 35/02* (2018.01)

(58) Field of Classification Search

None

See application file for complete search history.

(56) References Cited

U.S. PATENT DOCUMENTS

| | | | | |
|---|---|---|---|---|
| 8,404,713 | B2 * | 3/2013 | Angibaud | A61P 25/00 546/159 |
| 8,541,417 | B2 | 9/2013 | Brown et al. | |
| 11,795,158 | B2 | 10/2023 | Johannes et al. | |
| 2005/0171101 | A1 | 8/2005 | Yamamoto et al. | |
| 2010/0190763 | A1 | 7/2010 | Gangloff | |
| 2010/0222348 | A1 | 9/2010 | Angibaud et al. | |
| 2012/0129868 | A1 | 5/2012 | Brown et al. | |
| 2016/0003808 | A1 | 1/2016 | Janssen et al. | |
| 2018/0162831 | A1 | 6/2018 | Kadow et al. | |
| 2018/0162834 | A1 | 6/2018 | Lee et al. | |

FOREIGN PATENT DOCUMENTS

| | | | |
|---|---|---|---|
| CN | 102341394 | A | 2/2012 |
| CN | 107849040 | A | 3/2018 |
| EP | 3312177 | A2 | 4/2018 |
| JP | 2007513087 | A | 5/2007 |
| JP | 2010532339 | A | 10/2010 |
| JP | 2011500758 | A | 1/2011 |
| JP | 2012515786 | A | 7/2012 |
| JP | 2012522007 | A | 9/2012 |
| JP | 2013500989 | A | 1/2013 |
| JP | 2018521033 | A | 8/2018 |
| WO | 2005054201 | A1 | 6/2005 |
| WO | 2005054209 | A1 | 6/2005 |
| WO | 2005054210 | A1 | 6/2005 |
| WO | 2005058843 | A1 | 6/2005 |
| WO | 2006021801 | A1 | 3/2006 |
| WO | 2008050329 | A2 | 5/2008 |
| WO | 2008076425 | A1 | 6/2008 |
| WO | 2008107478 | A1 | 9/2008 |
| WO | 2009053373 | A1 | 4/2009 |
| WO | 2009093032 | A1 | 7/2009 |
| WO | 2010085570 | A1 | 7/2010 |
| WO | 2015010135 | A2 | 1/2015 |
| WO | 2021013735 | A1 | 1/2021 |

OTHER PUBLICATIONS

Ali et al. ((2014), Input of Isosteric and Bioisosteric Approach in Drug Design, J. Chem. Soc. Pak., 36, p. 150-169) (Year: 2014).*

Patani et al. (1996) Bioisosterism A rational approach in drug design, Chem. Rev., 96, 3147-3176 (Year: 1996).*

Mohan, R., et al., ACS Omega, 2018, 3(6), pp. 6427-6438.

European Search Report for European Application No. 25151532.6, dated May 27, 2025, 9 Pages.

International Search Report and Written Opinion for International Application No. PCT/EP2020/070306, mailed Oct. 15, 2020, 10 Pages.

International Search Report and Written Opinion for International Application No. PCT/EP2021/067304, dated Oct. 16, 2019, 13 pages.

Mcmahon G., "VEGF Receptor Signaling in Tumor Angiogenisis," The Oncologist, 2000, vol. 5, Suppl 1, pp. 3-10, URL: www.The Oncologist.com, 8 pages.

(Continued)

*Primary Examiner* — Kortney L. Klinkel

*Assistant Examiner* — Dawanna Shar-Day White

(57) ABSTRACT

The present invention relates to azaquinolone compounds of Formula (I), and their use in medicine.

Formula (I)

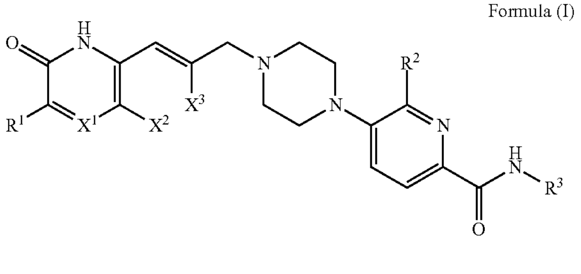

7 Claims, 1 Drawing Sheet

(56) References Cited

OTHER PUBLICATIONS

Pinedo H.M., et al., "Translation Research: The Role of VEGF in Tumor Anglogenesis," The Oncologist, 2000, vol. 5, No. 1, pp. 1-2.
Ying M., "Medicinal Chemistry, 2nd Edition", Henan Science and Technology Press, Aug. 31, 2012, 3 Pages.

* cited by examiner

FIG. 1 XRPD diffractogram for Example 4 – Form A
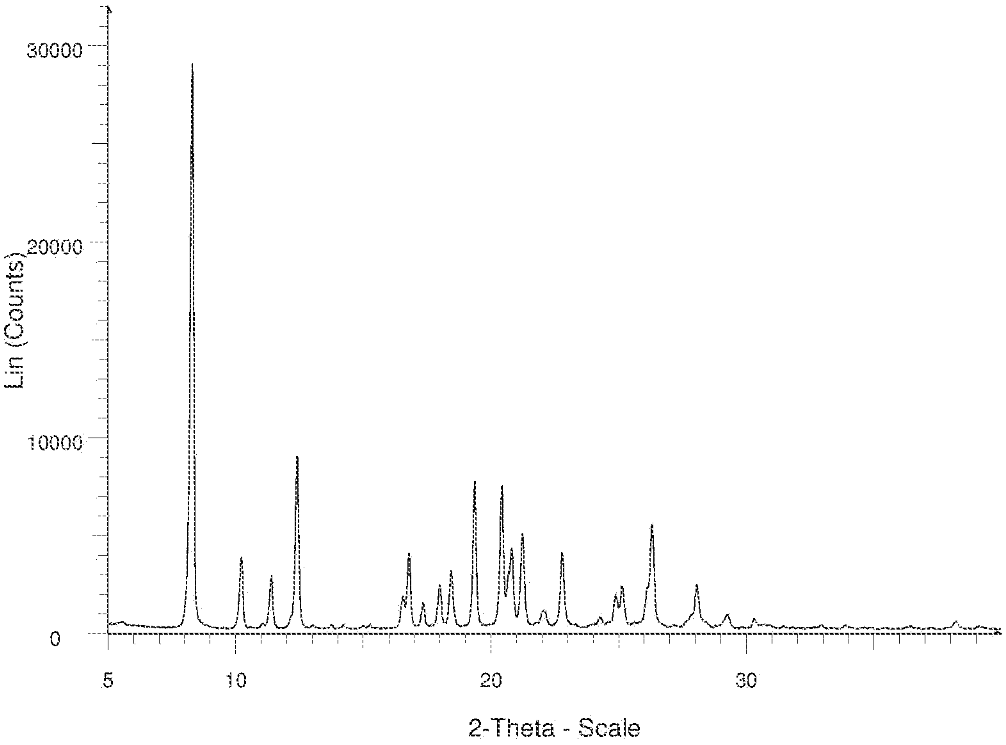
FIG. 2 DSC trace for Example 4 – Form A
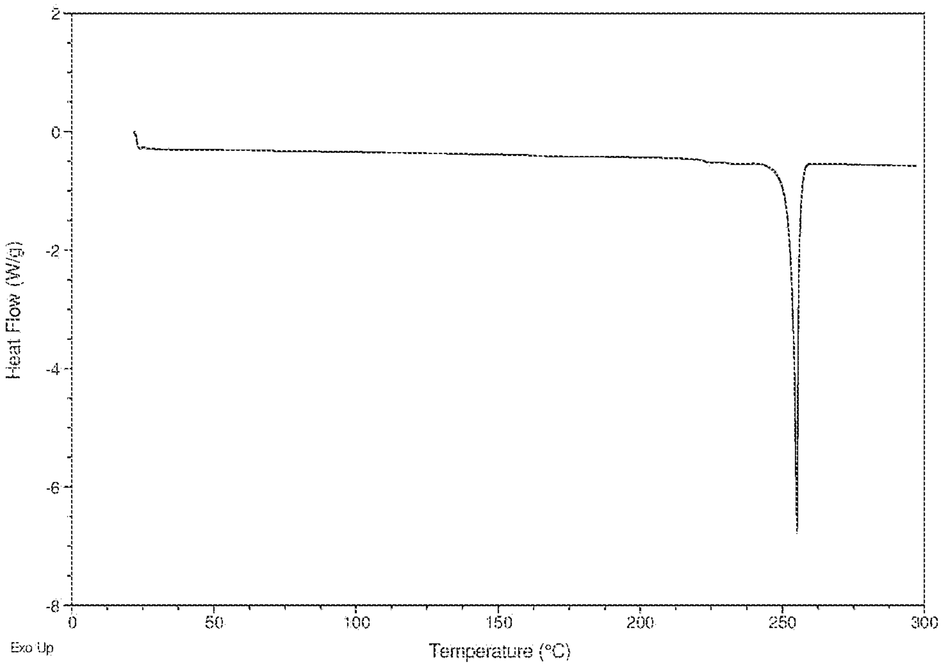

CHEMICAL COMPOUNDS

The present disclosure relates to substituted azaquinolone compounds and pharmaceutically acceptable salts thereof that inhibit the Poly (ADP-ribose) polymerase (PARP) family of enzymes. The present disclosure also relates to the use of these compounds, and pharmaceutically acceptable salts thereof, in medicine, for example in the treatment of diseases in which inhibition of PARP1 or PARP1 function is of therapeutic significance. The present disclosure also relates to methods of treatment and methods of manufacture of medicaments using compounds according to the disclosure.

PARP family of enzymes play an important role in a number of cellular processes, such as replication, recombination, chromatin remodeling, and DNA damage repair (O'Connor M J, *Mol Cell* (2015) 60(4):547-60).

Examples of PARP inhibitors and their mechanism of action are taught in e.g. WO2004/080976.

PARP1 and PARP2 are the most extensively studied PARPs for their role in DNA damage repair. PARP1 is activated by DNA damage breaks and functions to catalyse the addition of poly (ADP-ribose) (PAR) chains to target proteins. This post-translational modification, known as PARylation, mediates the recruitment of additional DNA repair factors to DNA lesions.

Following completion of this recruitment role, PARP auto-PARylation triggers the release of bound PARP from DNA to allow access to other DNA repair proteins to complete repair. Thus, the binding of PARP to damaged sites, its catalytic activity, and its eventual release from DNA are all important steps for a cancer cell to respond to DNA damage caused by chemotherapeutic agents and radiation therapy (Bai P. *Biology of poly(ADP-ribose) polymerases: the factotums of cell maintenance. Mol Cell* 2015;58:947-58.).

Inhibition of PARP family enzymes has been exploited as a strategy to selectively kill cancer cells by inactivating complementary DNA repair pathways. A number of pre-clinical and clinical studies have demonstrated that tumour cells bearing deleterious alterations of BRCA1 or BRCA2, key tumour suppressor proteins involved in double-strand DNA break (DSB) repair by homologous recombination (HR), are selectively sensitive to small molecule inhibitors of the PARP family of DNA repair enzymes. Such tumours have deficient homologous recombination repair (HRR) pathways and are dependent on PARP enzymes function for survival. Although PARP inhibitor therapy has predominantly targeted BRCA-mutated cancers, PARP inhibitors have been tested clinically in non-BRCA-mutant tumors, those which exhibit homologous recombination deficiency (HRD) (Turner N, Tuff A, Ashworth A. *Hallmarks of 'BRCAness' in sporadic cancers. Nat Rev Cancer* 2004;4: 814-9.).

It is believed that PARP inhibitors having improved selectivity for PARP1 may possess improved efficacy and reduced toxicity compared to other clinical PARP1/2 inhibitors. It is believed also that selective strong inhibition of PARP1 would lead to trapping of PARP1 on DNA, resulting in DNA double-strand breaks (DSBs) through collapse of replication forks in S-phase. It is believed also that PARP1-DNA trapping is an effective mechanism for selectively killing tumour cells having HRD.

An unmet medical need therefore exists for effective and safe PARP inhibitors. Especially PARP inhibitors having selectivity for PARP1.

The applicant has discovered that the azaquinolones described herein surprising have PARP inhibitory activity, and therefore may be useful for the treatment of diseases and conditions in which PARP function has pharmacological significance. Furthermore, azaquinolones described herein have surprisingly high selectivity for PARP1 over other PARP family members such as PARP2, PARP3, PARP5a, and PARP6. Furthermore, azaquinolones described herein have advantageously low hERG activity.

In an aspect of the invention, the applicant makes available a class of compounds of Formula (I):

(I)

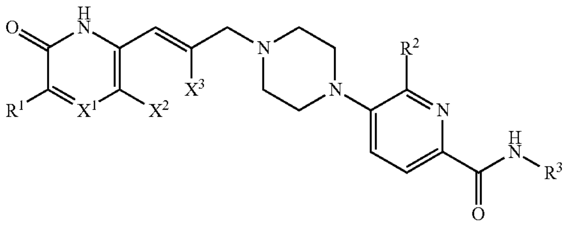

wherein:

$X^1$ and $X^2$ are each independently selected from N and C(H), $X^3$ is independently selected from N and $C(R^4)$, wherein $R^4$ is H or fluoro, $R^1$ is $C_{1-4}$ alkyl or $C_{1-4}$ fluoroalkyl, $R^2$ is independently selected from H, halo, $C_{1-4}$ alkyl, and $C_{1-4}$ fluoroalkyl, and $R^3$ is H or $C_{1-4}$ alkyl, or a pharmaceutically acceptable salt thereof provided that:

when $X^1$ is N, then $X^2$ is C(H), and $X^3$ is $C(R^4)$, when $X^2$ is N, then $X^1$=C(H), and $X^3$ is $C(R^4)$, and when $X^3$ is N, then $X^1$ and $X^2$ are both C(H).

In a further aspect, there is provided a pharmaceutical composition comprising a therapeutically effective amount of a compound of Formula I, or a pharmaceutically acceptable salt thereof, and at least one pharmaceutically acceptable diluent, excipient or inert carrier.

In a further aspect, there is provided a compound of Formula I or a pharmaceutically acceptable salt thereof, for use in treatment or prophylaxis of diseases and conditions in which inhibition of PARP1 is beneficial. In embodiments, the specification provides a compound of Formula I or a pharmaceutically acceptable salt thereof for use in the treatment of cancer. In embodiments, the cancer is breast, ovary, pancreas, prostate, hematological, gastrointestinal such as gastric and colorectal, or lung cancer. In embodiments, the cancer is breast, ovary, pancreas or prostate cancer.

In a further aspect, there is provided a method of treating diseases or conditions in which inhibition PARP1 is beneficial, comprising administering to a patient in need thereof an effective amount of a compound of Formula I or a pharmaceutically acceptable salt thereof. In an embodiment, said disease or condition is cancer. In embodiments, the cancer is breast, ovary, pancreas, prostate, hematological, gastrointestinal such as gastric and colorectal, or lung cancer. In embodiments, the cancer is breast, ovary, pancreas or prostate cancer.

In a further aspect, there is provided the compound of Formula I or a pharmaceutically acceptable salt thereof, for use in the preparation of a medicament for the treatment of diseases or conditions in which inhibition of PARP1 is beneficial. In embodiments, the cancer is breast, ovary, pancreas, prostate, hematological, gastrointestinal such as gastric and colorectal, or lung cancer. In embodiments, the cancer is breast, ovary, pancreas or prostate cancer.

In a further aspect, there is provided the use of a compound of Formula I or a pharmaceutically acceptable salt thereof, in the manufacture of a medicament for use in the treatment of diseases or conditions in which inhibition of PARP1 is beneficial. In embodiments, the cancer is breast, ovary, pancreas, prostate, hematological, gastrointestinal such as gastric and colorectal, or lung cancer. In embodiments, the cancer is breast, ovary, pancreas or prostate cancer.

In a further aspect, there is provided a compound of Formula I, or a pharmaceutically acceptable salt thereof, for use in medicine.

In a further aspect, the compound of Formula I in the free base form.

In a further aspect, there is provided a compound of Formula I or a pharmaceutically acceptable salt thereof, for use as medicament.

In a further aspect, there is provided the Examples disclosed herein.

In an aspect, there is provided a compound of Formula I which is 5-[4-[(7-ethyl-6-oxo-5H-1,5-naphthyridin-3-yl) methyl]piperazin-1-yl]-N-methyl-pyridine-2-carboxamide, or a pharmaceutically acceptable salt thereof.

In an aspect, there is provided a compound of Formula I which is 5-[4-[(7-ethyl-6-oxo-5H-1,5-naphthyridin-3-yl) methyl]piperazin-1-yl]-N-methyl-pyridine-2-carboxamide.

Further aspects of the invention will be apparent to one skilled in the art from reading this specification.

It is well known that blockade of the cardiac ion channel coded by human ether-à-gogo-related gene (hERG) is a risk factor in drug discovery and development. Blockage of hERG can cause safety problems such as cardiac arrhythmia. Advantageously, the compounds of Formula I have low hERG activity. In an embodiment, there is provided a compound of Formula I having an IC50>10 μM. In an embodiment there is provided a compound of Formula I having an IC50>20 μM.

To minimize the risks of off-target effects, it is desirable for drug molecules to possess selectivity for a specific target. The compounds of Formula I advantageously possess selectivity for PARP1 over other members of the PARP family including PARP2, PARP3, PARP5a, and PARP6. Advantageously, the compounds of Formula I possess selectivity for PARP1 over PARP2. In an embodiment, there is provided a compound of Formula I having 10-fold selectivity for PARP1 over PARP2. In an embodiment, there is provided a compound of Formula I having 100-fold selectivity for PARP1 over PARP2.

Another further aspect provides for the use of a compound of Formula I in the preparation of a medicament for use as an adjunct in cancer therapy or for potentiating tumour cells for treatment with ionizing radiation or chemotherapeutic agents, or antibody-based therapies such as immunooncology or antibody-drug conjugates.

Other further aspects provide for the treatment of disease ameliorated by the inhibition of PARP1, comprising administering to a subject in need of treatment a therapeutically effective amount of a compound of Formula I, preferably in the form of a pharmaceutical composition and the treatment of cancer, comprising administering to a subject in need of treatment a therapeutically-effective amount of a compound of Formula I in combination, preferably in the form of a pharmaceutical composition, simultaneously or sequentially with ionizing radiation or chemotherapeutic agents.

In further aspects, a compound of Formula I may be used in the preparation of a medicament for the treatment of cancer which is deficient in Homologous Recombination (HR) dependent DNA DSB repair activity, or in the treatment of a patient of a cancer which is deficient in HR dependent DNA DSB repair activity, comprising administering to said patient a therapeutically-effective amount of the compound.

The HR dependent DNA DSB repair pathway repairs double-strand breaks (DSBs) in DNA via homologous mechanisms to reform a continuous DNA helix (K. K. Khanna and S. P. Jackson, Nat. Genet. 27(3): 247-254 (2001)). The components of the HR dependent DNA DSB repair pathway include, but are not limited to, ATM (NM_000051), RAD51 (NM_002875), RAD51L1 (NM_002877), RAD51 C (NM_002876), RAD51 L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS1 (NM_002485). Other proteins involved in the HR dependent DNA DSB repair pathway include regulatory factors such as EMSY (Hughes-Davies, et al., *Cell,* 115, pp523-535). HR components are also described in Wood, et al., *Science,* 291, 1284-1289 (2001).

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterised in the art (see for example, Wood, et aL, *Science,* 291, 1284-1289 (2001)) and include the components listed above.

In some embodiments, the cancer cells may have a BRCA1 and/or a BRCA2 deficient phenotype i.e. BRCA1 and/or BRCA2 activity is reduced or abolished in the cancer cells. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (Hughes-Davies, et al., *Cell,* 115, 523-535).

BRCA1 and BRCA2 are known tumour suppressors whose wild-type alleles are frequently lost in tumours of heterozygous carriers (Jasin M., *Oncogene,* 21(58), 8981-93 (2002); Tutt, et al., *Trends Mol Med.,* 8 (12), 571-6, (2002)). The association of BRCA1 and/or BRCA2 mutations with breast cancer is well-characterised in the art (Radice, P. J., *Exp Clin Cancer Res.,* 21(3 Suppl), 9-12 (2002)). Amplification of the EMSY gene, which encodes a BRCA2 binding factor, is also known to be associated with breast and ovarian cancer. Carriers of mutations in BRCA1 and/or BRCA2 are also at elevated risk of certain cancers, including breast, ovary, pancreas, prostate, hematological, gastrointestinal and lung cancer.

In some embodiments, the individual is heterozygous for one or more variations, such as mutations and polymorphisms, in BRCA1 and/or BRCA2 or a regulator thereof. The detection of variation in BRCA1 and BRCA2 is well-known in the art and is described, for example in EP 699 754, EP 705 903, Neuhausen, S. L. and Ostrander, E. A., Genet. Test, 1, 75-83 (1992); Chappnis, P. O. and Foulkes, W. O., *Cancer Treat Res,* 107, 29-59 (2002); Janatova M., et al., *Neoplasma,* 50(4), 246-505 (2003); Jancarkova, N.,*Ceska Gynekol.,* 68{1), 11-6 (2003)}. Determination of amplification of the BRCA2 binding factor EMSY is described in Hughes-Davies, et al., *Cell,* 115, 523-535).

Mutations and polymorphisms associated with cancer may be detected at the nucleic acid level by detecting the presence of a variant nucleic acid sequence or at the protein level by detecting the presence of a variant (i.e. a mutant or allelic variant) polypeptide.

Definitions

Alkyl groups and moieties are straight or branched chain, e.g. $C_{1-8}$ alkyl, $C_{1-6}$ alkyl, $C_{1-4}$ alkyl or $C_{5-6}$ alkyl. Examples of alkyl groups are methyl, ethyl, n-propyl, iso-propyl, n-butyl, t-butyl, n-pentyl, n-hexyl, n-heptyl and n-octyl, such as methyl or n-hexyl.

Fluoroalkyl groups are alkyl groups in which one or more H atoms is replaced with one or more fluoro atoms, e.g. $C_{1-8}$ fluoroalkyl, $C_{1-6}$ fluoroalkyl, $C_{1-4}$ fluoroalkyl or $C_5$-6 fluoroalkyl. Examples include fluoromethyl ($CH_2F$—), difluromethyl ($CHF_2$—), trifluoromethyl ($CF_3$—), 2,2,2-trifluoroethyl ($CF_3CH_2$—), 1,1-difluoroethyl ($CH_3CHF_2$—), 2,2-difluoroethyl ($CHF_2CH_2$—), and 2-fluoroethyl ($CH_2FCH_2$—).

Halo means fluoro, chloro, bromo, and iodo. In an embodiment, halo is fluoro or chloro.

In this specification, unless otherwise stated, the term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In this specification, unless otherwise stated, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

The compounds of Formula I may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglu mine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Non-toxic physiologically-acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

The compounds of Formula I may have more than one chiral center, and it is to be understood that the application encompasses all individual stereoisomers, enantiomers and diastereoisomers and mixtures thereof. Thus, it is to be understood that, insofar as the compounds of Formula I can exist in optically active or racemic forms by virtue of one or more asymmetric carbon atoms, the application includes in its definition any such optically active or racemic form which possesses the above-mentioned activity. The present application encompasses all such stereoisomers having activity as herein defined.

Thus, throughout the specification, where reference is made to the compound of Formula I it is to be understood that the term compound includes diastereoisomers, mixtures of diastereoisomers, and enantiomers that are PARP1 inhibitors.

It is also to be understood that certain compounds of Formula I, and pharmaceutically salts thereof, can exist in solvated as well as unsolvated forms such as, for example, hydrated and anhydrous forms. It is to be understood that the compounds herein encompass all such solvated forms. For the sake of clarity, this includes both solvated (e.g., hydrated) forms of the free form of the compound, as well as solvated (e.g., hydrated) forms of the salt of the compound.

Formula I as described herein is intended to encompass all isotopes of its constituent atoms. For example, H (or hydrogen) includes any isotopic form of hydrogen including $^{1}H$, $^{2}H$ (D), and $^{3}H$ (T); C includes any isotopic form of carbon including $^{12}C$, $^{13}C$, and $^{14}C$; O includes any isotopic form of oxygen including $^{16}O$, $^{17}O$ and $^{18}O$; N includes any isotopic form of nitrogen including $13_N$, $14_N$ and $15_N$; F includes any isotopic form of fluorine including $^{19}F$ and $^{18}F$; and the like. In one aspect, the compounds of Formula I include isotopes of the atoms covered therein in amounts corresponding to their naturally occurring abundance. However, in certain instances, it may be desirable to enrich one or more atom in a particular isotope which would normally be present in a lower abundance. For example, $^{1}H$ would normally be present in greater than 99.98% abundance; however, in one aspect, a compound of any formula presented herein may be enriched in $^2H$ or $^3H$ at one or more positions where H is present. In another aspect, when a compound of any formula presented herein is enriched in a radioactive isotope, for example $^3H$ and $^{14}C$, the compound may be useful in drug and/or substrate tissue distribution assays. It is to be understood that the present application encompasses all such isotopic forms.

The compounds of Formula I, or pharmaceutically acceptable salts thereof, will normally be administered via the oral route in the form of pharmaceutical preparations comprising the active ingredient or a pharmaceutically acceptable salt or solvate thereof, or a solvate of such a salt, in a pharmaceutically acceptable dosage form. Depending upon the disorder and patient to be treated, the compositions may be administered at varying doses.

The pharmaceutical formulations of the compound of Formula I described above may be prepared for oral administration, particularly in the form of tablets or capsules, and especially involving technologies aimed at furnishing colon-targeted drug release (Patel, M. M. Expert Opin. Drug Deliv. 2011, 8 (10), 1247-1258).

The pharmaceutical formulations of the compound of Formula I described above may conveniently be administered in unit dosage form and may be prepared by any of the methods well-known in the pharmaceutical art, for example as described in Remington's Pharmaceutical Sciences, 17th ed., Mack Publishing Company, Easton, PA, (1985).

Pharmaceutical formulations suitable for oral administration may comprise one or more physiologically compatible carriers and/or excipients and may be in solid or liquid form. Tablets and capsules may be prepared with binding agents, fillers, lubricants and/or surfactants, such as sodium lauryl sulfate. Liquid compositions may contain conventional additives such as suspending agents, emulsifying agents and/or preservatives. Liquid compositions may be encapsulated in, for example, gelatin to provide a unit dosage form. Solid oral dosage forms include tablets, two-piece hard shell capsules and soft elastic gelatin (SEG) capsules. Such two-piece hard shell capsules may be made for example by filling a compound of Formula (I) into a gelatin or hydroxypropyl methylcellulose (HPMC) shell.

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitable daily doses of the compounds of Formula I, or a pharmaceutically acceptable salt thereof, in therapeutic treatment of humans are about 0.0001-100 mg/kg body weight.

Oral formulations are preferred, particularly tablets or capsules which may be formulated by methods known to those skilled in the art to provide doses of the active compound in the range of 0.1 mg to 1000 mg.

BRIEF DESCRIPTION OF THE FIGURES

FIG. 1 shows an X-ray powder diffraction of Example 4 Form A

FIG. 2 shows a DSC trace of Example 4 Form A

EXAMPLES

The compounds of the application will now be further explained by reference to the following non-limiting examples.

General Experimental Conditions $^1H$ NMR spectra were obtained using a Bruker 300 MHz, 400 MHz or 500 MHz spectrometer at 27° C. unless otherwise noted; chemical shifts are expressed in parts per million (ppm, δ units) and are referenced to the residual mono-$^1H$ isotopologue of the solvent ($CHCl_3$: 7.24 ppm; $CHDCl_2$: 5.32 ppm; $CD_3S(=O)CD_2H$: 2.49 ppm). Coupling constants are given in units of hertz (Hz). Splitting patterns describe apparent multiplicities and are designated as s (singlet), d (doublet), t (triplet), q (quartet), m (multiplet) and br s (broad singlet). LC-MS was carried out using a Waters UPLC fitted with a Waters SQD mass spectrometer or Shimadzu LC-20AD LC-20XR LC-30AD with a Shimadzu 2020 mass spectrometer. Reported molecular ions correspond to [M+H]+ unless otherwise noted; for molecules with multiple isotopic patterns (Br, Cl, etc.) the reported value is the one obtained for the lowest isotope mass unless otherwise specified.

Flash chromatography was performed using straight phase flash chromatography on a SP1™ Purification system from Biotage™, CombiFlash®Rf from ISCO or on Gilson system from Thermo Fisher using normal phase silica $FLASH_+$™ (40 M, 25 M or 12 M) or SNAP™ KP-Sil Cartridges (340, 100, 50 or 10), Flash Column silica-CS columns from Agela, with C18-flash columns or standard flash chromatography. In general, all solvents used were commercially available and of analytical grade. Anhydrous solvents were routinely used for reactions. Phase Separators used in the examples are ISOLUTE® Phase Separator columns. The intermediates and examples named below were named using ACD/Name 12.01 from Advanced Chemistry Development, Inc. (ACD/Labs). The starting materials were obtained from commercial sources or made via literature routes.

X-Ray Powder Diffraction (XRPD) Analysis

XRPD analysis was performed using a Bruker D8 diffractometer, which is commercially available from Bruker AXS Inc™ (Madison, Wisconsin). The XRPD spectra were obtained by mounting a sample (approximately 10 mg) of the material for analysis on a single silicon crystal wafer mount (e.g., a Bruker silicon zero background X-ray diffraction sample holder) and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms (i.e., about 1.54 angstroms). The sample was exposed for 1 second per 0.02 degree 2-theta increment (continuous scan mode) over the range 5 degrees to 40 degrees 2-theta in theta-theta mode. The running time was ~15 min for D8.

XRPD 2θ values may vary with a reasonable range, e.g., in the range ±0.2° and that XRPD intensities may vary when measured for essentially the same crystalline form for a variety of reasons including, for example, preferred orientation. Principles of XRPD are described in publications, such as, for example, Giacovazzo, C. et al. (1995), Fundamentals of Crystallography, Oxford University Press; Jenkins, R. and Snyder, R. L. (1996), Introduction to X-Ray Powder Diffractometry, John Wiley & Sons, New York; and Klug, H. P. & Alexander, L. E. (1974), X-ray Diffraction Procedures, John Wiley and Sons, New York.

DSC Analysis

DSC analysis was performed on samples prepared according to standard methods using a Q SERIES™ Q1000 DSC calorimeter available from TA INSTRUMENTS® (New Castle, Del.). A sample (approximately 2 mg) was weighed into an aluminum sample pan and transferred to the DSC. The instrument was purged with nitrogen at 50 mL/min and data collected between 22° C. and 300° C., using a dynamic heating rate of 10° C/minute. Thermal data was analyzed using standard software, e.g., Universal v.4.5A from TA INSTRUMENTS®.

The following abbreviations are used: AcOH=acetic acid; aq=aqueous; BAST=Bis(2-methoxyethyl)aminosulfur Trifluoride ; $Boc_2O$=di-tert-butyl decarbonate; Boc=t-butyloxycarbonyl; $CDCl_3$=deuterated chloroform; $CD_3OD$=deuterated methanol; $CH_3NO_2$=nitromethane; DCE=1,2-dichloroethane; DCM=dichloromethane; DEA=diethylamine; DEAD=diethyl azodicarboxylate; Dess-martin periodinane=1,1,1 -Tris(acetyloxy)-1,1 -dihydro-1,2-benziodoxol-3-(1 H)-one; DIPEA=N,N-diisopropylethylamine; DMAP=2,6-dimethylaminopyridine; DMF=N,N-dimethylformamide; DMSO=dimethylsulfoxide; DMSO-$d_6$=deuterated dimethylsulfoxide; DPPA=diphenyl phosphorazidate; dppf=1,1'-bis(diphenylphosphino)ferrocene; DIAD=Di-isopropyl (E)-diazene-1,2-dicarboxylate; DSC=differential scanning calorimetry; DTAD=Di-tert-butyl (E)-diazene-1,2-dicarboxylate; ee=enantiomeric excess; eq.=equivalent; ESI=electrospray ionization; $Et_2O$=diethyl ether; EtOAc or EA=ethylacetate; EtOH=ethanol; FA=formic acid; Grubbs catalyst (1,3-Dimesitylimidazolin-2-ylidene)(tricyclohexylphosphine)ruthenium dichloride; h=hour(s); HATU=(dimethylamino)-NN-dimethyl(3-oxido-1 H-[1,2,3]triazolo[4,5-b]pyridinyl)methaniminium hexafluorophosphate; HCl=hydrochloric acid; $H_2O_2$=hydrogen peroxide; HP=high pressure; IPA=isopropylalcohol; LC=liquid chromatography; $LiClO_4$=lithium perchlorate; mmol=millimole; mCPBA=meta-chloroperoxybenzoic acid; MeOH=methanol; min=minute(s); MeCN or CH3CN=acetonitrile; $MeNO_2$=nitromethane; MS=mass=spectrometery; NMP=N-methyl-2-pyrrolidone; NMR=nuclear magnetic resonance; Pd/C=Palladium on carbon; $Pd_2dba_3$=Tris(dibenzylideneacetone)dipalladium (0); $PdCl_2$(dppf)=1,1'-bis(di-tert-butylphosphino)ferrocene palladium dichloride; PE=Petroleum ether; $PPh_3$=Triphenylphosphine; rt=room temperature; Rt or RT=retention time; Ruphos Pd G3=(2-Dicyclohexylphosphino-2',6'-diisopropoxy-1,1'-biphenyl)[2-(2'-amino-1,1'biphenyl)]palladium(II) methanesulfonate; sat=saturated; SFC=supercritical fluid chromatography; T3P=2,4,6-tripropyl-1,3,5,2,4,6-trioxatriphosphinane 2,4,6-trioxide; TBTU=2-(1H-benzo[d][1,2,3]triazol-1-yl)-1,1,3,3-tetramethylisouronium tetrafluoroborate; TFA=trifluoroacetic acid; THF=tetrahydrofuran; TLC=thin layer chromatography; TMS=trimethylsilyl; Xantphos=4,5-bis(diphenylphosphino)-9,9-dimethylxanthene; CBr4=Carbon tetrabromide; HCl=Hydrochloric acid; HBr=Hydrobromic acid;

Cs2CO3=Cesium carbonate; MgSO4=Magnesium sulfate; NaHCO3=Sodium bicarbonate; DDQ=2,3-Dichloro-5,6-dicyano-1,4-benzoquinone; SOCI2=Thionyl chloride; DIBAL-H=Diisobutylaluminium hydride; NH4HCO3=Ammonium bicarbonate; BINAP=2,2'-bis(diphenylphosphino)-1,1'-binaphthyl.

Synthesis of Starting Materials and Intermediates

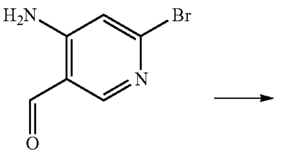

Intermediate 1

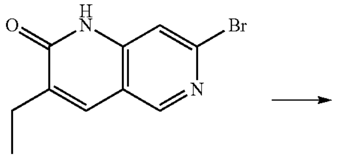

Intermediate 2

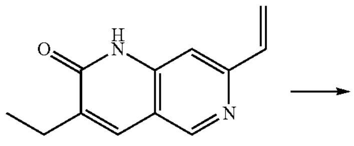

Intermediate 3

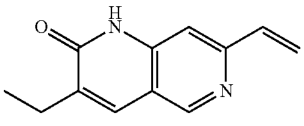

Intermediate 4

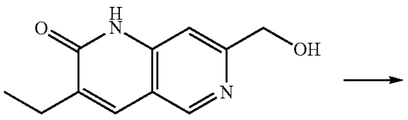

Intermediate 5

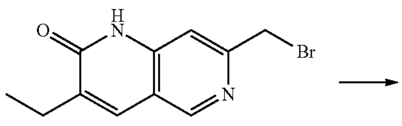

Intermediate 6

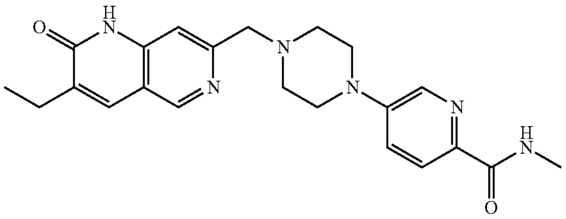 [SMILES: CCc1cc2cnc(CN3CCN(c4ccc(C(=O)NC)nc4)CC3)cc2[nH]c1=O]

Example 1

Intermediate 2:
7-bromo-3-ethyl-1H-1,6-naohthyridin-2-one

Butyryl chloride (0.143 mL, 1.37 mmol) was added dropwise to a stirred solution of 4-amino-6-bromo-pyridine-3-carbaldehyde (Intermediate 1 250 mg, 1.24 mmol), DIPEA (1.086 mL, 6.22 mmol) and DMAP (30.4 mg, 0.25 mmol) in $CH_2Cl_2$ (5 mL) at 0° C. The resulting solution was stirred rt for 4 h. More 2 eq of butyryl chloride was added and reaction was continued for another 24 h. Reaction was diluted with water and extracted with ethyl acetate. Organic layer was dried over sodium sulphate and concentrated to give crude product. 1.5 mL MeOH was added and the solid (product) was filter off, washed with 1 mL MeOH to give 7-bromo-3-ethyl-1H-1,6-naphthyridin-2-one (Intermediate 2, 167 mg, 53.1%) as a white solid.

1H NMR (DMSO-d6) 1.17 (3H, t), 2.45-2.50 (2H, m, overlapped with solvent DMSO peak), 7.35 (1 H, s), 7.82 (1H, s), 8.63 (1H, s), 12.09 (1H, br s) ; m/z ($ES^+$) $[M+H]^+$ =252

Intermediate 3:
3-ethyl-7-vinyl-1H-1,6-naohthyridin-2-one $PdCl_2$(dppf) (37.6 mg, 0.05 mmol) was added to a stirred mixture of 7-bromo-3-ethyl-1H-1,6-naphthyridin-2-one (Intermediate 2, 130 mg, 0.51 mmol), 4,4,5,5-tetramethyl-2-vinyl-1,3,2-dioxaborolane (0.105 mL, 0.62 mmol) and $K_2CO_3$ (213 mg, 1.54 mmol) in 1,4-dioxane (4 mL)/ water (1.333 mL) and the resulting mixture was stirred at 90° C. for 1 h. The reaction mixture was diluted with water and extracted with ethyl acetate. The organic layers were combined, dried over sodium sulphate and concentrated to give crude product. The resulting residue was purified by flash silica chromatography, elution gradient 0 to 20% MeOH in DCM. Product fractions were concentrated under reduced pressure to dryness to afford 3-ethyl-7-vinyl-1H-1,6-naphthyridin-2-one (Intermediate 3, 93 mg, 90%) as a yellow solid.

1H NMR (DMSO-d6) 1.18 (3H, t), 2.53 (2H, m, overlapped with solvent DMSO peak), 5.49 (1H, dd), 6.27 (1H, dd), 6.84 (1H, dd), 7.15 (1H, s), 7.81 (1H, s), 8.78 (1H, s), 12.00 (1H, br s) ; m/z ($ES^+$) $[M+H]^+$=201

Intermediate 4:
3-ethyl-2-oxo-1H-1,6-naohthyridine-7-carbaldehyde

Osmium tetroxide in $H_2O$ (0.024 mL, 3.00 μmol) was added to a solution of 3-ethyl-7-vinyl-1H-1,6-naphthyridin-2-one (Intermediate 3, 30 mg, 0.15 mmol), 2,6-lutidine (0.035 mL, 0.30 mmol) and sodium periodate (128 mg, 0.60 mmol) in THF (1 mL)/water (0.200 mL) and stirred at rt for overnight. Reaction was diluted with water and extracted with ethyl acetate and the filtrate was concentrated to dryness. The resulting residue was purified by flash silica chromatography, elution gradient 0 to 15% MeOH in DCM. Product fractions were concentrated under reduced pressure to afford 3-ethyl-2-oxo-1H-1,6-naphthyridine-7-carbaldehyde (Intermediate 4, 24.00 mg, 79%) as a light-yellow foam.

1H NMR (DMSO-d6) 1.20 (3H, t), 2.55-2.62 (2H, m, overlapped with solvent DMSO peak), 7.73 (1H, s), 7.95 (1H, s), 9.03 (1H, s), 10.00 (1H, s), 12.32 (1H, br s); m/z ($ES^+$) $[M+H]^+$=203

Intermediate 5: 3-ethyl-7-(hydroxymethyl)-1H-1,6-naohthyridin-2-one

Sodium borohydride (61.4 mg, 1.62 mmol) was added slowly to a stirred solution of 3-ethyl-2-oxo-1 H-1,6-naphthyridine-7-carbaldehyde (Intermediate 4, 82 mg, 0.41 mmol) in methanol (2 mL) at 0° C. and the resulting mixture was stirred at room temperature for 1 h. Methanol was removed under vacuum and the resulting residue was purified by flash silica chromatography, elution gradient 0 to 35% MeOH in DCM. Product fractions were concentrated under reduced pressure to afford 3-ethyl-7-(hydroxymethyl)-1H-1,6-naphthyridin-2-one (Intermediate 5, 68.0 mg, 82%) as a pale-yellow solid.

1H NMR (500 MHz, DMSO-d6) 1.18 (3H, t), 2.52-2.55 (2H, m, overlapped with solvent DMSO peak), 4.59 (2H, br s), 5.52 (1H, br s), 7.33 (1H, s), 7.80 (1H, s), 8.71 (1H, s), 12.01 (1H, br s) ; m/z ($ES^+$) $[M+H]^+$=205

Intermediate 6: 7-(bromomethyl)-3-ethyl-1 H-1 ,6-naphthyridin-2-one

CBr4 (928 mg, 2.80 mmol) was added to a stirred solution of 3-ethyl-7-(hydroxymethyl)-1H-1,6-naphthyridin-2-one (Intermediate 5, 381 mg, 1.87 mmol) and triphenylphosphine (734 mg, 2.80 mmol) in CH2Cl2 (18.656 ml) at 0° C. and the resulting solution was stirred at 0° C. for 2 hours. Reaction was concentrated, and the resulting residue was purified by flash silica chromatography, elution gradient 0 to 15% MeOH in DCM. Product fractions were concentrated under reduced pressure to afford 7-(bromomethyl)-3-ethyl-1H-1,6-naphthyridin-2-one (Intermediate 6, 386 mg, 77%) as a white solid (Contains triphenyl phosphine oxide, difficult to separate). This compound was subjected to the next step without further purification.

$m/z(ES^+)[M]^+$=267

Example 1: 5-[4-[(3-ethyl-2-oxo-1H-1,6-naphthyridin-7-yl)methyl]piperazin-1-yl]-N-methyl-pyridine-2-carboxamide

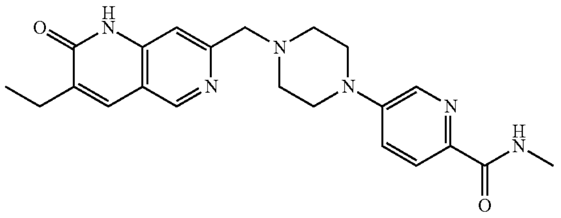

DIPEA (0.059 mL, 0.34 mmol) was added to a stirred solution of 7-(bromomethyl)-3-ethyl-1H-1,6-naphthyridin-2-one (Intermediate 6, 30 mg, 0.11 mmol) and N-methyl-5-piperazin-1-yl-pyridine-2-carboxamide, 2 HCl (Intermediate 13, 42.8 mg, 0.15 mmol) in acetonitrile (1 mL) at 20° C. The resulting solution was stirred at 70° C. for 2 hours. Solvent was removed under vacuum and the resulting crude material was further purified by reverse phase chromatography (RediSep Rf Gold® C18, 0 to 90% acetonitrile in water, 0.1% NH4OH as an additive). Product fractions were concentrated under reduced pressure to dryness to afford 5-[4-[(3-ethyl-2-oxo-1H-1,6-naphthyridin-7-yl)methyl]piperazin-1-yl]-N-methyl-pyridine-2-carboxamide (Example 1, 23.60 mg, 51.7%) as a pale-yellow solid.

1H NMR (500 MHz, DMSO-d6) 1.18 (3H, br t), 2.54 (2H, m, overlapped with solvent DMSO peak), 2.67 (4H, br s), 2.79 (3H, br d), 3.38 (4H, br s), 3.75 (2H, br s), 7.34 (1H, s), 7.42 (1H, br dd), 7.77-7.88 (2H, m), 8.29 (1H, br d), 8.40 (1H, br d), 8.75 (1H, s), 11.60 - 12.11 (1H, m); m/z (ES$^+$) $[M+H]^+$=407

Example 2: 5-[4-[(3-ethyl-2-oxo-1H-1,6-naphthyridin-7-yl)methyl]piperazin-1-yl]-6-fluoro-N-methyl-pyridine-2-carboxamide

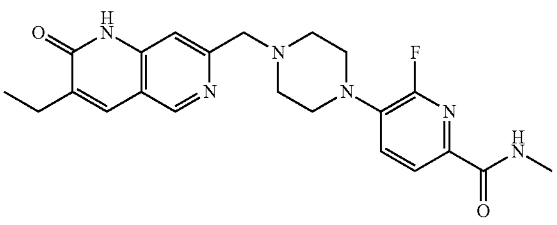 [SMILES: CCc1cc2cnc(CN3CCN(c4ccc(C(=O)NC)nc4F)CC3)cc2[nH]c1=O]

DIPEA (0.082 mL, 0.47 mmol) was added to a stirred solution of 7-(bromomethyl)-3-ethyl-1H-1,6-naphthyridin-2-one (Intermediate 6, 25 mg, 0.09 mmol) and 6-fluoro-N-methyl-5-piperazin-1-yl-pyridine-2-carboxamide, HCl (Intermediate 23, 28.3 mg, 0.10 mmol) in acetonitrile (2 mL) at 20° C. The resulting solution was stirred at 70° C. for 2 hours. Solvent was removed under vacuum. The resulting residue was purified by flash silica chromatography, elution gradient 0 to 20% MeOH in DCM. Product fractions were concentrated under reduced pressure to afford 5-[4-[(3-ethyl-2-oxo-1H-1,6-naphthyridin-7-yl)methyl]piperazin-1-yl]-6-fluoro-N-methyl-pyridine-2-carboxamide (Example 2, 17.00 mg, 42.8%) as a pale yellow solid.

1H NMR (500 MHz, DMSO-d6) 1.18 (3H, t), 2.52-2.55 (2H, m, overlapped with solvent DMSO peak), 2.64 (4H, br s), 2.77 (3H, d), 3.20 (4H, br s), 3.70 (2H, s), 7.32 (1H, s), 7.59 (1H, dd), 7.80 (1H, s), 7.86 (1H, d), 8.31-8.49 (1H, m), 8.73 (1H, s), 11.93 (1H, br s); m/z (ES$^+$) $[M+H]^+$=425

Example 3: 6-chloro-5-[4-[(3-ethyl-2-oxo-1H-1,6-naphthyridin-7-yl)methyl]piperazin-1-yl]-N-methyl-pyridine-2-carboxamide

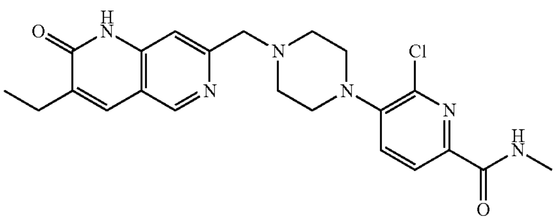 [SMILES: CCc1cc2cnc(CN3CCN(c4ccc(C(=O)NC)nc4Cl)CC3)cc2[nH]c1=O]

DIPEA (0.082 mL, 0.47 mmol) was added to a stirred solution of 7-(bromomethyl)-3-ethyl-1H-1,6-naphthyridin-2-one (Intermediate 6, 25 mg, 0.09 mmol) and 6-chloro-N-methyl-5-piperazin-1-yl-pyridine-2-carboxamide, 2 HCl (Intermediate 47, 33.7 mg, 0.10 mmol) in acetonitrile (2 mL) at 20° C. and the resulting solution was stirred at 70° C. for 2 hours. Solvent was removed under vacuum. The resulting residue was purified by flash silica chromatography, elution gradient 0 to 20% MeOH in DCM. Product fractions were concentrated under reduced pressure to afford 6-chloro-5-[4-[(3-ethyl-2-oxo-1H-1,6-naphthyridin-7-yl)methyl]piperazin-1-yl]-N-methyl-pyridine-2-carboxamide (Example 3, 19.20 mg, 46.5%) as a white solid.

1H NMR (500 MHz, DMSO-d6) 1.18 (3H, t), 2.53 (2H, m, overlapped with solvent DMSO peak), 2.66 (4H, br s), 2.80 (3H, d), 3.15 (4H, br s), 3.72 (2H, s), 7.33 (1H, s), 7.68 (1H, d), 7.81 (1H, s), 7.95 (1H, d), 8.43 (1H, br d), 8.74 (1H, s), 11.93 (1H, s); m/z (ES$^+$) $[M+H]^+$=441.

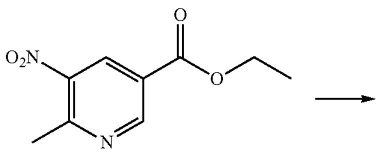

Intermediate 7

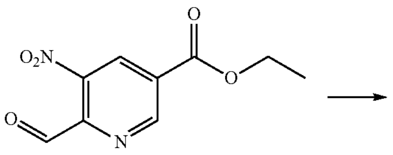

Intermediate 8

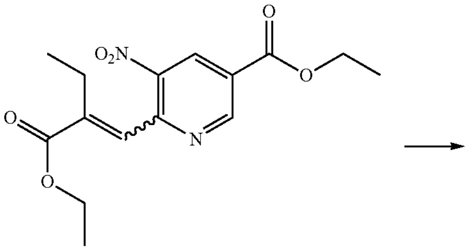

Intermediate 9

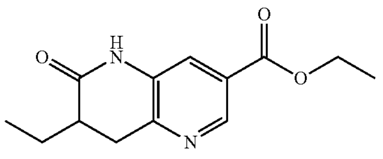

Intermediate 10

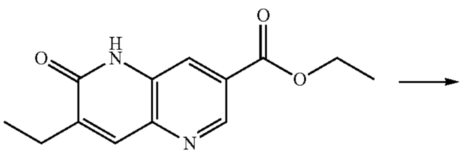

Intermediate 11

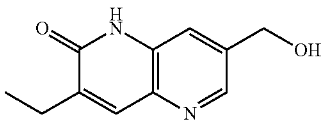

Intermediate 12

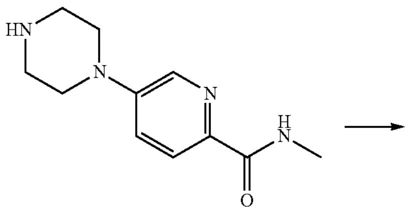

Intermediate 13

-continued

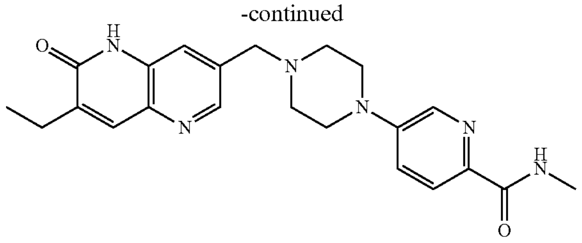

Example 4

Intermediate 8: Ethyl 6-formyl-5-nitro-pyridine-3-carboxylate

A mixture of ethyl 6-methyl-5-nitro-pyridine-3-carboxylate (Intermediate 7, 10 g, 47.58 mmol) and selenium dioxide (7.92 g, 71.36 mmol) in 1,4-dioxane (50 mL) was stirred at 110° C. for 20 h. The reaction mixture was cooled to room temperature, filtered through a pad of celite and the celite was washed with ethyl acetate. The combined filtrate was concentrated, and the resulting residue was purified by flash silica chromatography, elution gradient 0 to 70% ethyl acetate in hexanes. Product fractions were concentrated under reduced pressure to afford ethyl 6-formyl-5-nitro-pyridine-3-carboxylate (Intermediate 8, 9.70 g, 91%) as a brown oil. 1H NMR (500 MHz, CHLOROFORM-d) 1.48 (3H, t), 4.54 (2H, q), 8.81 (1H, d), 9.51 (1H, d), 10.32 (1H, s); m/z ($ES^+$) $[M]^+$=224.

Intermediate 9: Ethyl 6-[(E)-2-ethoxycarbonylbut-1-enyl]-5-nitro-pyridine-3-carboxylate (mixture of E/Z isomers)

To a stirred solution of sodium hydride (9.63 g, 240.89 mmol) (60% in mineral oil) in anhydrous THF (100 mL) was added ethyl 2-(diethoxyphosphoryl)butanoate (60.8 g, 240.89 mmol) dropwise with an addition funnel at 0° C. to give a grey colored mixture. The resulting mixture was stirred at 0° C. for 10 min and warmed to room temperature over 10 minutes and stirred at 40° C. for 5 minutes. The reaction mixture was cooled to −78° C. and to this cooled reaction mixture was then slowly added solution of ethyl 6-formyl-5-nitro-pyridine-3-carboxylate (Intermediate 8, 22.5 g, 100.37 mmol) in 100 ml THF. The mixture was quenched with sat.$NH_4Cl$ solution, extracted with ethyl acetate. The combined the organic layers were dried over sodium $Na_2SO_4$, filtered and concentrated to give crude product. the resulting residue was purified by flash silica chromatography, elution gradient 0 to 50% ethyl acetate in hexanes. Product fractions were concentrated under reduced pressure to afford ethyl 6-[(E)-2-ethoxycarbonylbut-1-enyl]-5-nitro-pyridine-3-carboxylate (Intermediate 9, 24.30 g, 75%) as a yellow oil (1:1 and mixture of E/Z isomer). 1H NMR (500 MHz, CHLOROFORM-d) 1.13 (3H, t), 1.18 (3H, t), 1.23 (3H, t), 1.37 (3H, t), 1.45 (6H, q), 2.57 (2H, qd), 2.66 (2H, q), 4.11-4.24 (2H, m), 4.32 (2H, q), 4.45-4.56 (4H, m), 7.08 (1 H, s), 7.85 (1 H, s), 8.86 (2H, dd), 9.26 (1 H, d), 9.43 (1 H, d); m/z ($ES^+$) $[M]^+$=322

Intermediate 10: ethyl 7-ethyl-6-oxo-7,8-dihydro-5H-1,5-naohthyridine-3-carboxylate A mixture of ethyl 6-[(E)-2-ethoxycarbonylbut-1-enyl]-5-nitro-pyridine-3-carboxylate (1:1 mixture of E/Z isomers) (Intermediate 9, 3.75 g, 11.63 mmol), Pd/C (1.857 g, 1.75 mmol) (10%) in ethanol (30 mL) was degassed, filled up with H2 (balloon), and the reaction was stirred at room temperature for overnight under H2 atmosphere. The mixture was filtered through a celite bed and the celite bed washed with ethanol. After concentration, 4 M HCl in dioxanes (15 ml) was added to the resulting residue and the mixture was stirred at room temperature for 30 min. The mixture was diluted with ether and the solid was filtered off, washed with diethyl ether and dried under vacuum to afford ethyl 7-ethyl-6-oxo-7,8-dihydro-5H-1,5-naphthyridine-3-carboxylate (Intermediate 10, 2.260 g, 78%) as a white solid. 1H NMR (500 MHz, DMSO-d6) 0.94 (3H, t), 1.33 (3H, t), 1.41-1.51 (1H, m), 1.69-1.81 (1H, m), 2.41-2.48 (1H, m), 2.94 (1H, dd), 3.20 (1H, dd), 4.35 (2H, t), 7.67 (1H, d), 8.61 (1H, d), 10.32 (1H, s); m/z ($ES^+$) $[M+H]^+$=249.

Intermediate 11: Ethyl 7-ethyl-6-oxo-5H-1,5-naphthyridine-3-carboxylate

Ethyl 7-ethyl-6-oxo-7,8-dihydro-5H-1,5-naphthyridine-3-carboxylate (Intermediate 10, 2.26 g, 9.10 mmol) was dissolve into 1,4-dioxane (40 mL), DDQ (2.273 g, 10.01 mmol) was added and the mixture was stirred at reflux for 3 h. Solvent was removed under reduced pressure, sat. $NaHCO_3$ solution was added and the residue stirred at room temperature for 1 hr. The solid was filtered off, washed with water followed by 10 ml of diethyl ether. The resulting solid was dried under vacuum afford ethyl 7-ethyl-6-oxo-5H-1,5-naphthyridine-3-carboxylate (Intermediate 11, 1.738 g, 78%) as a light brown solid.

1H NMR (500 MHz, DMSO-d6) 1.14-1.28 (3H, m), 1.35 (3H, t), 2.58 (2H, q), 4.38 (2H, q), 7.83 (1H, s), 8.17 (1H, s), 8.90 (1H, s), 12.05 (1H, s); m/z ($ES^+$) $[M+H]^+$=247.

Intermediate 12: 3-ethyl-7-(hydroxymethyl)-1H-1,5-naohthyridin-2-one

Lithium aluminum hydride, 2 M in THF (29.2 mL, 58.47 mmol) was added dropwise to ethyl 7-ethyl-6-oxo-5H-1,5-naphthyridine-3-carboxylate (Intermediate 11, 7.2 g, 29.24 mmol) in tetrahydrofuran (150 mL) at 0° C. over a period of 45 minutes under nitrogen. The resulting mixture was stirred at 0° C. for 1.5 hours. The reaction mixture was quenched by dropwise addition of 1 M aq HCl (29 mL). The reaction mixture was concentrated and the solid was diluted with water (~150 ml) and 29 ml of 1 M HCl solution gave a yellow suspension. The solid was collected by filtration, washed with water, diethyl ether and dried to yield the crude product as a yellow solid (contaminated by some inorganic salt). This solid was suspended in a mixture of methanol and DCM (2:1) (400 ml) and heated to reflux. The solid was filtered off. This solid was resuspended in methanol/DCM mixture and repeated this procedure 5 times to get most of the product out from this mixture. The combined filtrate was then concentrated until about 100ml and the solid was collected by filtration, washed with ether, dried under vacuum to yield 3-ethyl-7-(hydroxymethyl)-1H-1,5-naphthyridin-2-one (Intermediate 12, 4.35 g, 72.8%) as yellow solid. 1H NMR (500 MHz, DMSO-d6) 1.18 (3H, t), 2.52-2.56 (2H, m), 4.61 (2H, d), 5.44 (1H, t), 7.61 (1H, s), 7.74 (1H, s), 8.37 (1H, s), 11.87 (1H, br s); m/z (ES+) [M+H]+=205.3

Example 4: 5-[4-[(7-ethyl-6-oxo-5H-1,5-naphthyridin-3-yl)methyl]piperazin-1-yl1]-N-methyl-pyridine-2-carboxamide

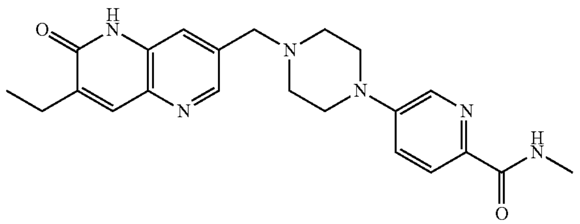 [SMILES: CCc1cc2ncc(CN3CCN(c4ccc(C(=O)NC)nc4)CC3)cc2[nH]c1=O]

Thionyl chloride (6.41 mL, 88.14 mmol) was added dropwise to a suspension of 3-ethyl-7-(hydroxymethyl)-1,5-naphthyridin-2(1H)-one (Intermediate 12, 3 g, 14.69 mmol) and N,N-dimethylformamide (0.114 mL, 1.47 mmol) in CH2Cl2 (60 mL) at 0° C. and the resulting solution was stirred at room temperature for 6 hours. The mixture was concentrated to dryness to give crude 7-(chloromethyl)-3-ethyl-1H-1,5-naphthyridin-2-one (Intermediate 17).

DIPEA (12.83 mL, 73.45 mmol) was added to a stirred solution of 7-(chloromethyl)-3-ethyl-1H-1,5-naphthyridin-2-one (Intermediate 17, crude from above), potassium iodide (0.488 g, 2.94 mmol) and N-methyl-5-piperazin-1-yl-pyridine-2-carboxamide, 2 HCl (Intermediate 13, 4.31 g, 14.69 mmol) in acetonitrile (50.00 mL) at 20° C. The resulting solution was stirred at 80° C. for 2 hours. Solvent was removed under vacuum. Crude material was diluted with water, basified with aq. NaHCO3 solution and extracted with ethyl acetate. Organic layer was dried over sodium sulphate and concentrated to give crude product. The resulting residue was purified by flash silica chromatography, elution gradient 0 to 15% MeOH in DCM. Product fractions were concentrated under reduced pressure to afford 5[4-[(7-ethyl-6-oxo-5H-1,5-naphthyridin-3-yl)methyl]piperazin-1-yl]-N-methyl-pyridine-2-carboxamide (Example 4, 3.93 g, 65.8%) as an off white partially crystalline solid. 1H NMR (500 MHz, DMSO-d6) 1.19 (3H, t), 2.53-2.59 (6H, m), 2.79 (3H, d), 3.33-3.39 (4H, m), 3.66 (2H, s), 7.39 (1H, dd), 7.64 (1H, s), 7.76 (1H, s), 7.83 (1H, d), 8.27 (1H, d), 8.36-8.40 (1H, m), 8.41 (1H, d), 11.85 (1H, s); m/z ($ES^+$) $[M]^+$=406.

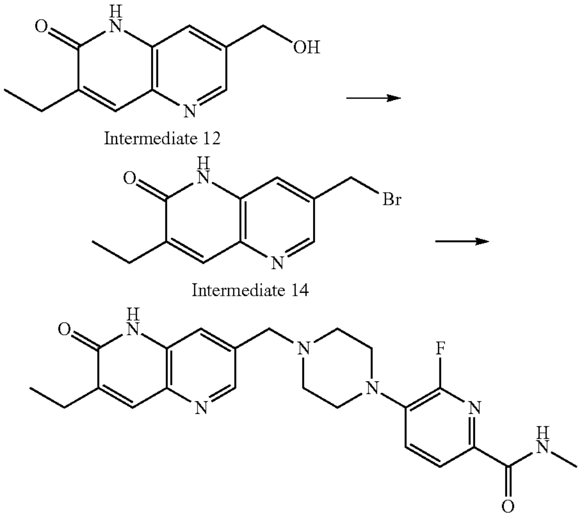

Intermediate 12

Intermediate 14

Example 5

-continued

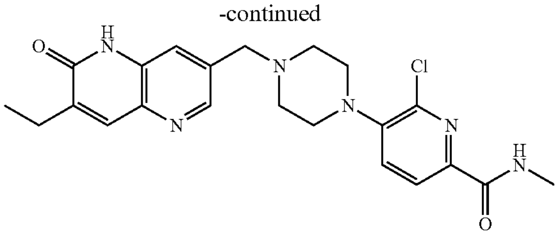

Example 6

Intermediate 14: 7-(bromomethyl)-3-ethyl-1H-1,5-naphthyridin-2-one

CBr4 (219 mg, 0.66 mmol) was added to a stirred solution of 3-ethyl-7-(hydroxymethyl)-1H-1,5-naphthyridin-2-one (Intermediate 12, 90 mg, 0.44 mmol) and triphenylphosphine (173 mg, 0.66 mmol) in CH2Cl2 (4 mL) at 0° C. The resulting solution was stirred at 0° C. for 2 hours. Reaction was concentrated under vacuum and the resulting residue was purified by flash silica chromatography, elution gradient 0 to 15% MeOH in DCM. Product fractions were concentrated under reduced pressure to afford 7-(bromomethyl)-3-ethyl-1H-1,5-naphthyridin-2-one (Intermediate 14, 84 mg, 71.4%) (Contains triphenyl phosphine oxide, difficult to separate). This compound was subjected to the next step without further purification.

$m/z\ (ES^+)\ [M]^+=267$

Example 5: 5-[4-[(7-ethyl-6-oxo-5H-1,5-naphthyridin-3-yl)methyl]piperazin-1-yl]-6-fluoro-N-methyl-pyridine-2-carboxamide

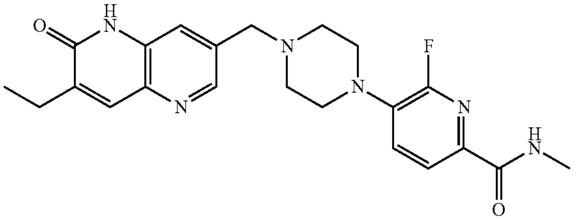 [SMILES: CCc1cc2ncc(CN3CCN(c4ccc(C(=O)NC)nc4F)CC3)cc2[nH]c1=O]

DIPEA (0.082 mL, 0.47 mmol) was added to a stirred solution of 7-(bromomethyl)-3-ethyl-1H-1,5-naphthyridin-2-one (Intermediate 14, 25 mg, 0.09 mmol) and 6-fluoro-N-methyl-5-piperazin-1-yl-pyridine-2-carboxamide, 2 HCl (Intermediate 23, 32.0 mg, 0.10 mmol) in acetonitrile (2 mL) at 20° C. The resulting solution was stirred at 70° C. for 2 hours. Solvent was removed under vacuum. The resulting residue was purified by flash silica chromatography, elution gradient 0 to 20% MeOH in DCM. Product fractions were concentrated under reduced pressure to afford 5-[4-[(7-ethyl-6-oxo-5H-1,5-naphthyridin-3-yl)methyl]piperazin-1-yl]-6-fluoro-N-methyl-pyridine-2-carboxamide (Example 5, 13.00 mg, 33%), pale yellow solid. 1H NMR (500 MHz, DMSO-d6) 1.19 (3H, t), 2.55 (2H, m, overlapped with solvent DMSO peak), 2.58 (4H, br d), 2.77 (3H, d), 3.19 (4H, br s), 3.67 (2H, s), 7.57 (1 H, dd), 7.63 (1H, s), 7.76 (1H, s), 7.85 (1H, d), 8.32-8.49 (2H, m), 11.85 (1H, s); m/z ($ES^+$) $[M+H]^+$=425.

Example 6: 6-chloro-5-[4-[(7-ethyl-6-oxo-5H-1,5-naphthyridin-3-yl)methyl]piperazin-1-yl]-N-methyl-pyridine-2-carboxamide

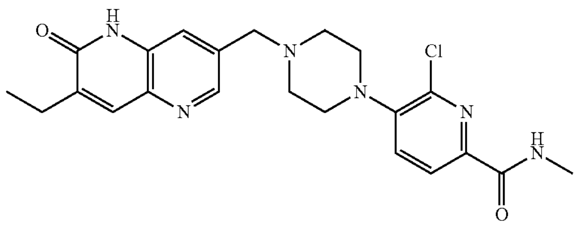 [SMILES: CCc1cc2ncc(CN3CCN(c4ccc(C(=O)NC)nc4Cl)CC3)cc2[nH]c1=O]

DIPEA (0.082 mL, 0.47 mmol) was added to a stirred solution of 7-(bromomethyl)-3-ethyl-1H-1,5-naphthyridin-2-one (Intermediate 14, 25 mg, 0.09 mmol) and 6-chloro-N-methyl-5-piperazin-1-yl-pyridine-2-carboxamide (Intermediate 48, 26.2 mg, 0.10 mmol) in acetonitrile (2 mL) at 20° C. The resulting solution was stirred at 70° C. for 2 hours. Solvent was removed under vacuum. The resulting residue was purified by flash silica chromatography, elution gradient 0 to 20% MeOH in DCM. Product fractions were concentrated under reduced pressure to afford 6-chloro-5[4-[(7-ethyl-6-oxo-5H-1,5-naphthyridin-3-yl)methyl]piperazin-1-yl]-N-methyl-pyridine-2-carboxamide (Example 6, 19.80 mg, 48.0%) as a pale-yellow solid. 1H NMR (500 MHz, DMSO-d6) 1.19 (3H, t), 2.55 (2H, m, overlapped with solvent DMSO peak), 2.58-2.65 (4H, m), 2.79 (3H, d), 3.13 (4H, br s), 3.68 (2H, s), 7.63 (1H, d), 7.67 (1H, d), 7.76 (1H, s), 7.94 (1H, d), 8.34-8.50 (2H, m), 11.85 (1H, s); m/z (ES$^+$) $[M+H]^+$=441.

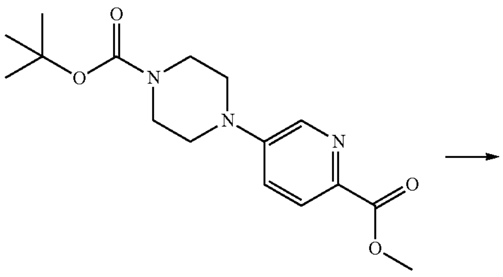

Intermediate 15

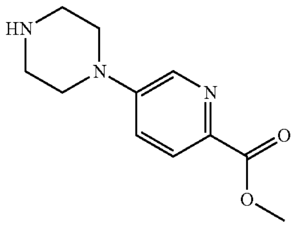

Intermediate 16

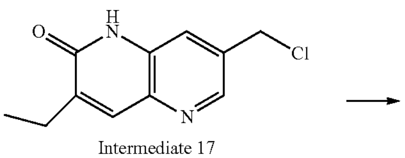

Intermediate 17

-continued

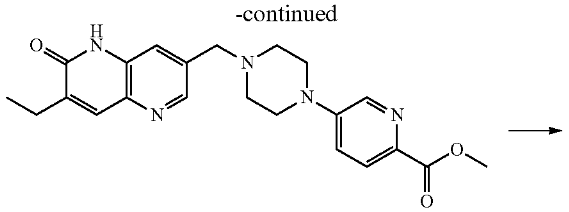

Intermediate 18

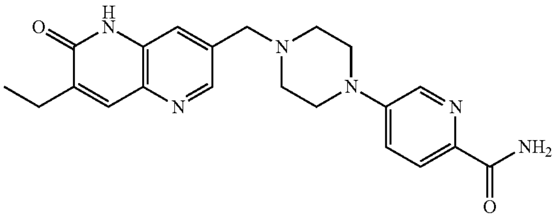

Example 7

Intermediate 16: Methyl 5-piperazin-1-ylpyridine-2-carboxylate

HCl in dioxane (4.67 mL, 18.67 mmol) was added to a stirred solution of tert-butyl 4-(6-methoxycarbonyl-3-pyridyl)piperazine-1-carboxylate (Intermediate 15, 600 mg, 1.87 mmol) in MeOH (1 mL) and the resulting solution was stirred at rt for 18 hours. Solvent was removed under vacuum to give methyl 5-piperazin-1-ylpyridine-2-carboxylate, 2 HCl (Intermediate 16, 543 mg, 99%) as light yellow solid.

1H NMR (500 MHz, DMSO-d6) 3.20 (4H, br s), 3.71 (4H, br s), 3.85 (3H, s), 7.58 (1H, br d), 7.99 (1H, br d), 8.43 (1H, br s), 9.73 (2H, br), 11.29-11.75 (1H, br) ; m/z (ES$^+$) $[M+H]^+$=222

Intermediate 18: Methyl 5-[4-[(7-ethyl-6-oxo-5H-1,5-naphthyridin-3-yl)methyl]piperazin-1-yl]pyridine-2-carboxylate DIPEA (944 µl, 5.40 mmol) was added to a stirred solution of 7-(chloromethyl)-3-ethyl-1H-1,5-naphthyridin-2-one, HCl (Intermediate 17, 200 mg, 0.77 mmol), sodium iodide (11.57 mg, 0.08 mmol) and methyl 5-piperazin-1-ylpyridine-2-carboxylate, 2 HCl (Intermediate 16, 250 mg, 0.85 mmol) in acetonitrile (6774 µl) at 20° C. The resulting solution was stirred at 80° C. for 3 hours. Solvent was removed under vacuum, 0.4 mL saturated sodium bicarbonate solution and 1.5 mL acetonitrile was added and reaction was stirred for 10 min. Solid was filtered off, washed with 2 mL water followed by 1 mL acetonitrile to give methyl 5-[4-[(7-ethyl-6-oxo-5H-1,5-naphthyridin-3-yl)methyl]piperazin-1-yl]pyridine-2-carboxylate (Intermediate 18, 158 mg, 50.2%) as off white solid. 1H NMR (500 MHz, DMSO-d6) 1.19 (3H, br t), 2.54-2.61 (6H, m), 3.40 (4H, br s), 3.66 (2H, s), 3.81 (3H, s), 7.35 (1H, br dd), 7.62 (1 H, s), 7.75 (1 H, s), 7.88 (1 H, br d), 8.28 - 8.47 (2H, m), 12.03 (1H, br); m/z (ES$^+$) $[M+H]^+$=408

Example 7: 5-[4-[(7-ethyl-6-oxo-5H-1,5-naphthyridin-3-yl)methyl]piperazin-1-yl]pyridine-2-carboxamide

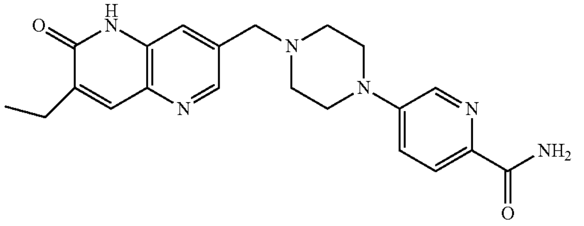 [SMILES: CCc1cc2ncc(CN3CCN(c4ccc(C(N)=O)nc4)CC3)cc2[nH]c1=O]

Ammonia in methanol (4 mL, 28.00 mmol) was added to methyl 5[4-[(7-ethyl-6-oxo-5H-1,5-naphthyridin-3-yl) methyl]piperazin-1-yl]pyridine-2-carboxylate (Intermediate 18, 60 mg, 0.15 mmol) and The resulting solution was heated to 50° C. for 24 h (sealed tube). Reaction was cooled to room temperature and the solid was filtered off and washed with 2 mL methanol to give 5-[4-[(7-ethyl-6-oxo-5H-1,5-naphthyridin-3-yl)methyl]piperazin-1-yl]pyridine-2-carboxamide (Example 7, 88 mg, 90%) as light brown solid. 1H NMR (500 MHz, DMSO-d6) 1.19 (3H, t), 2.56 (6H, m, overlapped with solvent DMSO peak), 3.35 (4H, br d), 3.66 (2H, s), 7.30 (1H, br s), 7.40 (1H, dd), 7.64 (1H, s), 7.76 (2H, s), 7.85 (1H, d), 8.28 (1H, d), 8.41 (1H, d), 11.61-11.98 (1H, m) ; m/z ($ES^+$) $[M+H]^+$=393.

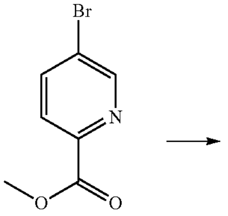

Intermediate 19

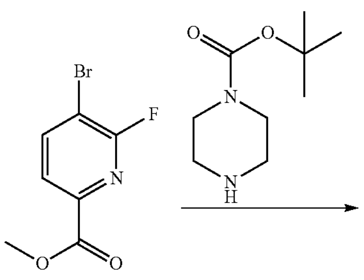

Intermediate 20

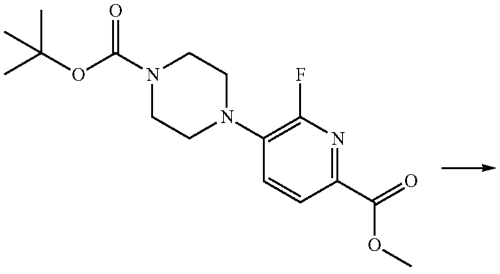

Intermediate 21

-continued

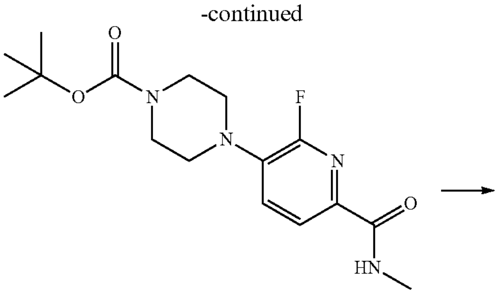

Intermediate 22

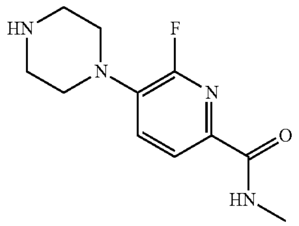

Intermediate 23

Intermediate 20: Methyl 5-bromo-6-fluoro-pyridine-2-carboxylate

An oven dried flask was charged with methyl 5-bromopyridine-2-carboxylate (Intermediate 19, 6 g, 27.77 mmol) in acetonitrile (60 mL). Silver (II) fluoride (14.18 g, 97.21 mmol) was added and the mixture was stirred at room temperature for overnight. Reaction mixture was filtered through filter paper and washed with DCM. The filtrate was concentrated to give a light brown solid. The residue was suspended in a mixture of DCM and sat. $NH_4Cl$ solution and the white suspension was filtered off. The organic layer was separated, and the aqueous layer was extracted with DCM (100 mlx2). The combined organic layers were dried over $Na_2SO_4$, filtered and concentrated. The resulting residue was purified by flash silica chromatography, elution gradient 0 to 25% EtOAc in hexanes. Product fractions were concentrated under reduced pressure to dryness to afford methyl 5-bromo-6-fluoro-pyridine-2-carboxylate (Intermediate 20, 5.98g yield 90%). $^1H$ NMR (500 MHz, CHLOROFORM-d) 4.01 (3H, s), 7.93 (1H, d), 8.15 (1H, t); m/z ($ES^+$) $[M]^+$=234.

Intermediate 21: Tert-butyl 4-(2-fluoro-6-methoxycarbonyl-3-Dvridyl)Diperazine-1-carboxylate A mixture of tert-butyl piperazine-1-carboxylate (13.11 g, 70.41 mmol), methyl 5-bromo-6-fluoro-pyridine-2-carboxylate (Intermediate 20,10.985 g, 46.94 mmol), RuphosPd-G3 (2.5 g, 2.99 mmol) and $Cs_2CO_3$ (38 g, 116.63 mmol) in 1,4-dioxane (200 mL) was stirred at 80° C. for overnight under $N_2$. The mixture was diluted with water and ethyl acetate, the layers were separated. The aqueous layer was extracted with DCM (100 mlx2). The combined organic layers were dried over $Na_2SO_4$, filtered and concentrated. The resulting residue was purified by flash silica chromatography, elution gradient 0 to 100% EtOAc in hexanes. Product fractions were concentrated under reduced pressure to dryness to afford tert-butyl 4-(2-fluoro-6-methoxycarbonyl-3-pyridyl)piperazine-1-carboxylate (Intermediate 21,14.00 g, 88%) as a yellow solid; 1H NMR (500 MHz, CHLOROFORM-d) 1.51 (9H, s), 3.16-3.32 (4H, m), 3.58-3.72 (4H, m), 3.98 (3H, s), 7.29-7.34 (1H, m), 8.00 (1H, d); m/z ($ES^+$) $[M+H]^+$=340.

Intermediate 22: Tert-butyl 4-[2-fluoro-6-(methylcarbamoyl)-3-pyridyl]piperazine-1-carboxylate tert-butyl 4-(2-fluoro-6-methoxycarbonyl-3-pyridyl)piperazine-1-carboxylate (Intermediate 21, 12.49 g, 36.80 mmol) in methylamine (120 mL, 36.80 mmol, 33 wt % in ethanol) was stirred at r.t for 24 hrs. (sealed tube). The solvent was removed under reduced pressure. The residue was dissolved into DCM and filtered through silica gel bed and washed with ethyl acetate. The filtrate was concentrated and dried under vacuum to afford tert-butyl 4-[2-fluoro-6-(methylcarbamoyl)-3-pyridyl]piperazine-1-carboxylate (Intermediate 22,12.45 g, 100%) as a yellow solid. 1H NMR (500 MHz, DMSO-d6) 1.42 (9H, s), 2.77 (3H, d), 3.04-3.16 (4H, m), 3.43-3.56 (4H, m), 7.59 (1H, dd), 7.80-7.93 (1H, m), 8.41 (1H, q); m/z ($ES^+$) $[M+H]^+$=340.

Intermediate 23: 6-fluoro-N-methyl-5-piperazin-1-yl-pyridine-2-carboxamide

HCl (4M in dioxane, 100 ml, 400.00 mmol) was added to a solution of tert-butyl 4-[2-fluoro-6-(methylcarbamoyl)-3-pyridyl]piperazine-1-carboxylate (Intermediate 22, 12.5 g, 36.94 mmol) in 1,4-dioxane (50 mL) at 0° C. the reaction was stirred for 5 h during which the temperature was warmed to room temperature to give a yellow suspension. The suspension was diluted with ether, solid was filtered off and washed with ether. This solid was dried under vacuum to afford 6-fluoro-N-methyl-5-piperazin-1-yl-pyridine-2-carboxamide, 2 HCl (Intermediate 23,11.42 g, 99%) as a light-yellow solid. 1H NMR (500 MHz, DMSO-d6) δ ppm 2.8 (d, J=4.6 Hz, 3 H) 3.3 (br s, 4 H) 3.4 (br d, J=4.4 Hz, 4 H) 7.6-7.7 (m, 1 H) 7.9 (d, J=8.1 Hz, 1 H) 8.4 (br d, J=4.4 Hz, 1 H) 9.0-9.3 (m, 2 H); m/z ($ES^+$) $[M+H]^+$=239

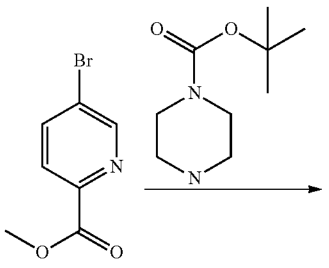

Intermediate 19

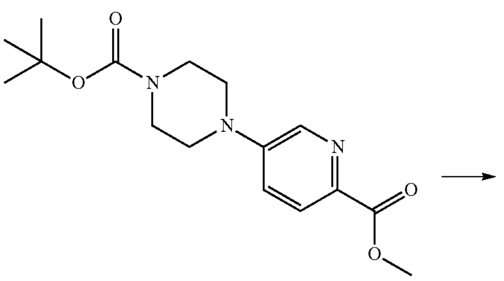

Intermediate 15

-continued

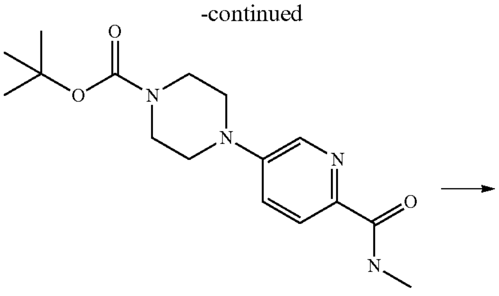

Intermediate 24

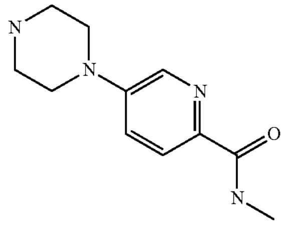

Intermediate 13

Intermediate 15: Tert-butyl 4-(6-methoxycarbonyl-3-pyridyl)piperazine-1-carboxylate Ruphos Pd G3 (4.07 g, 4.86 mmol) was added to a degassed mixture of methyl 5-bromopyridine-2-carboxylate (Intermediate 19, 30 g, 138.87 mmol), tert-butyl piperazine-1-carboxylate (27.2 g, 145.81 mmol), $Cs_2CO_3$ (90 g, 277.73 mmol) in 1,4-dioxane (200 mL) and the mixture was stirred at 110° C. for 6 hrs under $N_2$ atmosphere. The mixture was then cooled to room temperature, diluted with water, extracted with ethyl acetate (150 ml×3). Combined organic layers were dried over anhydrous $Na_2SO_4$ and filtered. To this filtrate was added 3-(Diethylenetriamino)propyl-functionalized silica gel (12 g, 1.3 mmol/g loading) and the mixture was stirred at r.t for 1 hr. The mixture was filtered, and the filtrate was concentrated to ~100 ml. The crystalline yellow solid was filtered off, washed with ether and dried under vacuum to afford tert-butyl 4-(6-methoxycarbonyl-3-pyridyl)piperazine-1-carboxylate (Intermediate 15, 26.36 g, 82 mmol, 59.1%) as a yellow solid. 1H NMR (500 MHz, CHLOROFORM-d) 1.50 (9H, s), 3.31-3.42 (4H, m), 3.56-3.68 (4H, m), 3.98 (3H, s), 8.04 (1H, d), 8.37 (1H, d); m/z ($ES^+$) $[M+H]^+$=322.

Intermediate 24: Tert-butyl 4-[6-(methylcarbamoyl)-3-pyridl]piperazine-1-carboxylate Methylamine (100 ml, 1155.26 mmol, 40% in water) was added to a solution of tert-butyl 4-(6-methoxycarbonyl-3-pyridyl)piperazine-1-carboxylate (Intermediate 15, 36 g, 112.02 mmol) in MeOH (100 mL) and the reaction was stirred at room temperature for 4hs to give a white suspension. The mixture was concentrated, the residue was partitioned between sat. $NH_4Cl$ solution and DCM, the layers were separated. The aqueous layer was extracted with DCM, the organic layers were combined, washed with brine, dried over $Na_2SO_4$, filtered and concentrated to give tert-butyl 4-[6-(methylcarbamoyl)-3-pyridyl]piperazine-1-carboxylate (Intermediate 24, 35.9 g, 100%) as a yellow solid. 1H NMR (500 MHz, CHLOROFORM-d) 1.49 (9H, s), 3.02 (3H, d), 3.26-3.35 (4H, m), 3.58-3.67 (4H, m), 7.23 (1H, dd), 7.81 (1H, br d), 8.07 (1H, d), 8.16 (1H, d); m/z ($ES^+$) $[M+H]^+$=321.

Intermediate 13: Carboxylate N-methyl-5-piperazin-1-yl-pyridine-2-carboxamide HCl (4 M in dioxane, 150 ml, 600.00 mmol) was added to a suspension of tert-butyl 4-[6-(methylcarbamoyl)-3-pyridyl]piperazine-1-carboxylate (Intermediate 24, 35.9 g, 112.05 mmol) in MeOH (50 mL) and the resulting orange suspension was stirred at r.t for 4 hr. About 80 ml of solvent was removed under reduced pressure and the mixture was diluted with ether and hexanes (200 ml, 1/1). The solid was collected by filtration, washed with hexanes, dried and dried under vacuum to afford N-methyl-5-piperazin-1-yl-pyridine-2-carboxamide, 2 HCl salt (Intermediate 13, 37.0 g, 100%) as a yellow solid. 1H NMR (500 MHz, DMSO-d6) 2.79 (3H, d), 3.22 (4H, br s), 3.53-3.67 (4H, m), 7.51 (1H, dd), 7.91 (1H, d), 8.33 (1H, d), 8.50 (1H, br s), 9.19 - 9.49 (2H, m); m/z ($ES^+$) $[M+H]^+$=221

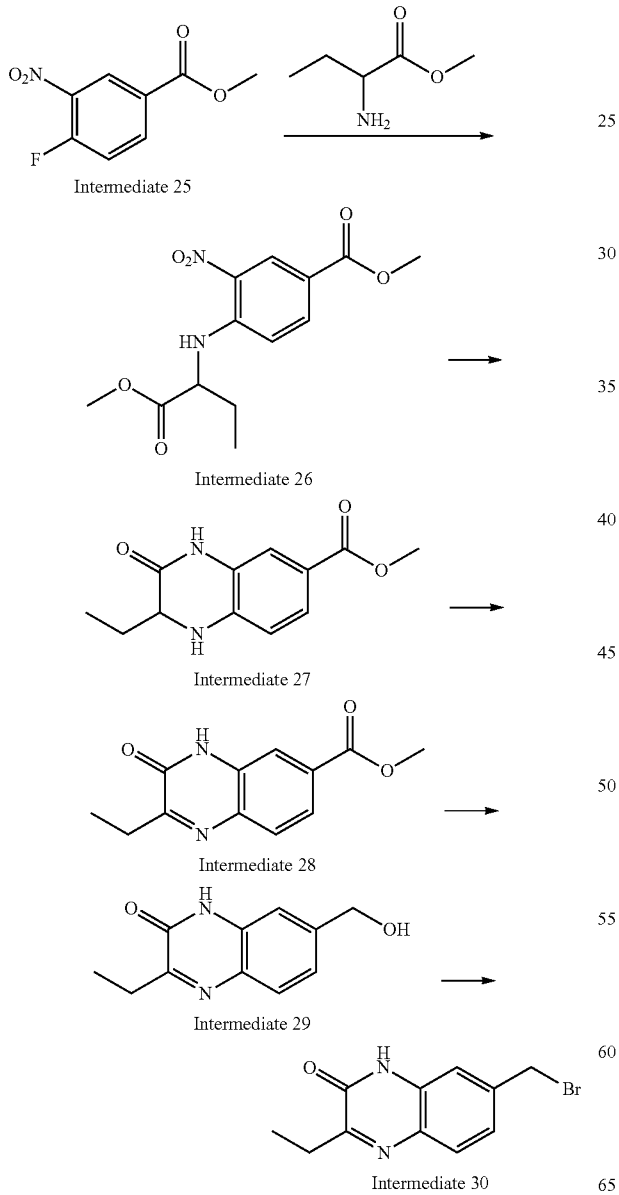

Intermediate 25

Intermediate 26

Intermediate 27

Intermediate 28

Intermediate 29

Intermediate 30

Intermediate 26: Methyl 4-(1-methoxycarbonylpropylamino)-3-nitro-benzoate sodium hydrogen carbonate (27.0 g, 321.39 mmol) was added portion wise to a stirred mixture of methyl 4-fluoro-3-nitrobenzoate (Intermediate 25, 16 g, 80.35 mmol), and methyl 2-aminobutanoate, HCl (14.81 g, 96.42 mmol) in THF (100 mL). The reaction mixture was stirred at room temperature for overnight. The reaction was quenched by addition of water, extracted with ethyl acetate. The combined organic layer was washed with saturated aq. $NaHCO_3$ solution, organic layer was dried over $MgSO_4$ and concentrated to dryness to give methyl 4-(1-methoxycarbonylpropylamino)-3-nitro-benzoate (Intermediate 26, 22.86 g, 96%) as a bright yellow solid. 1H NMR (500 MHz, DMSO-d6) 0.91 (3H, t), 1.75-2.12 (2H, m), 3.75 (3H, s), 3.85 (3H, s), 4.63-4.82 (1H, m), 7.15 (1H, d), 8.00 (1H, dd), 8.52-8.76 (2H, m).

Intermediate 27: Methyl 2-ethyl-3-oxo-2,4-dihydro-1H-quinoxaline-6-carboxylate Pd/C (4.15 g, 3.90 mmol) was added portion wise to a stirred solution of methyl 4-(1-methoxycarbonylpropylamino)-3-nitro-benzoate (Intermediate 26, 23.1 g, 77.97 mmol) in MeOH (300 mL) and the resulting slurry was stirred under H2 atmosphere at room temperature for 30 h. Methanol was removed under vacuum, 150 mL DMF was added and the mixture was stirred for 10 min. The palladium catalyst was filtered off on ceilite, washed with 50 mL of DMF (Material has very low solubility in organic solvents like MeOH/DCM/EtOAc). The filtrate was concentrated in Genevac to give methyl 2-ethyl-3-oxo-2,4-dihydro-1H-quinoxaline-6-carboxylate (Intermediate 27, 15.80 g, 87%) as a gray colored solid. Material was analyzed by NMR and subjected to the next step without purification. 1H NMR (500 MHz, DMSO-d6) 0.91 (3H, t), 1.63-1.73 (2H, m), 3.75 (3H, s), 3.90 (1H, td), 6.71 (1H, d), 6.84 (1H, s), 7.33 (1H, d), 7.41 (1H, dd), 10.39 (1H, s); m/z ($ES^+$) $[M]^+$=235.

Intermediate 28: Methyl 2-ethyl-3-oxo-4H-quinoxaline-6-carboxylate

DDQ (15.87 g, 69.92 mmol) was added to a suspension of methyl 2-ethyl-3-oxo-2,4-dihydro-1H-quinoxaline-6-carboxylate (Intermediate 27, 15.6 g, 66.59 mmol) in 1,4-dioxane (150 mL). The reaction mixture was stirred for overnight at room temperature. The mixture was slowly added to saturated aq $NaHCO_3$ solution (~500 ml) and stirred at room temperature for 20 min. The precipitate was filtered, washed with water (100 ml) and dried to yield methyl 2-ethyl-3-oxo-4H-quinoxaline-6-carboxylate as an off white solid (Intermediate 28, 11.40 g, 73.7%). 1H NMR (500 MHz, DMSO-d6) 1.23 (3H, t), 2.83 (2H, q), 3.89 (3H, s), 7.73-7.86 (2H, m), 7.89 (1H, d), 12.45 (1H, s); m/z ($ES^+$) $[M+H]^+$=233.

Intermediate 29: 3-ethyl-7-(hydroxymethyl)-1H-quinoxalin-2-one

Lithium aluminum hydride, 2 M in THF (49.1 mL, 98.17 mmol) was added dropwise to a slurry of methyl 2-ethyl-3-oxo-4H-quinoxaline-6-carboxylate (Intermediate 28, 11.4 g, 49.09 mmol) in tetrahydrofuran (350 mL) at 0° C. over a period of 50 minutes under nitrogen atmosphere. The resulting mixture was stirred at 0° C. for 1.5 hours. The reaction mixture was slowly poured into 1 M aq HCl (300 mL) at 0°

C. The reaction mixture was extracted with ethyl acetate (~300 ml×2) followed by extraction with DCM/methanol (5:1) (150 ml×3). The combined organic layers were concentrated to 300 ml and diluted with ether (200 ml) to give a suspension. The solid was collected by filtration, washed with ether, dried under vacuum to yield 3-ethyl-7-(hydroxymethyl)-1H-quinoxalin-2-one (Intermediate 29, 8.00 g, 80%). 1H NMR (500 MHz, DMSO-d6) 1.22 (3H, t), 2.80 (2H, q), 4.59 (2H, s), 5.19-5.61 (1H, m), 7.19 (1H, dd), 7.28 (1H, s), 7.66 (1H, d), 12.28 (1H, br s); m/z (ES$^+$) $[M+H]^+=205$.

Intermediate 30: 7-(bromomethyl)-3-ethyl-1H-quinoxalin-2-one

Hydrogen bromide (60 ml, 48 wt % in water) was added to 3-ethyl-7-(hydroxymethyl)-1 H-quinoxalin-2-one (Intermediate 29, 7.8 g, 38.19 mmol) (results in clear brown solution) and the mixture was stirred at 80° C. for 8 hrs, the reaction mixture was cooled to room temperature, poured to 150 mL iced water to give an off-white precipitate. The solid was filtered under vacuum and washed with water followed by diethyl ether and dried to give 7-(bromomethyl)-3-ethyl-1H-quinoxalin-2-one as a beige solid (Intermediate 30, 11.10 g, 84%) with 80% purity. 1H NMR (500 MHz, DMSO-d6) 1.20 (3H, t), 2.79 (2H, q), 4.79 (2H, s), 7.27-7.38 (2H, m), 7.69 (1H, d), 12.34 (1H, br s); m/z (ES$^+$) $[M]^+=267.0$.

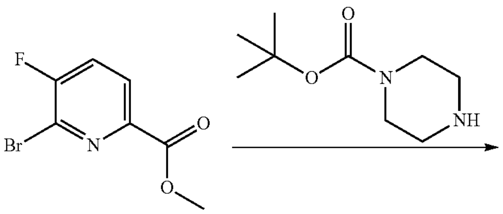

Intermediate 31

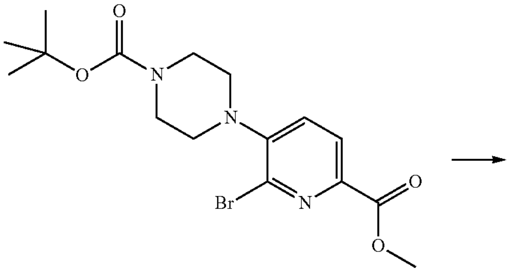

Intermediate 32

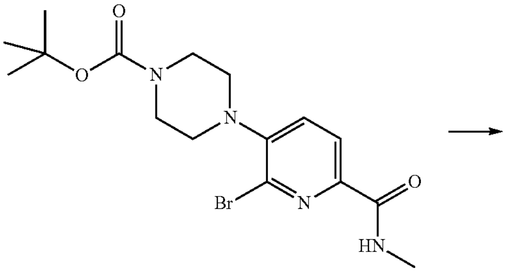

Intermediate 33

-continued

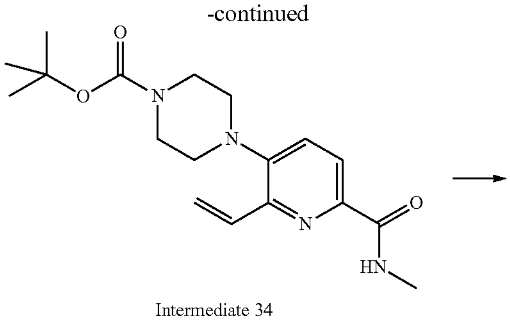

Intermediate 34

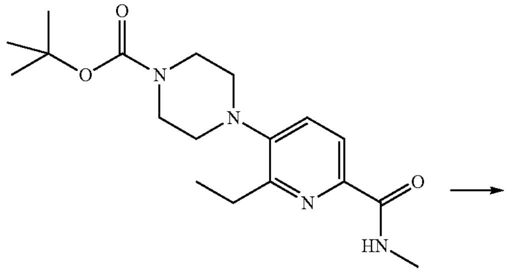

Intermediate 35

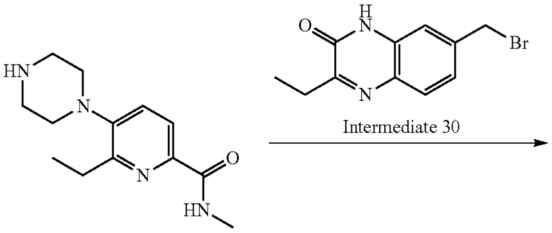

Intermediate 30

Intermediate 36

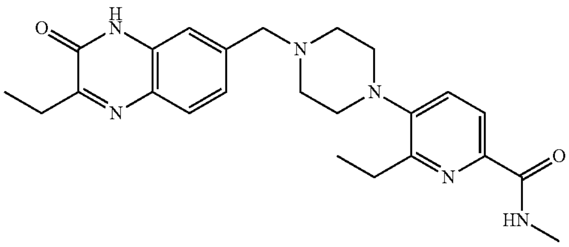

Example 8

Intermediate 32: Tert-butyl 4-(2-bromo-6-methoxycarbonyl-3-pyridyl)piperazine-1-carboxylate A mixture of tert-butyl piperazine-1-carboxylate (Intermediate 31, 2.57 g, 13.80 mmol), methyl 6-bromo-5-fluoropyridine-2-carboxylate (1.9 g, 8.12 mmol) and potassium carbonate (1.459 g, 10.55 mmol) in DMF (20 mL) was stirred at 110° C. for 5 hours, LCMS indicated full conversion. The mixture was cooled to r.t, diluted with DCM and water, the layers were separated. The water layer was extracted twice with DCM and the combined organic layers were dried over anhydrous $Na_2SO_4$, filtered and concentrated. The resulting residue was purified by flash silica chromatography, elution gradient 0 to 50% EtOAc in hexanes. Product fractions were concentrated under reduced pressure to dryness to afford tert-butyl 4-(2-bromo-6-methoxycarbonyl-3-pyridyl)piperazine-1-carboxylate (Intermediate 32, 2.200 g, 67.7%) as a light-yellow solid. 1H NMR (500 MHz, CHLOROFORM-d) 1.50 (9H, s), 3.05-3.20 (4H, m), 3.58-3.72 (4H, m), 3.98 (3H, s), 7.31 (1H, d), 8.06 (1H, d); m/z (ES$^+$) $[M+H]^+=400$.

Intermediate 33: Tert-butyl 4-[2-bromo-6-(methylcarbamoyl)-3-pyridl]piperazine-1-carboxylate A sealed pressure vessel was charged with tert-butyl 4-(2-bromo-6-methoxycarbonyl-3-pyridyl)piperazine-1-carboxylate (Intermediate 32, 2.2 g, 5.50 mmol) and methylamine (22 ml, 176.72 mmol) (33 wt. % in ethanol) and the mixture was heated at 60° C. for 2 hours, LCMS indicated full conversion. The mixture was concentrated, and the resulting residue was purified by flash silica chromatography, elution gradient 0 to 80% EtOAc in hexanes. Product fractions were concentrated under reduced pressure to dryness to afford tert-butyl 4-[2-bromo-6-(methylcarbamoyl)-3-pyridyl]piperazine-1-carboxylate (Intermediate 33, 2.200 g, 100%) as a white solid. 1H NMR (500 MHz, CHLOROFORM-d) 1.50 (9H, s), 3.02 (3H, d), 3.05-3.14 (4H, m), 3.56-3.74 (4H, m), 7.36 (1H, d), 7.68 (1H, br d), 8.11 (1H, d); m/z (ES$^+$) $[M+H]^+$=399.

Intermediate 34: Tert-butyl 4-[6-(methylcarbamoyl)-2-vinyl-3-pyridl]piperazine-1-carboxylate A mixture of tert-butyl 4-[2-bromo-6-(methylcarbamoyl)-3-pyridyl]piperazine-1-carboxylate (Intermediate 33, 200 mg, 0.50 mmol), tributyl(vinyl)stannane (0.161 ml, 0.55 mmol) and 2nd gen XPhos Pd cycle (19.71 mg, 0.03 mmol) in 1,4-dioxane (5 ml) was stirred at 100° C. under N2 for 2.5 hr, LCMS indicated full conversion. The mixture was diluted with DCM, washed with sat. $NH_4Cl$, the organic layer was dried (anhydrous $Na_2SO_4$), filtered and concentrated. The resulting residue was purified by flash silica chromatography, elution gradient 0 to 80% EtOAc in hexanes. Product fractions were concentrated under reduced pressure to dryness to afford tert-butyl 4-[6-(methylcarbamoyl)-2-vinyl-3-pyridyl]piperazine-1-carboxylate (Intermediate 34, 174 mg, 100%) as a white solid. m/z (ES$^+$) $[M+H]^+$=347

Intermediate 35: Tert-butyl 4-[2-ethyl-6-(methylcarbamoyl)-3-pyridyl]piperazine-1-carboxylate Pd/C (53.5 mg, 0.05 mmol) (10 wt % dry basis, wet load) was added to a solution of tert-butyl 4-[6-(methylcarbamoyl)-2-vinyl-3-pyridyl]piperazine-1-carboxylate (Intermediate 34, 174 mg, 0.50 mmol) MeOH (6 mL). The flask was degassed and refilled with $H_2$ (balloon). The mixture was stirred at r.t for overnight. LCMS indicated the reaction was not complete. More Pd/C (53.5 mg, 0.05 mmol), was added and the resulting mixture was stirred at r.t for 5 hrs under H2 atmosphere. The mixture was filtered through a pad of celite, washed with methanol, the filtrate was concentrated to dryness to yield tert-butyl 4-[2-ethyl-6-(methylcarbamoyl)-3-pyridyl]piperazine-1-carboxylate (Intermediate 35, 172 mg, 98%) as a colorless residue. 1H NMR (500 MHz, CHLOROFORM-d) 1.37 (3H, t), 1.51 (9H, s), 2.82-2.95 (6H, m), 3.05 (3H, d), 3.57-3.73 (4H, m), 7.39 (1H, d), 7.93-8.13 (2H, m); m/z (ES$^+$) $[M]^+$=348

Intermediate 36: 6-ethyl-N-methyl-5-piperazin-1-yl-pyridine-2-carboxamide

A mixture of tert-butyl 4-[2-ethyl-6-(methylcarbamoyl)-3-pyridyl]piperazine-1-carboxylate (Intermediate 35, 172 mg, 0.49 mmol) in HCl (4M in dioxane, 8 ml, 32.00 mmol) was stirred at r.t for 1 hr to give a white suspension. The mixture was diluted with ether and the solid filtered off and dried under vacuum to give 6-ethyl-N-methyl-5-piperazin-1-yl-pyridine-2-carboxamide, 2 HCl (Intermediate 36, 159 mg, 100%) as a light-yellow solid. 1H NMR (500 MHz, DMSO-d6) 1.31 (3H, t), 2.74-2.86 (5H, m), 3.00-3.14 (4H, m), 3.24 (4H, br s), 7.57 (1H, d), 7.82 (1H, d), 8.43 (1H, br d), 9.20 (2H, br s); m/z (ES$^+$) $[M+H]^+$=249.

Example 8: 6-ethyl-5-14-1(2-ethyl-3-oxo-4H-quinoxalin-6-vOmethvIlpiperazin-1-0-N-methvl-pyridine-2-carboxamide

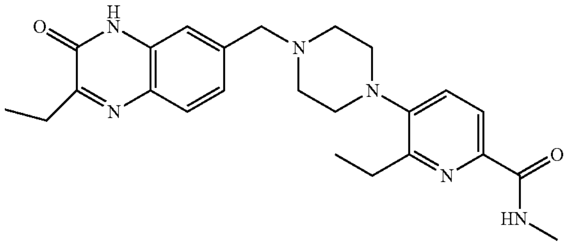 [SMILES: CCc1nc(C(=O)NC)ccc1N1CCN(Cc2ccc3nc(CC)c(=O)[nH]c3c2)CC1]

DIPEA (0.203 mL, 1.17 mmol) was added to a suspension of 6-ethyl-N-methyl-5-piperazin-1-yl-pyridine-2-carboxamide, 2 HCl (Intermediate 36, 75 mg, 0.23 mmol) and 7-(bromomethyl)-3-ethyl-1H-quinoxalin-2-one (Intermediate 30, 69.3 mg, 0.23 mmol) in acetonitrile (3 mL). The resulting mixture was stirred at 60° C. for 3 hrs, LCMS indicated full conversion. The mixture was cooled to r.t, concentrated, the residue was purified on Gilson reverse phase column (eluted with 0 to 95% ACN/water/0.1% TFA, 15 min run, collected from 5 to 9 min). The product containing fractions were concentrated and the residue was then dissolved into methanol and DCM. 300 mgs of tetraalkylammonium carbonite, polymer-bound (40-90 mesh, 2.5-3.5 mmol/g) and the mixture was stirred at r.t for 10 min. The mixture was then filtered and washed with methanol. The filtrate was concentrated, redissolved into a mixture of water/CAN and this mixture was lyophilized to dryness to yield 6-ethyl-5-[4-[(2-ethyl-3-oxo-4H-quinoxalin-6-yl)methyl]piperazin-1-yl]-N-methyl-pyridine-2-carboxamide (Example 8, 60.0 mg, 59.1%) as a light-yellow solid. 1H NMR (500 MHz, DMSO-d6) 1.22 (3H, t), 1.30 (3H, t), 2.54-2.69 (2H, m), 2.72-2.86 (7H, m), 2.93 (4H, br s), 3.26 (2H, s), 3.64 (2H, s), 7.17-7.33 (2H, m), 7.52 (1H, d), 7.69 (1H, br d), 7.80 (1H, d), 8.40 (1 H, br d), 12.25 (1H, br s); m/z (ES$^+$) $[M+H]^+$=435.

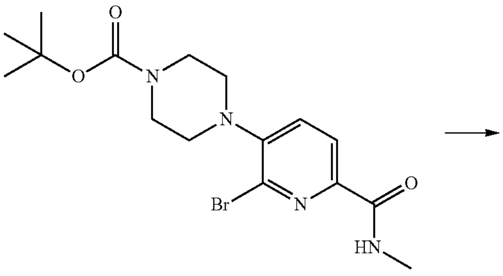

Intermediate 33

-continued

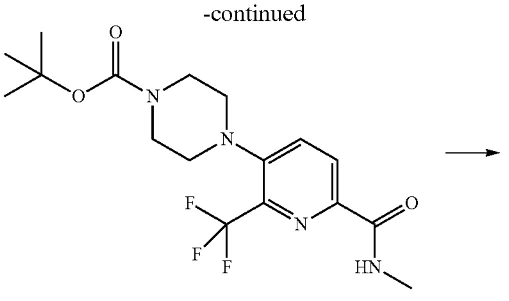

Intermediate 37

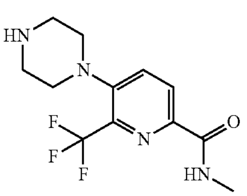

Intermediate 38

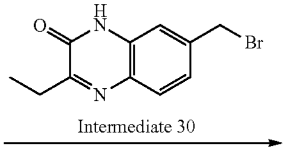

Intermediate 30

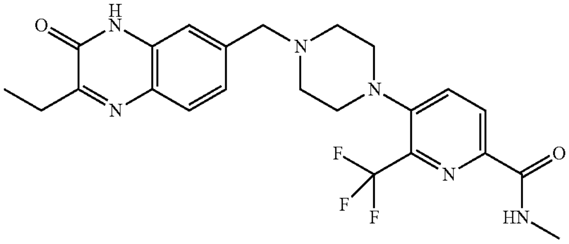

Example 9

Intermediate 37: Tert-butyl 4-[6-(methylcarbamoyl)-2-(trifluoromethyl)-3-pyridl]piperazine-1-carboxylate To a well stirred mixture of silver(I) fluoride (176 mg, 1.39 mmol) in DMF (2 mL), trimethyl(trifluoromethyl) silane (0.247 mL, 1.67 mmol) was added at room temperature. The mixture was stirred for 20 min which followed by addition of copper powder(133 mg, 2.09 mmol). After stirred for 4h the reaction mixture turned to blue color (indicator of the formation of $CuCF_3$). tert-butyl 4-(2-bromo-6-methoxycarbonyl-3-pyridyl)piperazine-1-carboxylate (Intermediate 33, 150 mg, 0.38 mmol) was added to the mixture and the resulting dark mixture was stirred at 90° C. for 18 hrs gave a brown suspension. LCMS indicated full conversion. The mixture was diluted with ethyl acetate and the solid was filtered off. The filtrate was washed with water followed by wash with brine. The organic layer was dried over anhydrous $Na_2SO_4$, filtered and concentrated. The resulting residue was purified by flash silica chromatography, elution gradient 0 to 70% EtOAc in hexanes. Product fractions were concentrated under reduced pressure to dryness to afford tert-butyl 4-[6-(methylcarbamoyl)-2-(trifluoromethyl)-3-pyridyl]piperazine-1-carboxylate (Intermediate 37, 146 mg, 100%) as a yellow residue. 1H NMR (500 MHz, CHLOROFORM-d) 1.50 (9H, s), 2.93-3.03 (4H, m), 3.05 (3H, d), 3.55-3.69 (4H, m), 7.71 (1H, d), 7.81 (1H, br d), 8.33 (1H, d); m/z ($ES^+$) $[M+H]^+$=389.

Intermediate 38: N-methyl-5-piperazin-1-yl-6-(trifluoromethyl)pyridine-2-carboxamide A mixture of tert-butyl 4-[6-(methylcarbamoyl)-2-(trifluoromethyl)-3-pyridyl]piperazine-1-carboxylate (Intermediate 37, 146 mg, 0.38 mmol) in HCl (4M in dioxane, 8 ml, 32.00 mmol) was stirred at r.t for 2 hrs. LCMS indicated full conversion. The solvent was concentrated to the volume 2ml, the mixture was diluted with ether/hexanes (15 ml, 5/1). The Solid was filtered off and dried under vacuum to afford N-methyl-5-piperazin-1-yl-6-(trifluoromethyl)pyridine-2-carboxamide, 2 HCl (Intermediate 38, 127 mg, 94%) as a pink solid. 1H NMR (500 MHz, DMSO-d6) 2.83 (3H, d), 3.21 (8H, br s), 8.09 (1H, d), 8.23 (1H, d), 8.46 (1H, br d), 9.08 (2H, br d); m/z ($ES^+$) $[M+H]^+$=289.

Example 9: 5-[4-[(2-ethyl-3-oxo-4H-quinoxalin-6-yl)methyl]piperazin-1-yl]-N-methyl-6-(trifluoromethyl)pyridine-2-carboxamide

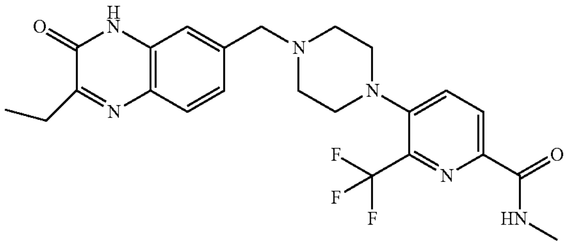 [SMILES: CCc1nc2ccc(CN3CCN(c4ccc(C(=O)NC)nc4C(F)(F)F)CC3)cc2[nH]c1=O]

DIPEA (0.121 mL, 0.69 mmol) was added to a suspension of N-methyl-5-piperazin-1-yl-6-(trifluoromethyl)pyridine-2-carboxamide, 2 HCl (Intermediate 38, 50 mg, 0.14 mmol) and 7-(bromomethyl)-3-ethylquinoxalin-2(1H)-one (Intermediate 30, 46.2 mg, 0.14 mmol) in acetonitrile (3 mL) and the mixture was stirred at 60° C. for 3 hrs. The mixture was cooled to r.t, concentrated, the residue was purified on Gilson reverse phase column (eluted with 0 to 95% ACN/water/0.1% TFA). The product containing fractions were concentrated at room temperature. The reside was then dissolved into methanol and DCM followed by addition of 250 mg of tetraalkylammonium carbonite polymer-bound (40-90 mesh, 2.5-3.5 mmol/g) and the mixture was stirred at room temperature for 10 min. The solid was then filtered off, washed with methanol and the filtrate was concentrated to give solid. This solid was then redissolved into a mixture of water/CH3CN and lyophilized to dryness to afford 5-[4-[(2-ethyl-3-oxo-4H-quinoxalin-6-yl)methyl]piperazin-1-yl]-N-methyl-6-(trifluorometh1)pyridine-2-carboxamide (Example 9, 40.0 mg, 60.9%) as a white solid. 1H NMR (500 MHz, CHLOROFORM-d) 1.40 (3H, t), 2.70 (4H, br s), 2.98-3.08 (5H, m), 3.12 (4H, br s), 3.72 (2H, br s), 7.2-7.32 (1H, m), 7.37 (1H, dd), 7.74 (1H, d), 7.79-7.88 (2H, m), 8.33 (1H, d), 11.06 (1H, br s); m/z ($ES^+$) $[M+H]^+$=475.

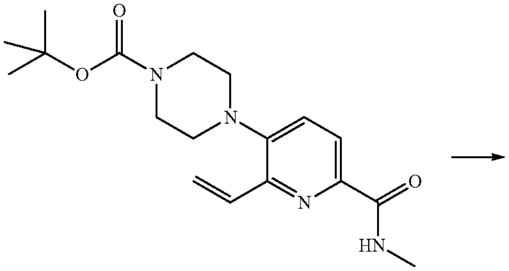

Intermediate 34

-continued

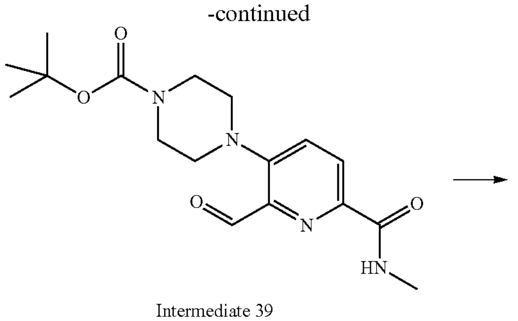

Intermediate 39

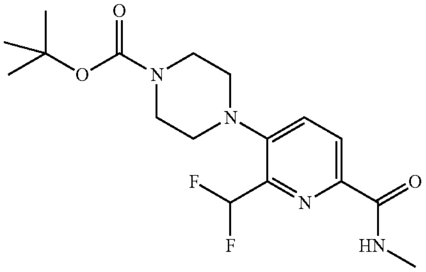

Intermediate 40

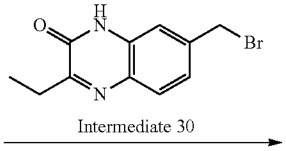

Intermediate 30

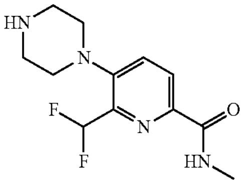

Intermediate 41

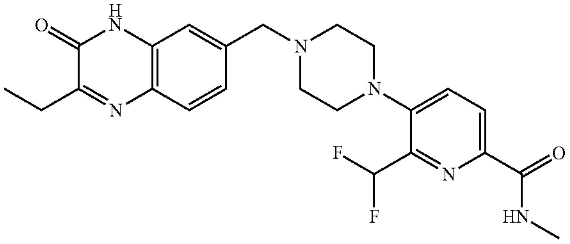

Example 10

Intermediate 39: Tert-butyl 4-[2-formyl-6-(methylcarbamoyl)-3-pyridyl]piperazine-1-carboxylate Osmium tetroxide in $H_2O$ (0.050 mL, 6.35 μmol) was added to a solution of tert-butyl 4-[6-(methylcarbamoyl)-2-vinyl-3-pyridyl]piperazine-1-carboxylate (Intermediate 34, 110 mg, 0.32 mmol), 2,6-lutidine (0.074 mL, 0.64 mmol) and sodium periodate (272 mg, 1.27 mmol) in THF (5 mL)/water (1 mL)/ tert-butanol (0.304 mL, 3.18 mmol) and the mixture was stirred at rt for overnight to give a yellow suspension. LCMS and TLC indicated full conversion. Reaction was diluted with water and extracted with ethyl acetate. After concentration the resulting residue was purified by flash silica chromatography, elution gradient 0 to 100% EtOAc in hexanes. Product fractions were concentrated under reduced pressure to dryness to afford tert-butyl 4-[2-formyl-6-(methylcarbamoyl)-3-pyridyl]piperazine-1-carboxylate (Intermediate 39, 100 mg, 90%) as a yellow solid. 1H NMR (500 MHz, CHLOROFORM-d) 1.50 (9H, s), 3.07 (3H, d), 3.14 - 3.29 (4H, m), 3.66 - 3.79 (4H, m), 7.49 (1 H, d), 7.86 (1 H, br d), 8.28 (1 H, d), 10.10 (1 H, s). m/z (ES+) [M+H]+=349.

Intermediate 40: tert-butvl 4-[2-(difluoromethyl)-6-(methvlcarbamov1)-3-ovridvIloiDerazine-1-carboxylate tert-butyl 4-[2-formyl-6-(methylcarbamoyl)-3-pyridyl]piperazine-1-carboxylate (Intermediate 39, 99 mg, 0.28 mmol) in $CH_2Cl_2$ (2 mL) was cooled to 0° C., DAST (0.710 mL, 0.71 mmol) (1M in DCM) was added and the resulting mixture was stirred at room temperature for 3 hr. TLC and LCMS indicated full conversion. Reaction was quenched with dropwise addition of sat. $NaHCO_3$ solution and extracted with DCM. The combined organics were dried over anhydrous $Na_2SO_4$, filtered and concentrated to give the crude product. the resulting residue was purified by flash silica chromatography, elution gradient 0 to 100% EtOAc in hexanes. Product fractions were concentrated under reduced pressure to dryness to afford tert-butyl 4-[2-(difluoromethyl)-6-(methylcarbamoyl)-3-pyridyl]piperazine-1-carboxylate (Intermediate 40, 94 mg, 89%) as an off white solid. 1H NMR (500 MHz, CHLOROFORM-d) 1.51 (9H, s), 2.89-3.03 (4H, m), 3.06 (3H, d), 3.54-3.73 (4H, m), 6.82-7.16 (1H, m), 7.64 (1H, d), 7.94 (1H, br d), 8.29 (1H, d); m/z ($ES^+$) $[M+H]^+$=371.

Intermediate 41: 6-(difluoromethyl)-N-methyl-5-piperazin-1-yl-pyridine-2-carboxamide A mixture of tert-butyl 4-[2-(difluoromethyl)-6-(methylcarbamoyl)-3-pyridyl]piperazine-1-carboxylate (Intermediate 40, 92 mg, 0.25 mmol) in Hl 4 M in 1, 4-dioxane (6 ml, 24.00 mmol) was stirred at r.t for 1.5 hr gave an orange suspension, the mixture was diluted with ether, filtered, the solid was redissolved into methanol, concentrated to dryness to yield 6-(difluoromethyl)-N-methyl-5-piperazin-1-yl-pyridine-2-carboxamide, 2 HCl (Intermediate 41, 56.0 mg, 65.7%) as an orange solid. 1H NMR (500 MHz, DMSO-d6) 2.83 (3H, d), 3.03-3.23 (5H, m), 3.30 (4H, br s), 7.06-7.49 (1H, m), 7.92 (1H, d), 8.13 (1H, d), 8.43 (1H, br d), 9.00 (2H, br d); m/z ($ES^+$) $[M+H]^+$=271.

Example 10: 6-(difluoromethyl)-5-[4-[(2-ethyl-3-oxo-4H-quinoxalin-6-yl)methyl]piperazin-1-yl]-N-methyl-pyridine-2-carboxamide

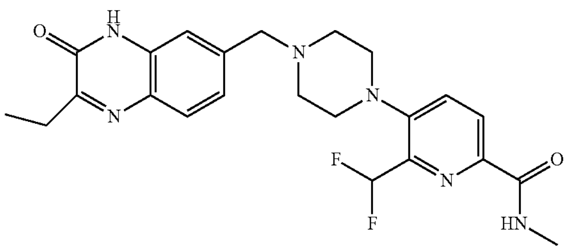 [SMILES: CCc1nc2ccc(CN3CCN(c4ccc(C(=O)NC)nc4C(F)F)CC3)cc2[nH]c1=O]

DIPEA (0.127 mL, 0.73 mmol) was added to a suspension of 6-(difluoromethyl)-N-methyl-5-piperazin-1-yl-pyridine-2-carboxamide, 2 HCl (Intermediate 41, 50 mg, 0.15 mmol) and 7-(bromomethyl)-3-ethylquinoxalin-2(1H)-one (Intermediate 30, 48.6 mg, 0.15 mmol) in acetonitrile (3 mL). The resulting mixture was stirred at 60° C. for 3 hrs, LCMS indicated full conversion. The mixture was concentrated, and the residue was purified on Gilson reverse phase column (eluted with 0 to 95% ACN/water/0.1% TFA). The product contain fractions were concentrated at room temperature. The reside was then dissolved into methanol and DCM followed by addition of 250 mg of tetraalkylammonium carbonite polymer-bound (40-90 mesh, 2.5-3.5mmol/g) and the mixture was stirred at room temperature for 10 min. The solid was then filtered off, washed with methanol and the filtrate was concentrated to give solid. This solid was then redissolved into a mixture of water/CH3CN and lyophilized to dryness to afford 6-(difluoromethyl)-5[4-[(2-ethyl-3-oxo-4H-quinoxalin-6-yl)methyl]piperazin-1-yl]-N-methyl-pyridine-2-carboxamide (Example 10, 50.0 mg, 75%) as a yellow solid. 1H NMR (500 MHz, CHLOROFORM-d) 1.40 (3H, t), 2.72 (4H, br s), 2.97-3.17 (9H, m), 3.73 (2H, s), 6.84-7.15 (1H, m), 7.32 (1H, s), 7.37 (1H, d), 7.64 (1H, d), 7.83 (1H, d), 7.95 (1H, br d), 8.29 (1H, d), 11.32-11.62 (1H, m); m/z ($ES^+$) $[M+H]^+$=457.

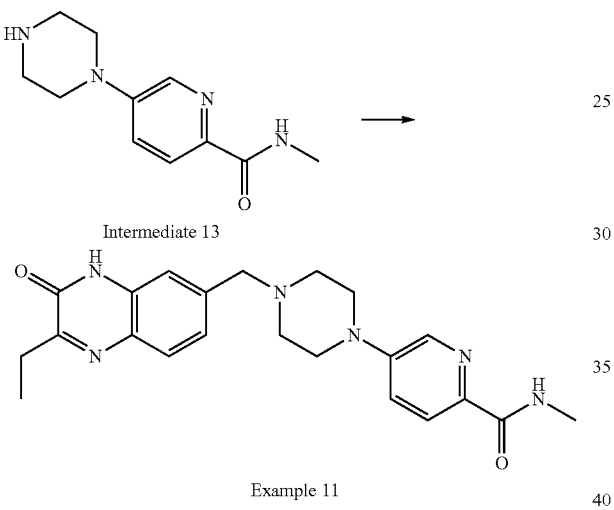

Example 11: 5-[4-[(2-ethyl-3-oxo-4H-quinoxalin-6-yl)methyl]piperazin-1-yl]-N-methyl-pyridine-2-carboxamide

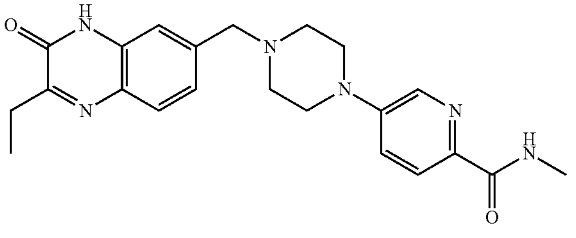 [SMILES: CCc1nc2ccc(CN3CCN(c4ccc(C(=O)NC)nc4)CC3)cc2[nH]c1=O]

In a 20 mL vial was added 7-(bromomethyl)-3-ethylquinoxalin-2(1H)-one (Intermediate 30, 0.147 g, 0.55 mmol) and N-methyl-5-piperazin-1-yl-pyridine-2-carboxamide, 2 HCl (Intermediate 13, 0.161 g, 0.55 mmol). The vial was sealed, evacuated, and refilled with $N_2$. Acetonitrile (3 mL) and DIPEA (0.481 mL, 2.75 mmol) were added to the vial and placed in a heating block pre-heated to 70 C. The reaction mixture was stirred at the same temperature for 2 hours and cooled to room temperature. The volume of the reaction was reduced to ⅓ of its initial volume under vacuum and aqueous $NaHCO_3$ solution was added (2 mL). The reaction mixture was stirred for 30 mins, filtered and the solid was washed with water (50 mL). The crude product was purified by flash silica chromatography using 0-30% MeOH in DCM to yield 5-[4-[(2-ethyl-3-oxo-4H-quinoxalin-6-yl)methyl]piperazin-1-yl]-N-methyl-pyridine-2-carboxamide (Example 11, 93.0 mg, 41.6%) as a light-yellow solid. $^1H$ NMR (500 MHz, DMSO-$d_6$) 1.22 (3H, t), 2.52-2.60 (4H, m), 2.73-2.85 (5H, m), 3.30 (4H, m, overlapped with water peak), 3.62 (2H, s), 7.22-7.31 (2H, m), 7.39 (1H, dd), 7.69 (1H, d), 7.83 (1H, d), 8.23-8.31 (1H, m), 8.39 (1H, br d), 12.13-12.36 (1 H, m); m/z ($ES^+$) $[M+H]^+$=407.

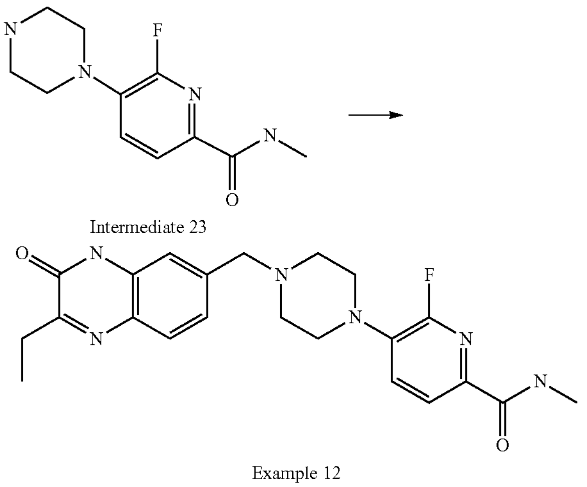

Example 12: 5-[4-[(2-ethyl-3-oxo-4H-quinoxalin-6-yl)methyl]piperazin-1-yl]-6-fluoro-N-methyl-pyridine-2-carboxamide

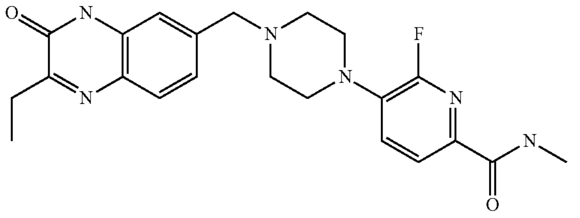 [SMILES: CCc1nc2ccc(CN3CCN(c4ccc(C(=O)NC)nc4F)CC3)cc2[nH]c1=O]

7-(bromomethyl)-3-ethylquinoxalin-2(1H)-one (Intermediate 30, 150 mg, 0.56 mmol) was added to 6-fluoro-N-methyl-5-piperazin-1-yl-pyridine-2-carboxamide(Intermediate 23, 60 mg, 0.25 mmol) and DIPEA (0.270 mL, 1.55 mmol) in NMP (2 mL). The resulting mixture was stirred at 80° C. for 2 hours. The solvent was removed under reduced pressure. The crude product was purified by preparative HPLC (Column: XBridge Shield RP18 OBD Column, 5um, 19×150 mm; Mobile Phase A: Water (10 MMOL/L $NH_4HCO_3$, 0.1% $NH_3 \cdot H_2O$), Mobile Phase B: ACN; Flow rate: 20 mL/min; Gradient: 28% B to 38% B in 8 min; 254; 220 nm; RT: 8.02 min). Fractions containing the desired compound were evaporated to dryness to afford 5-[4-[(2-ethyl-3-oxo-4H-quinoxalin-6-yl)methyl]piperazin-1-yl]-6-fluoro-N-methyl-pyridine-2-carboxamide (Example 12, 9 mg, 42.9%) as a white solid. $^1H$ NMR (400 MHz, $CD_3OD$)

δ 1.33 (3H, t), 2.65-2.72 (4H, m), 2.87-2.95 (5H, m), 3.26-3.30 (4H, m), 3.71 (2H, s), 7.33-7.41 (2H, m), 7.52 (1H, dd), 7.76 (1H, d), 7.90 (1H, dd); $^{19}$F NMR (376 MHz, CD3OD) δ-73.40; m/z (ES$^+$) [M+H]$^+$=425.

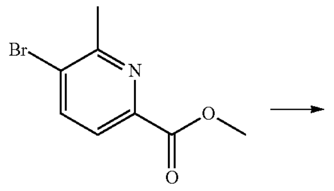

Intermediate 42

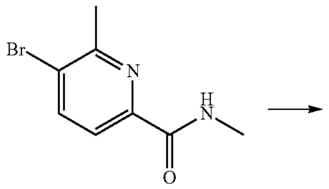

Intermediate 43

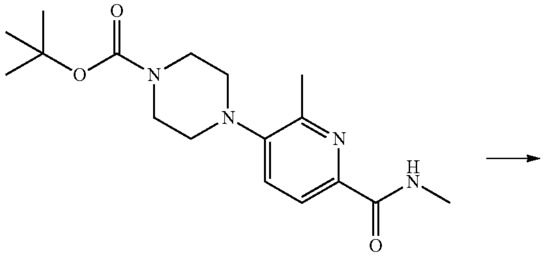

Intermediate 44

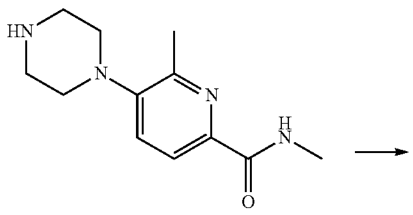

Intermediate 45

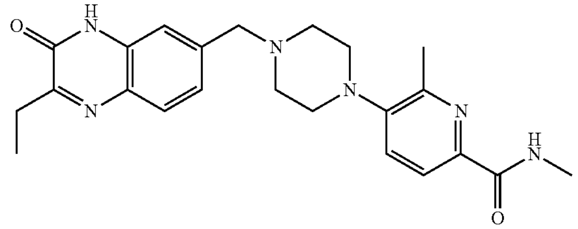 [SMILES: CCc1nc2ccc(CN3CCN(c4ccc(C(=O)NC)nc4C)CC3)cc2[nH]c1=O]

Example 13

Intermediate 43: 5-bromo-N,6-dimethylpicolinamide

A 2 M solution of methylamine in THF (20 mL, 40.00 mmol) was added to methyl 5-bromo-6-methylpicolinate (Intermediate 42, 2.0 g, 8.69 mmol) and the resulting mixture was stirred at 80° C. for 18 hours. The solvent was removed under reduced pressure. The crude product was purified by reverse phase chromatography, elution gradient 5 to 80% MeOH in water (0.1% $NH_4HCO_3$). Pure fractions were evaporated to dryness to afford 5-bromo-N,6-dimethylpicolinamide (Intermediate 43, 1.5 g, 75%) as a pale yellow solid. $^1$H NMR (400 MHz, DMSO-$d_6$) δ 2.65 (3H, s), 2.82 (3H, d), 7.75 (1H, d), 8.17 (1H, d), 8.57-8.76 (1H, m); m/z (ES$^+$) [M+H]$^+$=229

Intermediate 44: tert-butyl 4-(2-methyl-6-(methylcarbamoyl)pyridin-3-yl)piperazine-1-carboxylate 5-bromo-N,6-dimethylpicolinamide (Intermediate 43, 1.0 g, 4.37 mmol) was added to tert-butyl piperazine-1-carboxylate (0.894 g, 4.80 mmol), BINAP (0.272 g, 0.44 mmol), $Pd(OAc)_2$ (0.098 g, 0.44 mmol) and $Cs_2CO_3$ (3.56 g, 10.91 mmol) in toluene (20 mL) under nitrogen. The resulting mixture was stirred at 80° C. for 16 hours. The solvent was removed under reduced pressure. The crude product was purified by reverse phase chromatography, elution gradient 5 to 30% MeOH in water (0.4% $HCO_2H$). Pure fractions were evaporated to dryness to afford tert-butyl 4-(2-methyl-6-(methylcarbamoyl)pyridin-3-yl)piperazine-1-carboxylate (Intermediate 44, 1.2 g, 82%) as a brown solid. $^1$H NMR (300 MHz, $CD_3OD$) δ 1.50 (9H, s), 2.58 (3H, s), 2.92-3.00 (7H, m), 3.62 (4H, m), 7.50 (1H, d), 7.88 (1H, d); m/z (ES$^+$) [M+H]$^+$=335.

Intermediate 45: N,6-dimethyl-5-(piperazin-1-yl)picolinamide tert-butyl 4-(2-methyl-6-(methylcarbamoyl)pyridin-3-yl) piperazine-1-carboxylate (Intermediate 44, 1.18 g, 3.53 mmol) was added to a 4 M solution of HCl in the 1,4-dioxane (10 mL, 329.15 mmol). The resulting mixture was stirred at room temperature for 1 hour. The precipitate was collected by filtration, washed with petroleum ether (5 mL×2), $Et_2O$ (5 mL×2), and dried under vacuum to afford N,6-dimethyl-5-(piperazin-1-yl)picolinamide (Intermediate 45, 0.77 g, 81%) as an yellow solid. $^1$H NMR (300 MHz, $CD_3OD$) δ 2.86 (3H, s), 3.02 (3H, s), 3.42-3.54 (8H, m), 8.29 (2H, d); m/z (ES$^+$) [M+H]$^+$=235.

Example 13: 5-[4-[(2-ethyl-3-oxo-4H-quinoxalin-6-yl)methyl]piperazin-1-yl]-N,6-dimethyl-pyridine-2-carboxamide

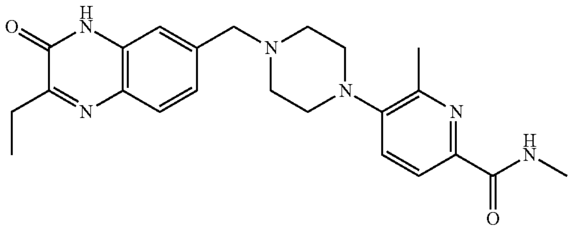

7-(bromomethyl)-3-ethylquinoxalin-2(1H)-one (Intermediate 30, 100 mg, 0.37 mmol) was added to N,6-dimethyl-5-(piperazin-1-yl)picolinamide (Intermediate 45, 90 mg, 0.33 mmol) and DIPEA (0.36 mL, 2.05 mmol) in NMP (2 mL). The resulting mixture was stirred at 80° C. for 2 hours. The solvent was removed under reduced pressure. The crude product was purified by preparative HPLC (Column: XBridge Prep OBD C18 Column 30×150 mm, 5 um; Mobile Phase A: Water (10 MMOL/L $NH_4HCO_3$), Mobile Phase B: ACN; Flow rate: 60 mL/min; Gradient: 30% B to 40% B in 7 min; 254; 220 nm; RT: 6.43 min). Fractions containing the desired compound were evaporated to dryness to afford 5-[4-[(2-ethyl-3-oxo-4H-quinoxalin-6-yl)methyl]piperazin- 1-yl]-N,6-dimethyl-pyridine-2-carboxamide (Example 13, 68.7 mg, 43.6%) as an off-white solid. $^{1}H$ NMR (400 MHz, $CD_3OD$) δ 1.33 (3H, t), 2.55 (3H, s), 2.71 (4H, s), 2.87-2.99 (5H, m), 3.05 (4H, t), 3.73 (2H, s), 7.35 (1H, s), 7.38 (1H, d), 7.49 (1H, d), 7.77 (1H, d), 7.87 (1H, d); m/z (ES+) $[M+]^+$=421.

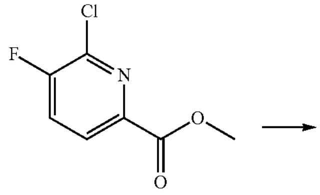

Intermediate 46

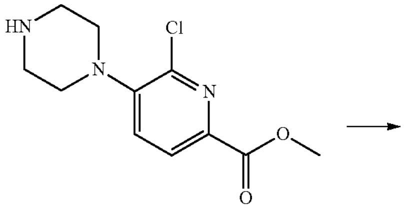

Intermediate 47

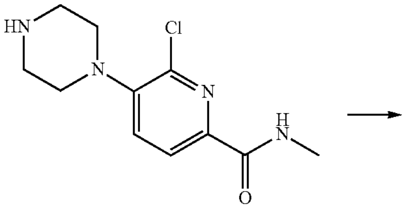

Intermediate 48

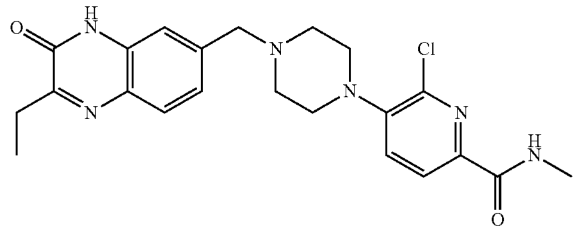 [SMILES: CCc1nc2ccc(CN3CCN(c4ccc(C(=O)NC)nc4Cl)CC3)cc2[nH]c1=O]

Example 14

Intermediate 47: Methyl 6-chloro-5-(piperazin-1-yl)picolinate

Piperazine (1.0 g, 11.61 mmol) was added to methyl 6-chloro-5-fluoropicolinate (Intermediate 46, 1.0 g, 5.28 mmol) in MeCN (30 mL). The resulting mixture was stirred at 80° C. for 18 hours. The solvent was removed under reduced pressure. The crude product was purified by reverse phase chromatography, elution gradient 5 to 60% MeCN in water (0.1% $NH_4HCO_3$). Pure fractions were evaporated to dryness to afford methyl 6-chloro-5-(piperazin-1-yl)picolinate (Intermediate 47, 1.28 g, 95%) as a red oil. $^{1}H$ NMR (400 MHz, DMSO-$d_6$) δ 2.81-2.91 (4H, m), 3.04-3.08 (4H, m), 3.85 (3H, s), 7.61 (1H, d), 8.00 (1H, d) (NH proton is not shown); m/z ($ES^+$) $[M+H]^+$=256.

Intermediate 48: 6-chloro-N-methyl-5-(piperazin-1-yl)picolinamide

A 2 M solution of methylamine in THF (40 mL, 80.00 mmol) was added to methyl 6-chloro-5-(piperazin-1-yl) picolinate (Intermediate 47, 1.26 g, 4.93 mmol). The resulting mixture was stirred at 80° C. for 18 hours. The solvent was removed under reduced pressure. The crude product was purified by reverse phase chromatography, elution gradient 5 to 60% MeCN in water (0.1% $NH_4HCO_3$). Pure fractions were evaporated to dryness to afford 6-chloro-N-methyl-5-(piperazin-1-yl)picolinamide (Intermediate 48, 1.12 g, 89%) as a pale yellow oil. $^{1}H$ NMR (300 MHz, DMSO-$d_6$) δ 2.79 (3H, d), 2.85-2.89 (4H, m), 2.97-3.02 (4H, m), 7.63 (1H, d), 7.94 (1H, d), 8.45 (1H, q) (Piperazine-NH proton is not shown); m/z ($ES^+$) $[M+H]^+$=255.

Example 14: 6-chloro-5-[4-[(2-ethyl-3-oxo-4H-quinoxalin-6-yl)methyl]piperazin-1-yl]-N-methyl-pyridine-2-carboxamide

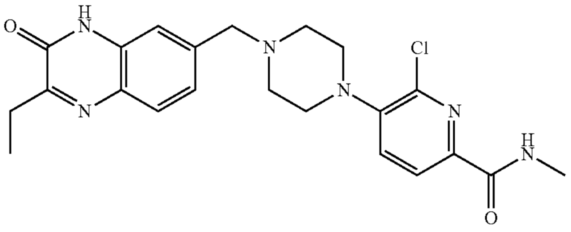

7-(bromomethyl)-3-ethylquinoxalin-2(1H)-one (Intermediate 30, 200 mg, 0.75 mmol) was added to 6-chloro-N-methyl-5-(piperazin-1-yl)picolinamide (Intermediate 48, 100 mg, 0.39 mmol) and DIPEA (0.358 mL, 2.05 mmol) in NMP (2 mL). The resulting mixture was stirred at 80° C. for 2 hours. The solvent was removed under reduced pressure. The crude product was purified by preparative HPLC (Column: XBridge Prep OBD C18 Column 30×150 mm 5 um; Mobile Phase A: Water (10 MMOL/L $NH_4HCO_3$), Mobile Phase B: ACN; Flow rate: 60 mL/min; Gradient: 30% B to 40% B in 8 min; 254; 220 nm; RT: 7.3 min). Fractions containing the desired compound were evaporated to dryness to afford 6-chloro-5-[4-[(2-ethyl-3-oxo-4H-quinoxalin-6-yl)methyl]piperazin-1-yl]-N-methyl-pyridine-2-carboxamide (Example 14, 52.6 mg, 30.4%) as a white solid. $^{1}H$NMR (400 MHz, $CD_3OD$) δ 1.33 (3H, t), 2.71 (4H, s), 2.87-2.96 (5H, m), 3.23 (4H, s), 3.73 (2H, s), 7.33-7.41 (2H, m), 7.62 (1H, d), 7.77 (1H, d), 8.00 (1H, d); m/z ($ES^+$) $[M+H]^+$=441.

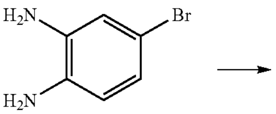

Intermediate 49

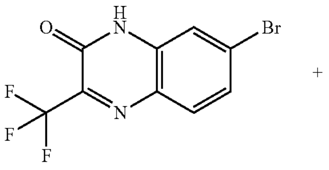

Intermediate 50

-continued

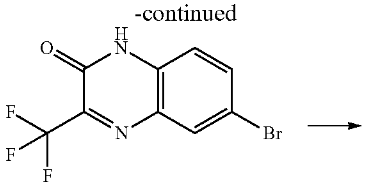

Intermediate 51

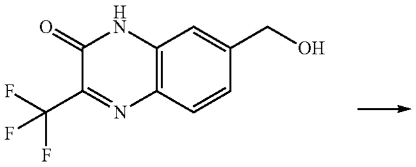

Intermediate 52

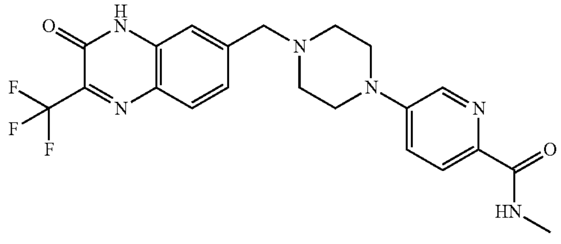

Example 15

Intermediate 50: 7-bromo-3-(trifluoromethyl)quinoxalin-2(1H)-one 4-bromobenzene-1,2-diamine (Intermediate 49, 0.9 g, 4.81 mmol) was added to methyl 3,3,3-trifluoro-2-oxopropanoate (0.9 g, 5.77 mmol) in toluene (10 mL). The resulting mixture was stirred at 100° C. for 60 minutes. The solvent was removed under reduced pressure. The crude product was purified by flash silica chromatography, elution gradient 0 to 50% EtOAc in petroleum ether. Pure fractions were evaporated to dryness to afford regioisomeric mixture of 7-bromo-3-(trifluoromethyl)quinoxalin-2(1H)-one and 6-bromo-3-(trifluoromethyl)quinoxalin-2(1H)-one (Intermediate 50+Intermediate 51, 1.28 g, 45.4%) as an off-white solid. A mixture of regioisomers were isolated, and the $^{1}H$ NMR spectrum was not interpreted; m/z ($ES^{+}$) $[M+H]^{+}$=295.

Intermediate 52: 7-(hydroxymethvl)-3-(trifluoromethyl)quinoxalin-2(1H)-one $Pd(Ph_3P)_4$ (0.3 g, 0.26 mmol) was added to a mixture of 7-bromo-3-(trifluoromethyl)quinoxalin-2(1H)-one and 6-bromo-3-(trifluoromethyl)quinoxalin-2(1H)-one (Intermediate 50+Intermediate 51, 1.2 g, 2.05 mmol) and (tributylstannyl)methanol (1.2 g, 3.74 mmol) in 1,4-dioxane (40 mL). The resulting mixture was stirred at 100° C. for 18 hours under nitrogen. The solvent was removed under reduced pressure. The crude product was purified by reverse phase chromatography, elution gradient 5 to 50% MeCN in water (0.1% $HCO_2H$). Pure fractions were evaporated to dryness to afford 7-(hydroxymethyl)-3-(trifluoromethyl)quinoxalin-2(1H)-one (Intermediate 52, 0.32 g, 64.0%) as an off-white solid. $^{1}H$ NMR (300 MHz, DMSO-$d_6$,) δ 4.63 (2H, d), 5.52 (1H, t), 7.30 (1H, dd), 7.38 (1H, d), 7.83 (1H, d), 13.05 (1H, s); m/z ($ES^{+}$) $[M+H]^{+}$=245.

Example 15: N-methyl-5-[4-[[3-oxo-2-(trifluoromethyl)-4H-quinoxalin-6-yl]methyl]piperazin-1-yl]pyridine-2-carboxamide

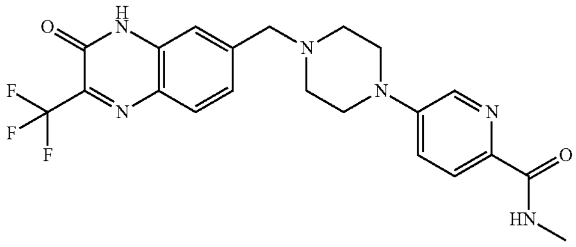 [SMILES: CNC(=O)c1ccc(N2CCN(Cc3ccc4nc(C(F)(F)F)c(=O)[nH]c4c3)CC2)cn1]

A solution of 33% HBr in AcOH (3 mL, 18.23 mmol) was added to 7-(hydroxymethyl)-3-(trifluoromethyl)quinoxalin-2(1H)-one (Intermediate 52, 111 mg, 0.45 mmol). The resulting mixture was stirred at 80° C. for 1 hour. The solvent was removed under reduced pressure. DIEA (0.5 mL, 2.86 mmol) and N-methyl-5-(piperazin-1-yl)picolinamide (Intermediate 13, 100 mg, 0.45 mmol) were added to the above mixture in NMP (3 mL). The resulting mixture was stirred at 80° C. for 1 hour. The solvent was removed under reduced pressure. The crude product was purified by preparative HPLC (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 22 B to 32 B in 7 min; 254; 220 nm; RT: 5.77. Fractions containing the desired compound were evaporated to dryness to afford N-methyl-5-[4-[[3-oxo-2-(trifluoromethyl)-4H-quinoxalin-6-yl]methyl]piperazin-1-yl]pyridine-2-carboxamide (Example 15, 44.0 mg, 21.71%) as a white solid. $^{1}H$ NMR (400 MHz, DMSO-$d_6$) δ 2.55-2.62 (m, 4H), 2.78 (d, 3H), 3.34-3.38 (t, 4H), 3.69 (s, 2H), 7.34-7.44 (m, 3H), 7.80-7.91 (m, 2H), 8.27 (d, 1H), 8.36-8.41 (m, 1H), 12.97 (s, 1H); $^{19}F$ NMR (376 MHz, DMSO-$d_6$) δ-68.36; m/z ($ES^{+}$) $[M+H]^{+}$=447.

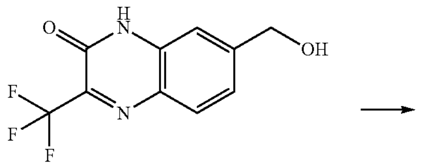

Intermediate 52

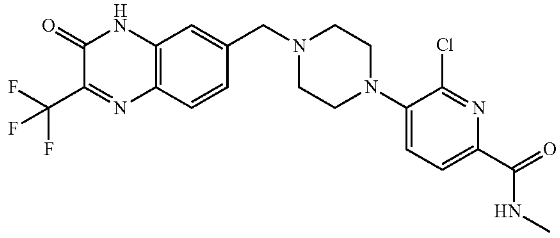

Example 16

Example 16: 6-chloro-N-methyl-5-[4-[[3-oxo-2-(trifluoromethyl)-4H-quinoxalin-6-yl]methyl]piperazin-1-yl]pyridine-2-carboxamide

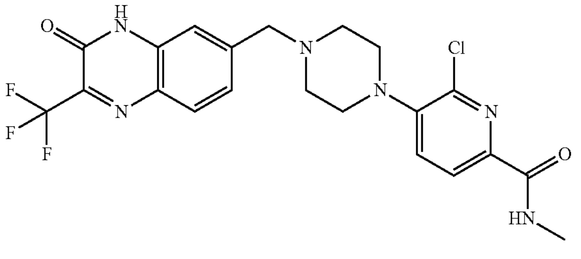 [SMILES: CNC(=O)c1ccc(N2CCN(Cc3ccc4nc(C(F)(F)F)c(=O)[nH]c4c3)CC2)c(Cl)n1]

33% HBr in AcOH (3 mL, 18.23 mmol) was added to 7-(hydroxymethyl)-3-(trifluoromethyl)quinoxalin-2(1H)-one (Intermediate 52, 43.1 mg, 0.18 mmol). The resulting mixture was stirred at 80° C. for 1 hour. The solvent was removed under reduced pressure. DIPEA (0.5 mL, 2.86 mmol) and 6-chloro-N-methyl-5-(piperazin-1-yl)picolinamide (Intermediate 48, 45 mg, 0.18 mmol) was added to the above mixture in NMP (5 mL). The resulting mixture was stirred at 80° C. for 1 hour. The solvent was removed under reduced pressure. The crude product was purified by preparative HPLC (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 10 B to 50 B in 7 min; 254; 220 nm; RT: 6.75. Fractions containing the desired compound were evaporated to dryness to afford 6-chloro-N-methyl-5-[4-[[3-oxo-2-(trifluoromethyl)-4H-quinoxalin-6-yl]methyl]piperazin-1-yl]pyridine-2-carboxamide (Example 16, 22.00 mg, 25.9%) as an off-white solid. $^1H$ NMR (400 MHz, DMSO-$d_6$) δ 2.56-2.64 (s, 4H), 2.79 (d, 3H), 3.09-3.17 (m, 4H), 3.71 (s, 2H), 7.36-7.42 (m, 2H), 7.67 (d, 1H), 7.88 (d, 1H), 7.94 (d, 1H), 8.39-8.44 (m, 1H), 12.89 (s, 1H); $^{19}F$ NMR (376 MHz, DMSO) δ-68.41; m/z (ES+) $[M+H]^+$=481.

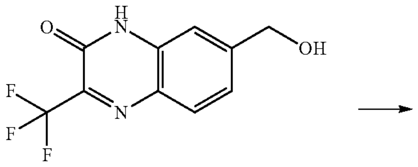

Intermediate 52

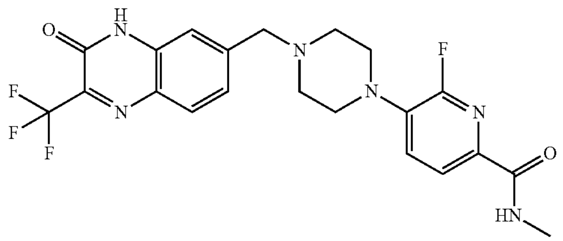

Example 17

Example 17: 6-fluoro-N-methyl-5-[4-[[3-oxo-2-(trifluoromethyl)-4H-quinoxalin-6-yl]methyl]piperazin-1-yl]pyridine-2-carboxamide

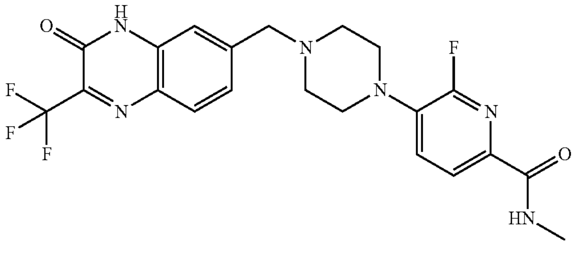 [SMILES: CNC(=O)c1ccc(N2CCN(Cc3ccc4nc(C(F)(F)F)c(=O)[nH]c4c3)CC2)c(F)n1]

33% HBr in AcOH (3 mL, 55.25 mmol) was added to 7-(hydroxymethyl)-3-(trifluoromethyl)quinoxalin-2(1H)-one (Intermediate 52, 102 mg, 0.42 mmol). The resulting mixture was stirred at 80° C. for 1 hour. The solvent was removed under reduced pressure. 6-fluoro-N-methyl-5-(piperazin-1-yl)picolinamide (Intermediate 23, 100 mg, 0.42 mmol) and DIPEA (0.5 mL, 2.86 mmol) was added to the above mixture in NMP (5 mL). The resulting mixture was stirred at 80° C. for 1 hour. The solvent was removed under reduced pressure. The crude product was purified by preparative HPLC (Column: XBridge Prep OBD C18 Column, 30×150 mm 5 um; Mobile Phase A: Water (10 MMOL/L $NH_4HCO_3$), Mobile Phase B: ACN; Flow rate: 60 mUmin; Gradient: 15 B to 40 B in 8 min; 254; 220 nm; RT: 7.2. Fractions containing the desired compound were evaporated to dryness to afford 6-fluoro-N-methyl-5-[4-[[3-oxo-2-(trifluoromethyl)-4H-quinoxalin-6-yl]methyl]piperazin-1-yl]pyridine-2-carboxamide (Example 17, 66.0 mg, 33.9%) as a white solid. $^1H$ NMR (400 MHz, DMSO-$d_6$) δ 2.55-2.69 (m, 4H), 2.77 (d, 3H), 3.15-3.23 (m, 4H), 3.69 (s, 2H), 7.33-7.46 (m, 2H), 7.58 (dd, 1H), 7.78-7.93 (m, 2H), 8.37-8.42 (m, 1H), 12.99 (s, 1H); $^{19}F$ NMR (376 MHz, DMSO-$d_6$) δ-68.36,-72.52; m/z (ES+) $[M+H]^+$=465.

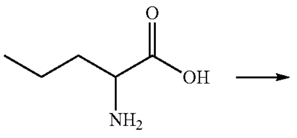

Intermediate 53

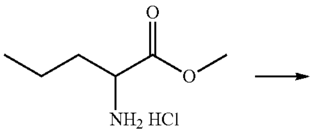

Intermediate 54

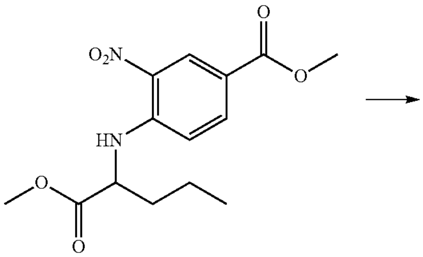

Intermediate 55

-continued

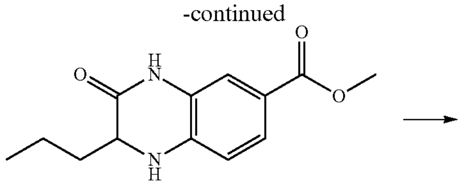

Intermediate 56

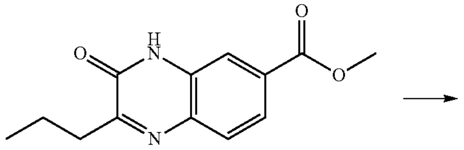

Intermediate 57

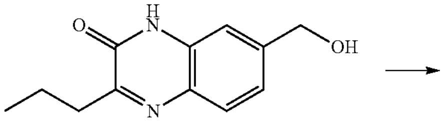

Intermediate 58

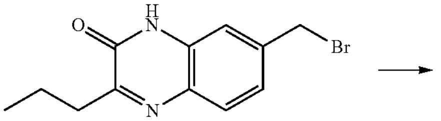

Intermediate 59

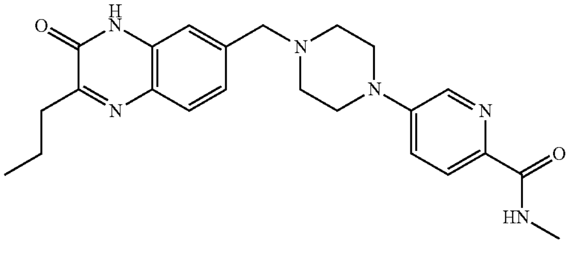

Example 18

Intermediate 54: Methyl 2-aminopentanoate Hydrochloride $SOCl_2$ (17 mL, 232.94 mmol) was added dropwise to 2-aminopentanoic acid (Intermediate 53, 10.0 g, 85.36 mmol) in MeOH (200 mL) at 0° C. The resulting mixture was stirred at room temperature for 18 hours. The solvent was removed under reduced pressure to afford methyl 2-aminopentanoate hydrochloride (Intermediate 54, 15.78 g, 110%) as a white solid. $^1H$ NMR (DMSO-$d_6$, 400 MHz) δ 0.88 (3H, t), 1.19-1.51 (2H, m), 1.67-1.83 (2H, m), 3.74 (3H, s), 3.89-3.93 (1H, m), 8.64 (3H, s); m/z (ES+) $[M+H]^+$=132.

Intermediate 55: Methyl 4-(1-methoxy-1-oxopentan-2-ylamino)-3-nitrobenzoate

Sodium bicarbonate (20.0 g, 238.08 mmol) was added to methyl 2-aminopentanoate hydrochloride (Intermediate 54, 15.57 g, 92.88 mmol) and methyl 4-fluoro-3-nitrobenzoate (9.0 g, 45.19 mmol) in THF (160 mL). The resulting mixture was stirred at room temperature for 18 hours. The solvent was removed under reduced pressure. The reaction mixture was diluted with EtOAc (150 mL), and washed sequentially with water (100 mL×1), saturated $NaHCO_3$ (100 mL×1) and saturated brine (100 mL×1). The organic layer was dried over $Na_2SO_4$, filtered and evaporated to afford methyl 4-(1-methoxy-1-oxopentan-2-ylamino)-3-nitrobenzoate (Intermediate 55, 14.09 g, 100%) as a yellow oil. $^1H$ NMR (400 MHz, DMSO-$d_6$) δ 0.89 (3H, t), 1.26-1.41 (2H, m), 1.84-1.94 (2H, m), 3.73 (3H, s), 3.83 (3H, s), 4.68-4.75 (1H, m), 7.12 (1H, d), 8.00 (1H, d), 8.60 (1H, d), 8.63 (1H, d); m/z (ES+) $[M+H]^+$=311.

Intermediate 56: methyl 3-oxo-2-propyl-1,2,3,4-tetrahvdroquinoxaline-6-carboxvlate $Pd(OH)_2/C$ (20% wt, 1.58 g, 2.25 mmol) was added to methyl 4-((1-methoxy-1-oxopentan-2-yl)amino)-3-nitrobenzoate (Intermediate 55, 14.05 g, 45.28 mmol) in MeOH (300 mL). The resulting mixture was stirred at room temperature under $H_2$ for 30 hours. The reaction mixture was filtered. The precipitate was washed with DMF (100 mL) and the filtrate was evaporated to dryness to afford crude product. The crude product was washed with DCM (10 mL) and dried under vacuum to afford methyl 3-oxo-2-propyl-1,2,3,4-tetrahydroquinoxaline-6-carboxylate (Intermediate 56, 9.12 g, 81%) as a white solid. $^1H$ NMR (400 MHz, DMSO-$d_6$) δ 0.87 (3H, t), 1.32-1.46 (2H, m), 1.57-1.64 (2H, m), 3.74 (3H, s), 3.88-3.93 (1H, m), 6.70 (1H, d), 6.83 (1H, d), 7.32 (1H, d), 7.40 (1H, dd), 10.38 (1H, s); m/z ($ES^+$) $[M+H]^+$=249.

Intermediate 57: Methyl 3-oxo-2-propyl-3,4-dihydroquinoxaline-6-carboxylate

DDQ (9.42 g, 41.50 mmol) was added to methyl 3-oxo-2-propyl-1,2,3,4-tetrahydroquinoxaline-6-carboxylate (Intermediate 56, 9.12 g, 36.73 mmol) in 1,4-dioxane (200 mL) . The resulting mixture was stirred at room temperature for 18 hours. The reaction mixture was diluted with saturated $NaHCO_3$ (200 mL). The resulting mixture was stirred at room temperature for 0.5 hour. The precipitate was collected by filtration, washed with water (1000 mL) and dried under vacuum to afford methyl 3-oxo-2-propyl-3,4-dihydroquinoxaline-6-carboxylate (Intermediate 57, 7.86 g, 87%) as an off-white solid. $^1H$ NMR (400 MHz, DMSO-$d_6$) δ 0.98 (3H, t), 1.68-1.80 (2H, m), 2.75-2.83 (2H, m), 3.89 (3H, s), 7.73-7.85 (2H, m), 7.88 (1H, d), 12.45 (1H, s); m/z ($ES^+$) $[M+H]^+$=247.

Intermediate 58: 7-(hydroxymethyl)-3-propylquinoxalin-2(1H)-one

A 1 M solution of DIBAL-H in THF (100 mL, 100.00 mmol) was added dropwise to methyl 3-oxo-2-propyl-3,4-dihydroquinoxaline-6-carboxylate (Intermediate 57, 7.81 g, 31.71 mmol) in THF (200 mL) at 0° C. The resulting mixture was stirred at room temperature for 18 hours. The reaction mixture was quenched with MeOl H (5 mL) and saturated aqueous Monopotassium monosodium tartrate tetrahydrate solution (20 mL), the organic layer was evaporated to afford 7-(hydroxymethyl)-3-propylquinoxalin-2(1H)-one (Intermediate 58, 1.2 g, 17.34%) as a white solid. $^1H$ NMR (400 MHz, DMSO-$d_6$) δ 0.97 (3H, t), 1.36-1.77 (2H, m), 2.71-2.79 (2H, m), 4.59 (2H, s), 5.39 (1H, s), 7.18 (1H, dd), 7.27 (1H, d), 7.65 (1H, d), 12.30 (1H, s); m/z ($ES^+$) $[M+H]^+$=219.

Intermediate 59: 7-(bromomethyl)-3-propylquinoxalin-2(1H)-one

33% HBr in AcOH (74.6 1.37 mmol) was added to 7-(hydroxymethyl)-3-propylquinoxalin-2(1 H)-one (Intermediate 58, 300 mg, 1.37 mmol). The resulting mixture was stirred at 80° C. for 1 hour. The solvent was removed under reduced pressure to afford 7-(bromomethyl)-3-propylquinoxalin-2(1H)-one (Intermediate 59, 600 mg, 155%) as a brown solid (the crude product was not pure and contained AcOH and other impurities. The product was used in the next step without further purification. The $^1$H NMR spectrum was not clean and was not interpreted; m/z (ES$^+$) $[M+H]^+$=282.

Example 18: N-methyl-5-[4-[(3-oxo-2-propyl-4H-quinoxalin-6-yl)methyl]piperazin-1-yl]pyridine-2-carboxamide

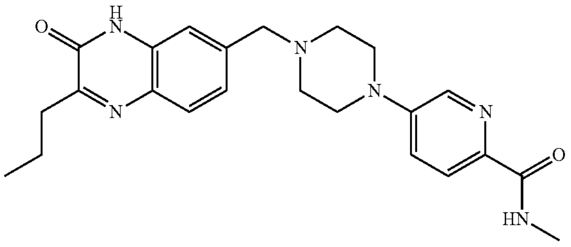 [SMILES: CCCc1nc2ccc(CN3CCN(c4ccc(C(=O)NC)nc4)CC3)cc2[nH]c1=O]

DIPEA (200 μL, 1.15 mmol) was added to 7-(bromomethyl)-3-propylquinoxalin-2(1H)-one (Intermediate 59, 200 mg, 0.71 mmol) and N-methyl-5-(piperazin-1-yl)picolinamide (Intermediate 13, 80 mg, 0.36 mmol) in NMP (3 mL). The resulting mixture was stirred at 80° C. for 1 hour. The solvent was removed under reduced pressure. The crude product was purified by preparative HPLC (Column: XBridge Shield RP18 OBD Column, 19×250 mm, 10 um; Mobile Phase A: Water (10 MMOL/L $NH_4HCO_3$, 0.1% $NH_3$. $H_2O$), Mobile Phase B: ACN; Flow rate: 20 mL/min; Gradient: 38 B to 50 B in 7 min; 254/220 nm; RT: 6.20. Fractions containing the desired compound were evaporated to dryness to afford N-methyl-5-[4-[(3-oxo-2-propyl-4H-quinoxalin-6-yl)methyl]piperazin-1-yl]pyridine-2-carboxamide (Example 18, 71.0 mg, 46.5%) as a white solid. $^1$H NMR (400 MHz,DMSO-d$_6$) δ 0.97 (3H, t), 1.66-1.80 (2H, m), 2.55-2.61 (4H, m), 2.73-2.85 (5H, m), 3.33-3.40 (4H, m), 3.62 (2H, s), 7.19 7.31 (2H, m), 7.40 (1H, dd), 7.68 (1H, d), 7.83 (1H, d), 8.27 (1H, d), 8.35-8.45 (1H, m), 12.26 (1H, s); m/z (ES+) $[M+H]^+$=421.

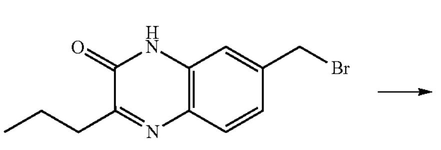

Intermediate 59

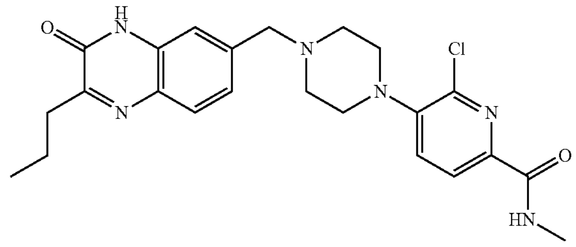

Example 19

Example 19: 6-chloro-N-methyl-5-[4-[(3-oxo-2-propyl-4H-quinoxalin-6-yl)methyl]piperazin-1-yl]pyridine-2-carboxamide

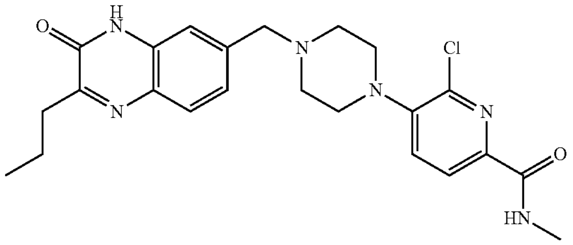 [SMILES: CCCc1nc2ccc(CN3CCN(c4ccc(C(=O)NC)nc4Cl)CC3)cc2[nH]c1=O]

DIPEA (200 μL, 1.15 mmol) was added to 7-(bromomethyl)-3-propylquinoxalin-2(1H)-one (Intermediate 59, 200 mg, 0.71 mmol) and 6-chloro-N-methyl-5-(piperazin-1-yl)picolinamide (Intermediate 48, 80 mg, 0.31 mmol) in NMP (3 mL). The resulting mixture was stirred at 80° C. for 1 hour. The solvent was removed under reduced pressure. The crude product was purified by preparative HPLC (Column: XBridge Shield RP18 OBD Column, 19×250 mm, 10 um; Mobile Phase A: Water (0.1% $HCO_2H$), Mobile Phase B: ACN; Flow rate: 20 mL/min; Gradient: 18 B to 30 B in 7 min; 254/220 nm; RT: 5.93. Fractions containing the desired compound were evaporated to dryness to afford 6-chloro-N-methyl-5-[4-[(3-oxo-2-propyl-4H-quinoxalin-6-yl)methyl]piperazin-1-yl]pyridine-2-carboxamide (Example 19, 52.0 mg, 36.4%) as a white solid. $^1$H NMR (400 MHz, DMSO-d$_6$) δ 0.97 (3H, t), 1.66-1.79 (2H, m), 2.55-2.65 (4H, m), 2.71-2.85 (5H, m), 3.06-3.12 (4H, m), 3.64 (2H, s), 7.20-7.32 (2H, m), 7.64-7.72 (2H, m), 7.94 (1H, d), 8.40-8.50 (1H, m), 12.27 (1H, s); m/z (ES$^+$) $[M+H]^+$=455.

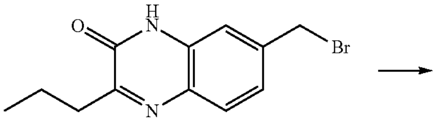

Intermediate 59

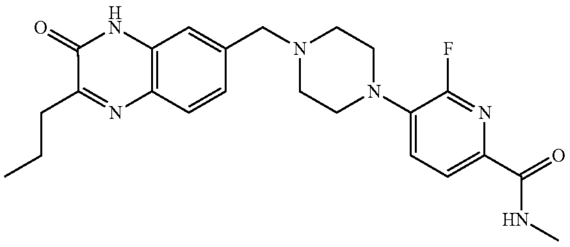 [SMILES: CCCc1nc2ccc(CN3CCN(c4ccc(C(=O)NC)nc4F)CC3)cc2[nH]c1=O]

Example 20

Example 20: 6-fluoro-N-methv1-5-14-113-oxo-2-Droov1-4H-ouinoxalin-6-vOmethvIloiDerazin-1-vilDvridine-2-carboxamide

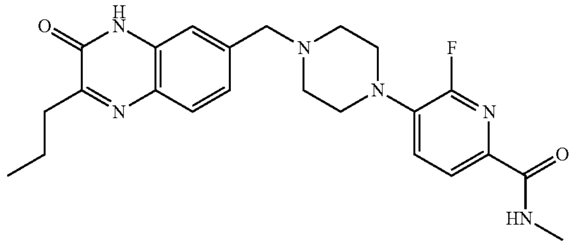

DIPEA (500 μl, 2.86 mmol) was added to 7-(bromomethyl)-3-propylquinoxalin-2(1H)-one (Intermediate 59, 200 mg, 0.71 mmol) and 6-fluoro-N-methyl-5-(piperazin-1-yl) picolinamide, 2 HCl (Intermediate 23, 100 mg, 0.32 mmol) in NMP (3 mL). The resulting mixture was stirred at 80° C. for 1 hour. The solvent was removed under reduced pressure. The crude product was purified by preparative HPLC (Column: SunFire C18 OBD Prep Column, 100 Å, 5 μm, 19 mm×250 mm; Mobile Phase A: Water (0.1% $HCO_2H$), Mobile Phase B: ACN; Flow rate: 25 mL/min; Gradient:10 B to 20 B in 13 min; 254/220 nm; RT: 12.13. Fractions containing the desired compound were evaporated to dryness to afford 6-fluoro-N-methyl-5-[4[(3-oxo-2-propyl-4H-quinoxalin-6-yl)methyl]piperazin-1-yl]pyridine-2-carboxamide (Example 20, 71.0 mg, 50.4%) as a white solid. $^1H$ NMR (400 MHz, DMSO-$d_6$) δ 0.97 (3H, t), 1.66-1.78 (2H, m), 2.54-2.60 (4H, m), 2.71-2.83 (5H, m), 3.14-3.25 (4H, m), 3.62 (2H, s), 7.19-7.33 (2H, m), 7.57 (1H, dd), 7.68 (1H, d), 7.85 (1H, dd), 8.37-5.43 (1H, m), 12.27 (1H, s); $^{19}F$ NMR (376 MHz, DMSO-$d_6$) δ-72.51; m/z ($ES^+$) $[M+H]^+$=439.

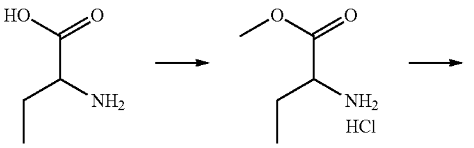

Intermediate 60 Intermediate 61

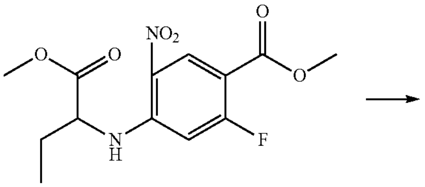

Intermediate 62

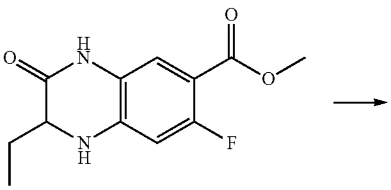

Intermediate 63

-continued

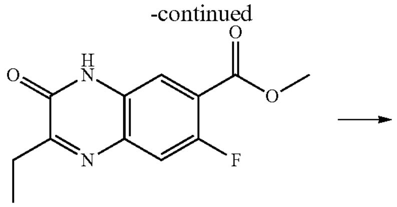

Intermediate 64

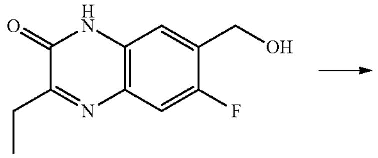

Intermediate 65

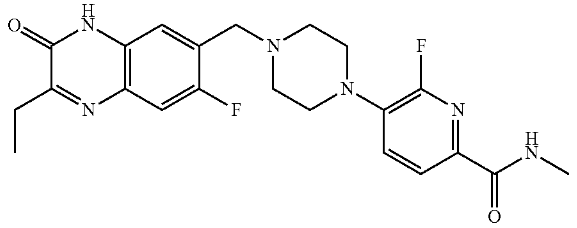 [SMILES: CCc1nc2cc(F)c(CN3CCN(c4ccc(C(=O)NC)nc4F)CC3)cc2[nH]c1=O]

Example 21

Intermediate 61: Methyl 2-aminobutanoate Hydrochloride $SOCl_2$ (17 mL, 232.94 mmol) was added dropwise to 2-aminobutanoic acid (Intermediate 60, 10.0 g, 96.97 mmol) in MeOH (100 mL) at 0° C. The resulting mixture was stirred at room temperature for 18 hours. The solvent was removed under reduced pressure to afford methyl 2-aminobutanoate hydrochloride (Intermediate 61, 14.84 g, 100%) as a white solid. $^1H$ NMR (400 MHz, DMSO-$d_6$) δ 0.91 (3H, t), 1.75-1.95 (2H, m), 3.73 (3H, s), 3.93 (1H, t), 8.72 (3H, s); m/z ($ES^+$) $[M+H]^+$=118

Intermediate 62: Methyl 2-fluoro-4-(1-methoxy-1-oxobutan-2-ylamino)-5-nitrobenzoate DIPEA (4.02 mL, 23.03 mmol) was added to methyl 2,4-difluoro-5-nitrobenzoate (1.0 g, 4.61 mmol) and methyl 2-aminobutanoate hydrochloride (Intermediate 61, 0.707 g, 4.61 mmol) in NMP (10 mL). The resulting mixture was stirred at rt for 5 hours. The crude product was purified by reverse phase chromatography, elution gradient 5 to 80% MeCN in water (0.1% $NH_4HCO_3$). Pure fractions were evaporated to dryness to afford methyl 2-fluoro-4-(1-methoxy-1-oxobutan-2-ylamino)-5-nitrobenzoate (Intermediate 62, 1.2 g, 83%) as a black solid. $^1H$ NMR (400 MHz, DMSO-$d_6$) δ 0.88 (3H, t), 1.78-2.03 (2H, m), 3.75 (3H, s), 3.83 (3H, s), 4.73-4.80 (1H, m), 7.06 (1H, d), 8.66-8.72 (2H, m); m/z ($ES^+$) $[M+H]^+$=315.

Intermediate 63: Methyl 2-ethyl-7-fluoro-3-oxo-1,2,3,4-tetrahydroquinoxaline-6-carboxylate Methyl 2-fluoro-4-((1-methoxy-1-oxobutan-2-yl)amino)-5-nitrobenzoate (Intermediate 62, 1.15 g, 3.66 mmol) was added to 20 wt % $Pd(OH)_2$ (500 mg, 0.71 mmol) in MeOH (300 mL) and ethyl acetate (50 mL) under hydrogen. The resulting mixture was stirred at room temperature for 3 days.

The reaction did not go to completion. The reaction mixture was filtered. The organic layer was evaporated to afford crude product, methyl 2-ethyl-7-fluoro-3-oxo-1,2,3,4-tetrahydroquinoxaline-6-carboxylate (Intermediate 63, 0.780 g, 85%), as a brown gum. The crude product was used in the next step directly without further purification. The crude product was not clean, and the $^{1}$HNMR spectrum was not interpreted; m/z ($ES^+$) $[M+H]^+$=253.

Intermediate 64: Methyl 2-ethyl-7-fluoro-3-oxo-3,4-dihydropuinoxaline-6-carboxvlate Methyl 2-ethyl-7-fluoro-3-oxo-1,2,3,4-tetrahydroquinoxaline-6-carboxylate (Intermediate 63, 760 mg, 3.01 mmol) was added to DDQ (821 mg, 3.62 mmol) in DCM (20 mL). The resulting mixture was stirred at room temperature for 2 hours. The reaction went to completion. The resulting mixture was concentrated under reduced pressure to obtain a brown solid. Aq $NaHCO_3$ saturated solution (10 mL) was added to the solid and stirred at room temperature for 1 hour. The precipitate was filtered and rinsed with additional aq $NaHCO_3$ solution (10 mL×5). The solid was dried under vacuum to afford methyl 2-ethyl-7-fluoro-3-oxo-3,4-dihydroquinoxaline-6-carboxylate (Intermediate 64, 750 mg, 99%) as a brown solid. $^{1}$H NMR (300 MHz, DMSO-d6) δ 1.20 (3 H, t), 2.82 (2 H, q), 3.87 (3 H, s), 7.65 (1 H, d), 7.76 (1 H, d), 12.42 (1 H, s); m/z ($ES^+$) $[M+H]^+$=251.

Intermediate 65: 3-ethyl-6-fluoro-7-(hydroxymethyl)quinoxalin-2(1H)-one

A 1 M solution of diisobutylaluminum hydride in THF (15.35 mL, 15.35 mmol) was added portionwise to methyl 2-ethyl-7-fluoro-3-oxo-3,4-dihydroquinoxaline-6-carboxylate (Intermediate 64, 640 mg, 2.56 mmol) in THF (300 mL). The resulting mixture was stirred at room temperature for 16 hours. The reaction went to completion. The reaction mixture was quenched with saturated potassium sodium tartrate aqueous solution (20 mL) and MeOH (10 mL) at 0° C. The resulting mixture was stirred for 1 hour at room temperature. The reaction mixture was filtered and washed with THF (50 mL×3). The organic layer was evaporated to dryness to afford the crude product. The crude product was purified by reverse phase chromatography, elution gradient 5 to 60% MeOH in water (0.4% $HCO_2H$). Pure fractions were evaporated to dryness to afford 3-ethyl-6-fluoro-7-(hydroxymethyl)quinoxalin-2(1 H)-one (Intermediate 65, 110 mg, 19.37%) as an off-white solid. $^{1}$H NMR(400 MHz, DMSO-$d_6$) δ 1.21 (3H, t), 2.80 (2H, q), 4.63 (2H, d), 5.49 (1H, t), 7.41 (1H, d), 7.49 (1H, d), 12.36 (1H, s); m/z ($ES^+$) $[M+H]^+$=223.

Example 21: 5-[4-[(2-ethyl-7-fluoro-3-oxo-4H-quinoxalin-6-yl)methyl]piperazin-1-yl]-6-fluoro-N-methyl-pyridine-2-carboxamide

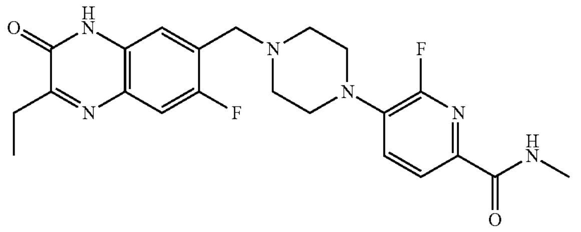

3-ethyl-6-fluoro-7-(hydroxymethyl)quinoxalin-2(1H)-one (Intermediate 65, 50 mg, 0.23 mmol) was added to 33% HBr in the AcOH (2 mL, 12.15 mmol). The resulting mixture was stirred at 80° C. for 2 hours. The reaction mixture was evaporated under vacuum to afford 7-(bromomethyl)-3-ethyl-6-fluoroquinoxalin-2(1H)-one (crude product). The product was used in the next step directly without further purification. DIPEA (0.196 mL, 1.13 mmol) was added to 7-(bromomethyl)-3-ethyl-6-fluoroquinoxalin-2(1H)-one and 6-fluoro-N-methyl-5-(piperazin-1-yl)picolinamide (Intermediate 23, 70 mg, 0.29 mmol) in NMP (2 mL). The resulting mixture was stirred at 80° C. for 2 hours. The resulting mixture was purified by preparative HPLC (Column: Sunfire prep C18 column, 30×150 mm, 5 um; Mobile Phase A: Water (0.1% $HCO_2H$), Mobile Phase B: ACN; Flow rate: 60 mL/min; Gradient: 10 B to 35 B in 8 min; 254/220 nm; RT: 7.37. Fractions containing the desired compound were evaporated to dryness to afford 5-[4-[(2-ethyl-7-fluoro-3-oxo-4H-quinoxalin-6-yl)methyl]piperazin-1-yl]-6-fluoro-N-methyl-pyridine-2-carboxamide (Example 21, 55.0 mg, 53.7%) as an off-white solid. $^{1}$H NMR(400 MHz, DMSO-$d_6$) δ 1.21 (3H, t), 2.61 (4H, m), 2.73-2.85 (5H, m), 3.18 (4H, m), 3.68 (2H, s), 7.38 (1H, d), 7.51-7.61 (2H, m), 7.84 (1H, dd), 8.13 (0.29H, s), 8.38 (1H, m), 12.29 (1H, s); $^{19}$F NMR (376 MHz, DMSO-$d_6$) δ-72.53, -124.31; m/z (ES+) $[M+H]^+$=443.

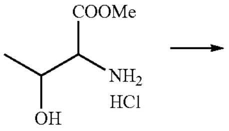

Intermediate 66

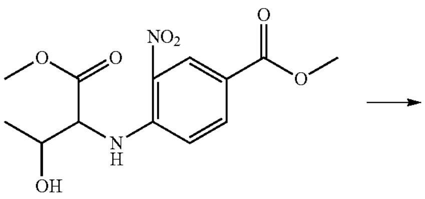

Intermediate 67

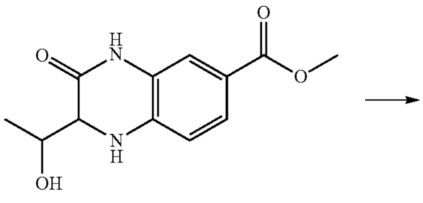

Intermediate 68

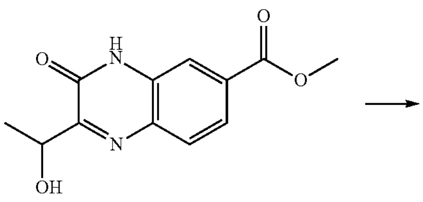

Intermediate 69

-continued

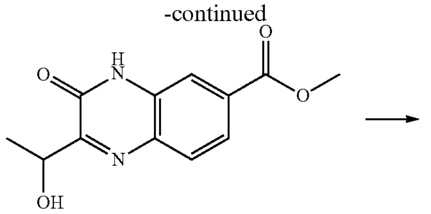

Intermediate 70

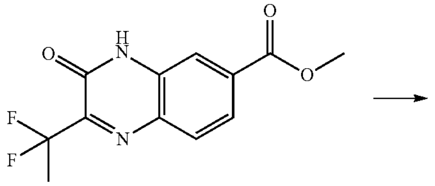

Intermediate 71

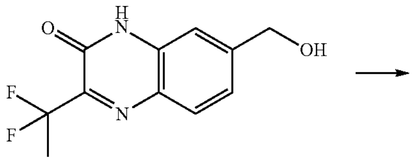

Intermediate 72

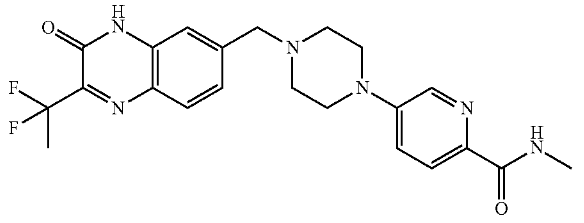

Example 22

Intermediate 67: Methyl 4-(3-hydroxy-1-methoxy-1-oxobutan-2-ylamino)-3-nitrobenzoate DIPEA (8.77 mL, 50.22 mmol) was added to methyl 4-fluoro-3-nitrobenzoate (2.0 g, 10.04 mmol) and methyl 2-amino-3-hydroxybutanoate hydrochloride (Intermediate 66, 2.04 g, 12.05 mmol) in DMF (20 mL). The resulting mixture was stirred at rt for 16 hours. The reaction mixture was diluted with EtOAc (100 mL), and washed sequentially with saturated aqueous $NH_4Cl$ solution (100 mL×1), and brine (100 mL×4). The organic layer was dried over $Na_2SO_4$, filtered and evaporated to afford desired product, methyl 4-((3-hydroxy-1-methoxy-1-oxobutan-2-yl)amino)-3-nitrobenzoate (Intermediate 67, 2.9 g, 92%), as a yellow solid. $1_{H\ NMR}$ (400 MHz, DMSO-$d_6$) δ 1.15-1.27 (3H, m), 3.64-3.74 (3H, m), 3.83 (3H, s), 4.08-4.44 (1H, m), 4.61-4.72 (1H, m), 5.39-5.60 (1H, m), 7.03-7.15 (1H, m), 7.90-8.03 (1H, m), 8.62-8.69 (1H, m), 8.73-8.89 (1H, m); m/z (ES+) $[M+H]^+$=313.

Intermediate 68: Methyl 2-(1-hydroxyethyl)-3-oxo-1,2,3,4-tetrahydroquinoxaline-6-carboxylate 20% $Pd(OH)_2$/C (0.648 g, 0.92 mmol) was added to methyl 4-((3-hydroxy-1-methoxy-1-oxobutan-2-yl)amino)-3-nitrobenzoate (Intermediate 67, 2.88 g, 9.22 mmol) in MeOH (300 mL) under hydrogen. The resulting mixture was stirred at room temperature for 16 hours. The reaction went to completion. The reaction mixture was filtered through celite. The organic layer was evaporated to afford methyl 2-(1-hydroxyethyl)-3-oxo-1,2,3,4-tetrahydroquinoxaline-6-carboxylate (Intermediate 68, 2.290 g, 99%) as a grey solid. $^1$H NMR (400 MHz, DMSO-$d_6$) δ 1.07 (3H, m), 2.81 (1H, d), 3.72 (1H, m), 3.74 (3H, s), 4.78 (1H, d), 6.70-6.86 (2H, m), 7.27 (1H, d), 7.37 (1H, dd), 10.38 (1H, d); m/z ($ES^+$) $[M+H]^+$=251.

Intermediate 69: Methyl 2-(1-hydroxyethyl)-3-oxo-3,4-dihydroquinoxaline-6-carboxylate DDQ (2.265 g, 9.98 mmol) was added to methyl 2-(1-hydroxyethyl)-3-oxo-1,2,3,4-tetrahydroquinoxaline-6-carboxylate (Intermediate 68, 2.27 g, 9.07 mmol) in DCM (100 mL). The resulting mixture was stirred at room temperature for 1 hour. The reaction went to completion. The reaction mixture was concentrated under reduced pressure to obtain a brown solid. Aq $NaHCO_3$ saturated solution (100 mL) was added to the solid and stirred at room temperature for 1 hour. The precipitate was filtered and rinsed with additional aq $NaHCO_3$ solution (30 mL×3). The solid was dried under vacuum to afford methyl 2-(1-hydroxyethyl)-3-oxo-3,4-dihydroquinoxaline-6-carboxylate (Intermediate 69, 2.24 g, 99%) as a grey solid. $^1$H NMR (400 MHz, DMSO-$d_6$) δ 1.40 (3H, d), 3.88 (3H, s), 4.94 (1H, q), 7.69 (1H, dd), 7.77 (1H, d), 7.90 (1H, d) (2 protons are not shown); m/z ($ES^+$) $[M+H]^+$=249.

Intermediate 70: Methyl 2-acetyl-3-oxo-3,4-dihydroquinoxaline-6-carboxylate

Dess-martin periodinane (2.56 g, 6.04 mmol) was added to methyl 2-(1-hydroxyethyl)-3-oxo-3,4-dihydroquinoxaline-6-carboxylate (Intermediate 69, 1.0 g, 4.03 mmol) in DCM (30 mL). The resulting mixture was stirred at room temperature for 3 hours. The reaction mixture was evaporated to afford the crude product. The crude product was purified by reverse phase chromatography, elution gradient 5 to 30% MeCN in water (0.4% $HCO_2H$). Pure fractions were evaporated to dryness to afford methyl 2-cetyl-3-oxo-3,4-dihydroquinoxaline-6-carboxylate (Intermediate 70, 0.62 g, 62.5%) as a pale yellow solid. $^1$H NMR (400 MHz, DMSO-$d_6$) δ 2.58 (3H, s), 3.91 (3H, s), 7.84 (1H, dd), 7.91-8.03 (2H, m), 12.86 (1H, s); m/z ($ES^+$) $[M+H]^+$=247.

Intermediate 71: Methyl 2-(1,1-difluoroethyl)-3-oxo-3,4-dihydroquinoxaline-6-carboxvlate BAST (1.35 mL, 7.31 mmol) was added to methyl 2-acetyl-3-oxo-3,4-dihydroquinoxaline-6-carboxylate (Intermediate 70, 600 mg, 2.44 mmol) in DCM (20 mL). The resulting mixture was stirred at room temperature for 16 hours. The reaction mixture was evaporated to afford crude product. The crude product was purified by reverse phase chromatography, elution gradient 5 to 30% MeCN in water (0.4% $HCO_2H$). Pure fractions were evaporated to dryness to afford methyl 2-(1,1-difluoroethyl)-3-oxo-3,4-dihydroquinoxaline-6-carboxylate (Intermediate 71, 174 mg, 26.6%) as an off-white solid. $^1$H NMR (400 MHz, DMSO-$d_6$) δ 2.07 (3H, t), 3.91 (3H, s), 7.84 (1H, dd), 7.92-7.99 (2H, m), 12.90 (1H, s); $19_F$ NMR (376 MHz, DMSO-$d_6$) δ-93.26; m/z ($ES^+$) $[M+H]^+$=269.

Intermediate 72: 3-(1,1-difluoroethyl)-7-(hydroxymethyl)quinoxalin-2(1H)-one

A solution of 1 M diisobutylaluminum hydride in THF (2.39 mL, 2.39 mmol) was added to methyl 2-(1,1-difluoroethyl)-3-oxo-3,4-dihydroquinoxaline-6-carboxylate (Intermediate 71, 160 mg, 0.60 mmol) in THF (50 mL) at 0° C. The resulting mixture was stirred at room temperature for 16 hours. The reaction mixture was quenched with saturated potassium sodium tartrate aqueous solution (3 mL) and MeOH (1 mL) at 0° C. The resulting mixture was stirred for 1 hour. The reaction mixture was filtered and washed with THF (10 mL×3). The organic layer was evaporated to afford crude product, 3-(1,1-difluoroethyl)-7-(hydroxymethyl)quinoxalin-2(1H)-one (Intermediate 72, 120 mg, 84%). The product was used in the next step directly without further purification. $^1$H NMR (400 MHz, DMSO-$d_6$) δ 2.06 (3H, t), 4.63 (2H, s), 5.47 (1H, s), 7.26 (1H, dd), 7.35 (1H, d), 7.78 (1H, d), 12.75 (1H, br s); m/z (ES+) $[M+H]^+$=241.

Example 22: 5-[4-[[2-(1,1-difluoroethyl)-3-oxo-4H-quinoxalin-6-yl]methyl]piperazin-1-yl]-N-methyl-pyridine-2-carboxamide

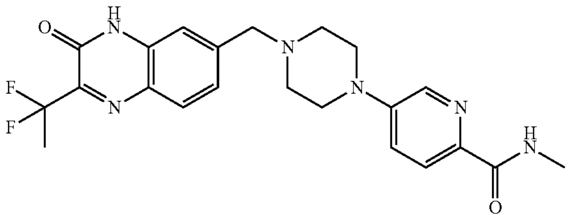 [SMILES: CNC(=O)c1ccc(N2CCN(Cc3ccc4nc(C(C)(F)F)c(=O)[nH]c4c3)CC2)cn1]

3-(1,1-difluoroethyl)-7-(hydroxymethyl)quinoxalin-2(1H)-one (Intermediate 72, 60 mg, 0.25 mmol) was added to 33% HBr in acetic acid (2 mL, 12.15 mmol). The resulting mixture was stirred at 80° C. for 2 hours. The reaction mixture was evaporated under vacuum to afford 7-(bromomethyl)-3-(1,1-difluoroethyl)quinoxalin-2(1H)-one (crude product). The product was used in the next step directly without further purification. DIPEA (0.218 mL, 1.25 mmol) was added to 7-(bromomethyl)-3-(1,1-difluoroethyl)quinoxalin-2(1H)-one (crude product) and N-methyl-5-(piperazin-1-yl)picolinamide (Intermediate 13, 60 mg, 0.27 mmol) in NMP (3 mL). The resulting mixture was stirred at 80° C. for 1 hour. The reaction mixture was concentrated and purified by preparative HPLC (Column: XBridge Shield RP18 OBD Column, 30×150 mm, 5 um; Mobile Phase A: Water (0.05% $NH_3H_2O$), Mobile Phase B: ACN; Flow rate: 60 mL/min; Gradient: 13 B to 33 B in 7 min; 254; 220 nm; RT: 5.70. Fractions containing the desired compound were evaporated to dryness to afford 5-[4-[[2-(1,1-difluoroethyl)-3-oxo-4H-quinoxalin-6-yl]methyl]piperazin-1-yl]-N-methyl-pyridine-2-carboxamide (Example 22, 47.8 mg, 43.2%) as an yellow solid. $^1$H NMR (400 MHz, DMSO-$d_6$) δ 2.06 (3H, t), 2.52-2.62 (4H, m), 2.78 (3H, d), 3.30-3.40 (4H, m), 3.67 (2H, s), 7.32-7.42 (3H, m), 7.80-7.86 (2H, m), 8.27 (1H, d), 8.34-8.42 (1H, m), 12.70 (1H, s); $^{19}$F NMR (376 MHz, DMSO-$d_6$) δ-92.74; m/z ($ES^+$) $[M+H]^+$=443.

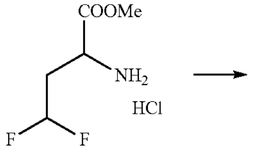

Intermediate 73

-continued

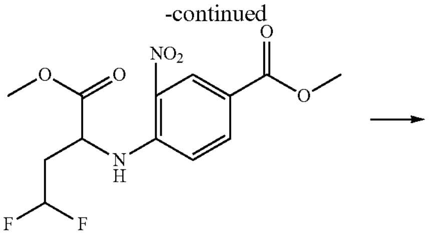

Intermediate 74

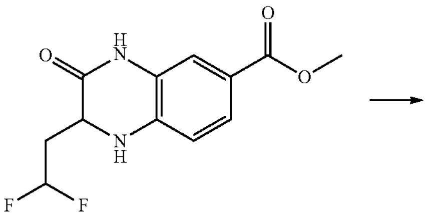

Intermediate 75

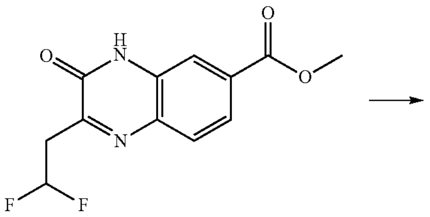

Intermediate 76

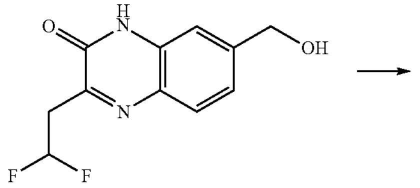

Intermediate 77

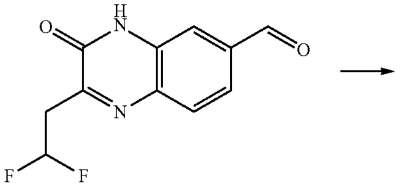

Intermediate 78

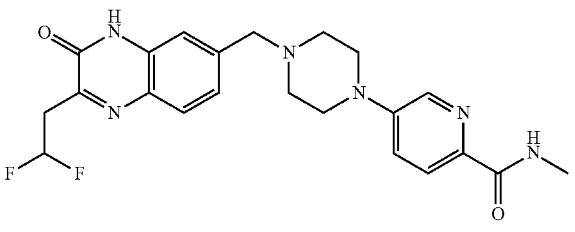

Example 23

Intermediate 74: Methyl 4-(4,4-difluoro-1-methoxy-1-oxobutan-2-ylamino)-3-nitrobenzoate DIPEA (8.77 mL, 50.22 mmol) was added to methyl 4-fluoro-3-nitrobenzoate (2.0 g, 10.04 mmol) and methyl 2-amino-4,4-difluorobutanoate hydrochloride (Intermediate 73, 2.0 g, 10.55 mmol) in DMF (20 mL). The resulting mixture was stirred at 40° C. for 8 hours. The reaction mixture was diluted with EtOAc (100 mL), and washed sequentially with saturated $NH_4Cl$ (100 mL×1), and brine (100 mL×4). The organic layer was dried over $Na_2SO_4$, filtered and evaporated to afford desired product, methyl 4-((4,4-difluoro-1-methoxy-1-oxobutan-2-yl)amino)-3-nitrobenzoate (Intermediate 74, 2.5 g, 74.9%), as a yellow solid. $^1$H NMR (300 MHz, DMSO-$d_6$) δ 2.50-2.76 (2H, m), 3.71 (3H, s), 3.82 (3H, s), 4.95 (1H, q), 6.22 (1H, tt), 7.18 (1H, d), 7.99 (1H, dd), 8.63 (1H, d), 8.66 (1H, d); m/z (ES+) $[M+H]^+$=333.

Intermediate 75: Methyl 2-(2,2-difluoroethyl)-3-oxo-1,2,3,4-tetrahydroquinoxaline-6-carboxylate 20% $Pd(OH)_2$/C (0.465 g, 0.66 mmol) was added to methyl 4-((4,4-difluoro-1-methoxy-1-oxobutan-2-yl)amino)-3-nitrobenzoate (Intermediate 74, 2.2 g, 6.62 mmol) in MeOH (300 mL) under hydrogen. The resulting mixture was stirred at room temperature for 16 hours. The reaction mixture was filtered through celite. The filtrate was evaporated to afford methyl 2-(2,2-difluoroethyl)-3-oxo-1,2,3,4-tetrahydroquinoxaline-6-carboxylate (Intermediate 75, 1.64 g, 92%) as a yellow solid. $^1$H NMR (400 MHz, DMSO-$d_6$) δ 2.24-2.32 (2H, m), 3.76 (3H, s), 4.10-4.18 (1H, m), 6.27 (1H, tt), 6.73 (1H, d), 6.89 (1H, s), 7.37 (1H, d), 7.44 (1H, dd), 10.58 (1H, s); m/z (ES$^+$) $[M+H]^+$=271.

Intermediate 76: Methyl 2-(2,2-difluoroethyl)-3-oxo-3,4-dihydroquinoxaline-6-carboxylate DDQ (1.478 g, 6.51 mmol) was added to methyl 2-(2,2-difluoroethyl)-3-oxo-1,2,3,4-tetrahydroquinoxaline-6-carboxylate (Intermediate 75, 1.6 g, 5.92 mmol) in DCM (100 mL). The resulting mixture was stirred at room temperature for 3 hours. The resulting mixture was removed under reduced pressure to obtain a brown solid. Aq $NaHCO_3$ saturated solution (100 mL) was added to the solid and stirred at room temperature for 1 hour. The precipitate was filtered and rinsed with additional aq $NaHCO_3$ solution (30 mL×3).The solid was dried under vacuum to afford methyl 2-(2,2-difluoroethyl)-3-oxo-3,4-dihydroquinoxaline-6-carboxylate (Intermediate 76, 1.58 g, 99%) as an off-white solid. $^1$H NMR (400 MHz, DMSO-$d_6$) δ 3.46 (2H, td), 3.90 (3H, s), 6.57 (1H, t), 7.79-7.92 (3H, m), 12.68 (1H, s); m/z (ES$^+$) $[M+H]^+$=269.

Intermediate 77: 3-(2,2-difluoroethyl)-7-(hydroxymethyl)quinoxalin-2(1H)-one

A 1 M solution of diisobutylaluminum hydride in THF (22.37 mL, 22.37 mmol) was added portionwise to methyl 2-(2,2-difluoroethyl)-3-oxo-3,4-dihydroquinoxaline-6-carboxylate (Intermediate 76, 1.0 g, 3.73 mmol) in THF (100 mL) at 0° C. The resulting mixture was stirred at room temperature for 16 hours. The reaction mixture was quenched with saturated potassium sodium tartrate aqueous solution (20 mL) and MeOH (10 mL) at 0° C. The resulting mixture was stirred for 1 hour. The reaction mixture was filtered and washed with THF (30 mL×3). The organic layer was evaporated to afford 3-(2,2-difluoroethyl)-7-(hydroxymethyl)quinoxalin-2(1H)-one (0.72 g, 80%) as a red solid (crude product). The crude product was purified by reverse phase chromatography, elution gradient 5 to 60% MeOH in water (0.4% $HCO_2H$). Pure fractions were evaporated to dryness to afford 3-(2,2-difluoroethyl)-7-(hydroxymethyl)quinoxalin-2(1H)-one (Intermediate 77, 500 mg, 69.4%) as a red solid. $^1$H NMR (300 MHz, DMSO-$d_6$) δ 3.42 (2H, td), 4.61 (2H, s), 5.42 (1H, brs), 6.56 (1H, tt), 7.23 (1H, dd), 7.32 (1H, d), 7.71 (1H, d), 12.55 (1H, s); m/z (ES+) $[M+H]^+$=241.

Intermediate 78: 2-(2,2-difluoroethyl)-3-oxo-3,4-dihydroquinoxaline-6-carbaldehyde Dess-Martin periodinane (530 mg, 1.25 mmol) was added to 3-(2,2-difluoroethyl)-7-(hydroxymethyl)quinoxalin-2(1H)-one (Intermediate 77, 200 mg, 0.83 mmol) in DCM (5 mL). The resulting mixture was stirred at room temperature for 2 hours. The resulting mixture was evaporated to afford crude product. The crude product was purified by reverse phase chromatography, elution gradient 5 to 30% MeCN in water (0.4% $HCO_2H$). Pure fractions were evaporated to dryness to afford 2-(2,2-difluoroethyl)-3-oxo-3,4-dihydroquinoxaline-6-carbaldehyde (Intermediate 78, 160 mg, 81%) as a yellow solid. $^1$H NMR (400 MHz, DMSO-$d_6$) δ 3.47 (2H, td), 6.58 (1H, tt), 7.77-7.85 (2H, m), 7.90-7.98 (1H, m), 10.09 (1H, s), 12.79 (1H, s); m/z (ES$^+$) $[M+H]^+$=239.

Example 23: 5-[4-[[2-(2,2-difluoroethyl)-3-oxo-4H-quinoxalin-6-yl]methyl]piperazin-1-yl]-N-methyl-pyridine-2-carboxamide

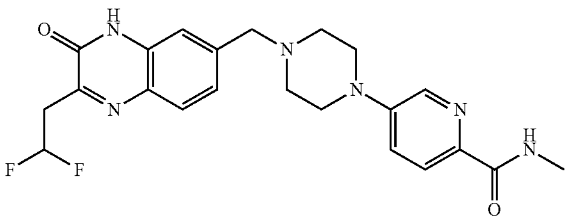 [SMILES: CNC(=O)c1ccc(N2CCN(Cc3ccc4nc(CC(F)F)c(=O)[nH]c4c3)CC2)cn1]

Titanium isopropoxide (65.6 mg, 0.23 mmol) was added to 2-(2,2-difluoroethyl)-3-oxo-3,4-dihydroquinoxaline-6-carbaldehyde (Intermediate 78, 55 mg, 0.23 mmol) and N-methyl-5-(piperazin-1-yl)picolinamide (Intermediate 13, 60 mg, 0.23 mmol) in THF (2 mL). The resulting mixture was stirred at room temperature for 2 minutes. Sodium triacetoxyborohydride (196 mg, 0.92 mmol) was added. The resulting mixture was stirred at room temperature for 1 hour. The reaction mixture was quenched with MeOH (0.1 mL). The reaction mixture was evaporated to afford crude product which was purified by preparative HPLC (Column: XBridge Shield RP18 OBD Column, 30×150 mm, 5 um; Mobile Phase A: Water (0.05% $NH_3H_2O$), Mobile Phase B: ACN; Flow rate: 60 mL/min; Gradient: 13 B to 33 B in 7 min; 254; 220 nm; RT: 5.70. Fractions containing the desired compound were evaporated to dryness to afford 5-[4-[[2-(2,2-difluoroethyl)-3-oxo-4H-quinoxalin-6-yl]methyl]piperazin-1-yl]-N-methyl-pyridine-2-carboxamide (Example 23, 8.76 mg, 8.57%) as a yellow solid. $^1$H NMR (400 MHz, DMSO-$d_6$) δ 2.56 (4H, m), 2.78 (3H, d), 3.32-3.48 (6H, m), 3.64 (2H, s), 6.55 (1H, tt), 7.27-7.33 (2H, m), 7.39 (1H, dd), 7.73 (1H, d), 7.83 (1H, d), 8.26 (1H, d), 8.37 (1H, m), 12.49 (1H, s); $^{19}$F NMR (376 MHz, DMSO-$d_6$) δ-114.29; m/z (ES$^+$) $[M+H]^+$=443.

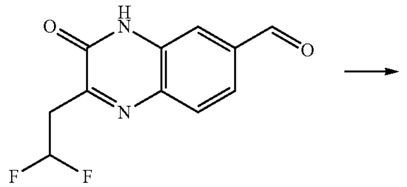

Intermediate 78

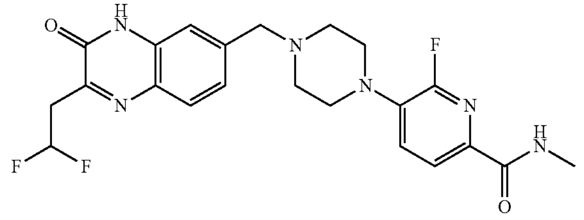 [SMILES: CNC(=O)c1ccc(N2CCN(Cc3ccc4nc(CC(F)F)c(=O)[nH]c4c3)CC2)c(F)n1]

Example 24

Example 24: 5-[4-[[2-(2,2-difluoroethyl)-3-oxo-4H-quinoxalin-6-yl]methyl]piperazin-1-yl]-6-fluoro-N-methyl-pyridine-2-carboxamide

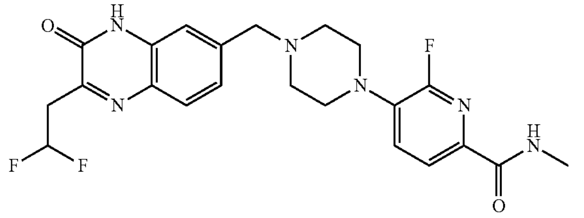

Titanium isopropoxide (59.7 mg, 0.21 mmol) was added to 2-(2,2-difluoroethyl)-3-oxo-3,4-dihydroquinoxaline-6-carbaldehyde (Intermediate 78, 50 mg, 0.21 mmol) and 6-fluoro-N-methyl-5-(piperazin-1-yl)picolinamide (Intermediate 23, 50.0 mg, 0.21 mmol) in THF (2 mL). The resulting mixture was stirred at room temperature for 2 minutes. Sodium triacetoxyborohydride (178 mg, 0.84 mmol) was added. The resulting mixture was stirred at room temperature for 1 hour. The reaction went to completion. The reaction mixture was quenched with MeOH (0.1 mL). The reaction mixture was evaporated to afford crude product. The crude product was purified by preparative HPLC (Column: Sunfire prep C18 column, 30×150, 5 um; Mobile Phase A: Water (0.1% $HCO_2H$), Mobile Phase B: ACN; Flow rate: 60 mL/min; Gradient: 2 B to 27 B in 7 min; 254/220 nm; RT: 6.78. Fractions containing the desired compound were evaporated to dryness to afford 5-[4-[[2-(2,2-difluoroethyl)-3-oxo-4H-quinoxalin-6-yl]methyl]piperazin-1-yl]-6-fluoro-N-methyl-pyridine-2-carboxamide (Example 24, 21.72 mg, 22.13%) as a yellow solid. $1^H$ NMR (400 MHz, DMSO-$d_6$) δ 2.54-2.61 (4H, m), 2.76 (3H, d), 3.14 3.22 (4H, m), 3.41 (2H, td), 3.64 (2H, s), 6.39-6.71 (1H, m), 7.26-7.33 (2H, m), 7.57 (1H, dd), 7.73 (1H, d), 7.82-7.86 (1H, m), 8.13 (0.16H, s), 8.37 (1H, m), 12.49 (1H, s); $^{19}F$ NMR (376 MHz, DMSO-$d_6$) δ-72.52, -114.29; m/z ($ES^+$) $[M+H]^+$=461.

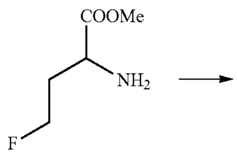

Intermediate 79

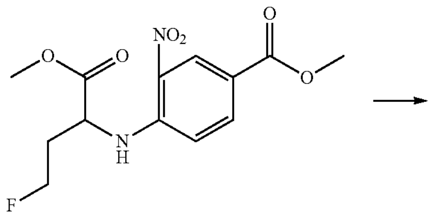

Intermediate 80

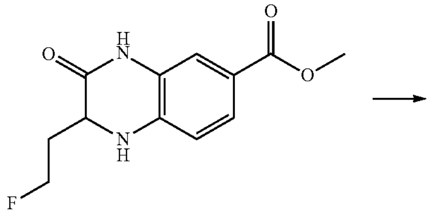

Intermediate 81

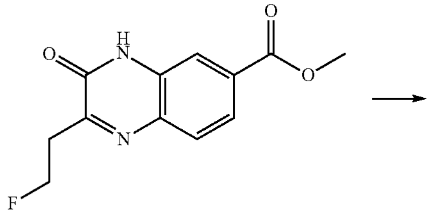

Intermediate 82

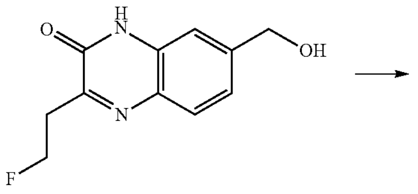

Intermediate 83

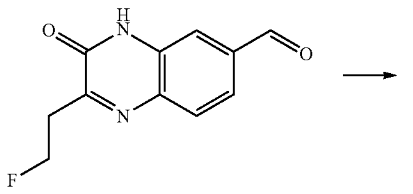

Intermediate 84

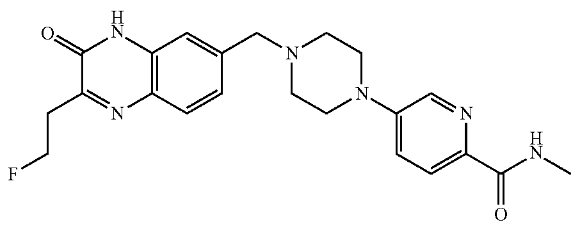

Example 25

Intermediate 80: Methyl 4-(4-fluoro-1-methoxy-1-oxobutan-2-ylamino)-3-nitrobenzoate DIPEA (8.77 mL, 50.22 mmol) was added to methyl 4-fluoro-3-nitrobenzoate (2.0 g, 10.04 mmol) and methyl 2-amino-4-fluorobutanoate hydrochloride (Intermediate 79, 1.81 g, 10.55 mmol) in DMF (20 mL). The resulting mixture was stirred at 40° C. for 8 hours. The reaction mixture was diluted with EtOAc (100 mL), and washed sequentially with saturated $NH_4Cl$ (100 mL×1), and brine (100 mL×4). The organic layer was dried over $Na_2SO_4$, filtered and evaporated to afford desired product, methyl 4-((4-fluoro-1-methoxy-1-oxobutan-2-yl)amino)-3-nitrobenzoate (Intermediate 80, 2.5 g, 79%), as a yellow solid. $^1H$ NMR (300 MHz, DMSO-$d_6$) δ 2.25-2.35 (1H, m), 2.35-2.45 (1H, m), 3.71 (3H, s), 3.82 (3H, s), 4.36-4.58 (1H, m), 4.56-4.74 (1H, m), 4.84 (1H, q), 7.14 (1H, d), 7.99 (1H, dd), 8.63 (1H, d), 8.67 (1H, d); m/z (ES+) [M+H]+=315.

Intermediate 81: Methyl 2-(2-fluoroethyl)-3-oxo-1,2,3,4-tetrahydroquinoxaline-6-carboxylate 20% $Pd(OH)_2/C$ (0.547 g, 0.78 mmol) was added to methyl 4-((4-fluoro-1-methoxy-1-oxobutan-2-yl)amino)-3-nitrobenzoate (Intermediate 80, 2.45 g, 7.80 mmol) in MeOH (300 mL) under hydrogen. The resulting mixture was stirred at room temperature for 16 hours. The reaction went to completion. The reaction mixture was filtered through celite. The filtrate was evaporated to afford methyl 2-(2-fluoroethyl)-3-oxo-1,2,3,4-tetrahydroquinoxaline-6-carboxylate (Intermediate 81, 1.9 g, 97%) as a grey solid. $^1H$ NMR (400 MHz, DMSO-$d_6$) δ1.91-2.19 (2H, m), 3.75 (3H, s), 4.03 (1H, m), 4.49-4.73 (2H, m), 6.73 (1H, d), 6.91 (1H, d), 7.35 (1H, d), 7.42 (1 H, dd), 10.46 (1H, s); m/z ($ES^+$) $[M+H]^+$=253.

Intermediate 82: Methyl 2-(2-fluoroethyl)-3-oxo-3,4-dihydroquinoxaline-6-carboxylate DDQ (1.83 g, 8.07 mmol) was added to methyl 2-(2-fluoroethyl)-3-oxo-1,2,3,4-tetrahydroquinoxaline-6-carboxylate (Intermediate 81, 1.85 g, 7.33 mmol) in DCM (100 mL). The resulting mixture was stirred at room temperature for 3 hours. The resulting mixture was removed under reduced pressure to obtain a brown solid. Aq. $NaHCO_3$ saturated solution (100 mL) was added to the solid and stirred at room temperature for 1 hour. The precipitate was filtered and rinsed with additional aq $NaHCO_3$ solution (30 mL×3). The solid was dried under vacuum to afford methyl 2-(2-fluoroethyl)-3-oxo-3,4-dihydroquinoxaline-6-carboxylate (Intermediate 82, 1.8 g, 98%) as a grey solid. $^1H$ NMR (400 MHz, DMSO-$d_6$) δ 3.23 (2H, dt), 3.89 (3H, s), 4.90 (2H, dt), 7.76-7.85 (2H, m), 7.88 (1H, d), 12.55 (1H, s); m/z ($ES^+$) $[M+H]^+$=251.

Intermediate 83: 3-(2-fluoroethyl)-7-(hydroxvmethvhquinoxalin-2(1H)-one

1 M solution of diisobutylaluminum hydride in THF (15.99 mL, 15.99 mmol) was added portionwise to methyl 2-(2-fluoroethyl)-3-oxo-3,4-dihydroquinoxaline-6-carboxylate (Intermediate 82, 1.0 g, 4.00 mmol) in THF (100 mL) at 0° C. The resulting mixture was stirred at room temperature for 16 hours. The reaction mixture was quenched with saturated potassium sodium tartrate aqueous solution (20 mL) and MeOH (10 mL) at 0° C. The resulting mixture was stirred for 1 hour. The reaction mixture was filtered and washed with THF (30 mL×3). The organic layer was evaporated to afford crude product. The crude product was purified by reverse phase chromatography, elution gradient 5 to 60% MeOH in water (0.4% $HCO_2H$). Pure fractions were evaporated to dryness to afford 3-(2-fluoroethyl)-7-(hydroxymethyl)quinoxalin-2(1H)-one (Intermediate 83, 0.49 g, 55.2%) as a brown solid. $^1H$ NMR (300 MHz, DMSO-$d_6$) δ 3.20 (2H, dt), 4.60 (2H, d), 4.90 (2H, dt), 5.41 (1H, t), 7.21 (1H, dd), 7.30 (1H, d), 7.68 (1H, d), 12.42 (1H, s); m/z (ES+) $[M+H]^+$=223.

Intermediate 84: 2-(2-fluoroethyl)-3-oxo-3,4-dihydroquinoxaline-6-carbaldehyde

Dess-Martin periodinane (229 mg, 0.54 mmol) was added to 3-(2-fluoroethyl)-7-(hydroxymethyl)quinoxalin-2(1H)-one (Intermediate 83, 100 mg, 0.45 mmol) in DCM (3 mL). The resulting mixture was stirred at room temperature for 2 hours. The reaction mixture was evaporated to afford crude product. The crude product was purified by reverse phase chromatography, elution gradient 5 to 30% MeCN in water (0.4% $HCO_2H$). Pure fractions were evaporated to dryness to afford 2-(2-fluoroethyl)-3-oxo-3,4-dihydroquinoxaline-6-carbaldehyde (Intermediate 84, 93 mg, 94%) as a yellow solid. $^1H$ NMR (300 MHz, DMSO-$d_6$) δ 3.20-3.28 (2H, m), 4.90 (2H, dt), 7.74-7.80 (2H, m), 7.91 (1H, d), 10.06 (1H, s), 12.66 (1H, s); m/z (ES+) $[M+H]^+$=221.

Example 25: 5-[4-[[2-(2-fluoroethyl)-3-oxo-4H-quinoxalin-6-yl]methyl]piperazin-1-yl]-N-methyl-pyridine-2-carboxamide

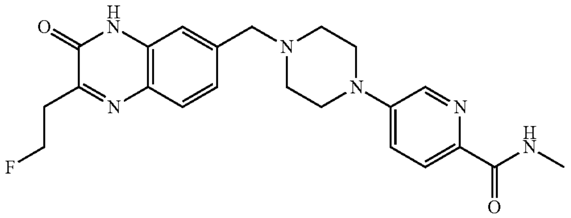 [SMILES: CNC(=O)c1ccc(N2CCN(Cc3ccc4nc(CCF)c(=O)[nH]c4c3)CC2)cn1]

Titanium isopropoxide (64.5 mg, 0.23 mmol) was added to 2-(2-fluoroethyl)-3-oxo-3,4-dihydroquinoxaline-6-carbaldehyde (Intermediate 84, 50 mg, 0.23 mmol) and N-methyl-5-(piperazin-1-yl)picolinamide (Intermediate 13, 50.0 mg, 0.23 mmol) in THF (3 mL). The resulting mixture was stirred at room temperature for 2 minutes. Sodium triacetoxyborohydride (192 mg, 0.91 mmol) was added. The resulting mixture was stirred at room temperature for 2 hours. This was repeated in another batch, and two batches were combined for the purification. The combined reaction mixture was purified by preparative HPLC (Column: XBridge Prep OBD C18 Column, 30×150mm 5 um; Mobile Phase A: Water (10 MMOL/L $NH_4HCO_3$), Mobile Phase B: ACN; Flow rate: 60 mL/min; Gradient: 20 B to 35 B in 7 min; 254/210 nm; RT: 6.38. Fractions containing the desired compound were evaporated to dryness to afford 5-[4-[[2-(2-fluoroethyl)-3-oxo-4H-quinoxalin-6-yl]methyl]piperazin-1-yl]-N-methyl-pyridine-2-carboxamide (Example 25, 4.83 mg, 2.54%) as a white solid. $^1H$ NMR (400 MHz, DMSO-$d_6$) δ 2.53-2.59 (4H, m), 2.78 (3H, d), 3.17 (1H, t), 3.23 (1H, t), 3.32-3.38 (4H, m), 3.63 (2H, s), 4.83 (1H, t), 4.95 (1H, t), 7.25-7.32 (2H, m), 7.39 (1H, dd), 7.71 (1H, d), 7.83 (1H, d), 8.26 (1H, d), 8.37 (1H, d), 12.36 (1H, s); $^{19}$F NMR (376 MHz, DMSO-$d_6$) δ-217.70; m/z (ES$^+$) [M+H]$^+$=425.

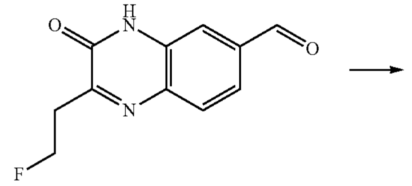

Intermediate 84

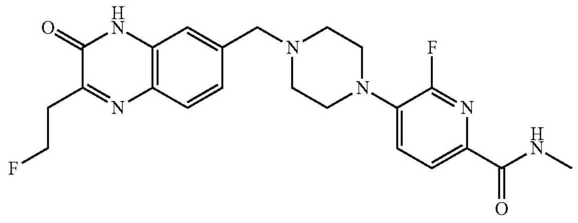 [SMILES: CNC(=O)c1ccc(N2CCN(Cc3ccc4nc(CCF)c(=O)[nH]c4c3)CC2)c(F)n1]

Example 26

Example 26: 6-fluoro-5-[4-[[2-(2-fluoroethyl)-3-oxo-4H-quinoxalin-6-yl]methyl]piperazin-1-yl]-N-methyl-pyridine-2-carboxamide

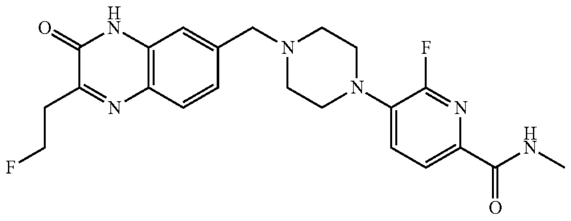

Titanium isopropoxide (90 mg, 0.32 mmol) was added to 2-(2-fluoroethyl)-3-oxo-3,4-dihydroquinoxaline-6-carbaldehyde (Intermediate 84, 70 mg, 0.32 mmol) and 6-fluoro-N-methyl-5-(piperazin-1-yl)picolinamide (Intermediate 23, 76 mg, 0.32 mmol) in THF (3 mL). The resulting mixture was stirred at room temperature for 2 minutes. Sodium triacetoxyborohydride (269 mg, 1.27 mmol) was added. The resulting mixture was stirred at room temperature for 1 hour. The reaction mixture was quenched with MeOH (0.1 mL). The reaction mixture was evaporated to afford crude product. The crude product was purified by preparative HPLC (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 28 B to 35 B in 8 min; 254/210 nm; RT: 7 Fractions containing the desired compound were evaporated to dryness to afford crude product. The crude product was further purified by preparative HPLC (Column: Xselect CSH OBD Column 30*150 mm 5 um, n; Mobile Phase A: Water (0.1% $HCO_2H$), Mobile Phase B: ACN; Flow rate: 60 mL/min; Gradient: 5 B to 20 B in 7 min; 254; 220 nm; RT: 6.83. Fractions containing the desired compound were evaporated to dryness to afford 6-fluoro-5-[4-[[2-(2-fluoroethyl)-3-oxo-4H-quinoxalin-6-yl]methyl]piperazin-1-yl]-N-methyl-pyridine-2-carboxamide (Example 26, 3.79 mg, 2.65%) as a yellow solid. $^1$H NMR (400 MHz, DMSO-$d_6$) δ 2.55-2.60 (4H, m), 2.76 (3H, d), 3.14 3.25 (6H, m), 3.63 (2H, s), 4.89 (2H, dt), 7.24-7.31 (2H, m), 7.57 (1H, dd), 7.70 (1H, d), 7.84 (1H, d), 8.24 (0.174H, s), 8.38 (1H, d), 12.37 (1H, s); $^{19}$F NMR (376 MHz, DMSO-$d_6$) δ-72.51, -217.71; (ES$^+$) [M+H]$^+$=443.

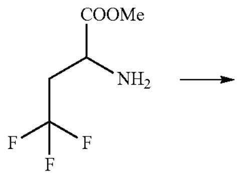

Intermediate 85

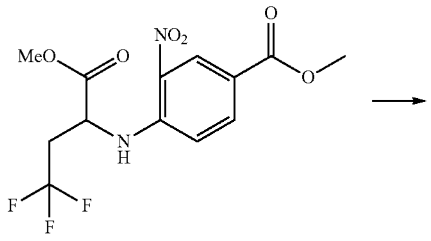

Intermediate 86

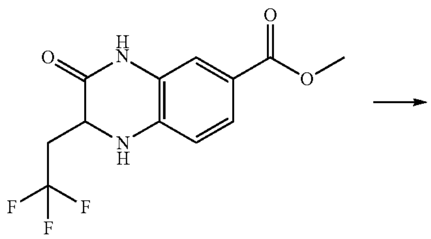

Intermediate 87

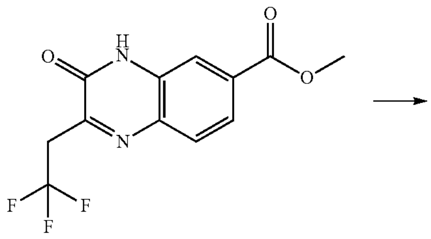

Intermediate 88

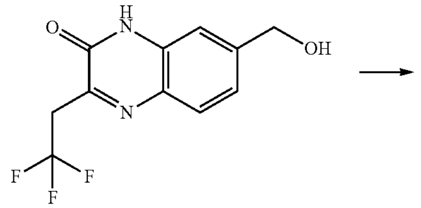

Intermediate 89

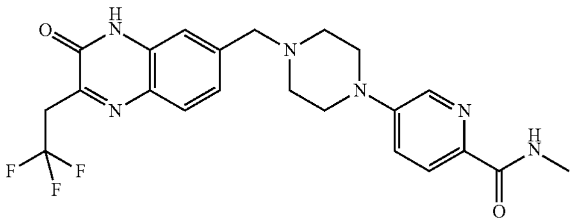

Example 27

Intermediate 86: Methyl 3-nitro-4-(4,4,4-trifluoro-1-methoxy-1-oxobutan-2-ylamino)benzoate DIPEA (8.77 mL, 50.22 mmol) was added to methyl 4-fluoro-3-nitrobenzoate (2.0 g, 10.04 mmol) and methyl 2-amino-4,4,4-trifluorobutanoate hydrochloride (Intermediate 85, 2.2 g, 10.55 mmol) in DMF (20 mL). The resulting mixture was stirred at 50° C. for 10 hours. The reaction mixture was diluted with EtOAc (100 mL), and washed sequentially with saturated aqueous $NH_4Cl$ (100 mL×1), and brine (100 mL×4). The organic layer was dried over $Na_2SO_4$, filtered and evaporated to afford desired product, methyl 3-nitro-4-((4,4,4-trifluoro-1-methoxy-1-oxobutan-2-yl)amino)benzoate (Intermediate 86, 3.0 g, 85%), as a yellow solid. $^1H$ NMR (400 MHz, DMSO-$d_6$) δ 2.99-3.28 (2H, m), 3.73 (3H, s), 3.84 (3H, s), 5.18 (1H, td), 7.28 (1H, d), 8.01 (1H, dd), 8.65 (1H, d), 8.71 (1H, d); m/z ($ES^+$) $[M+H]^+$=351.

Intermediate 87: Methyl 3-oxo-2-(2,2,2-trifluoroethyl)-1,2,3,4-tetrahydroquinoxaline-6-carboxylate 20% $Pd(OH)_2/C$ (0.601 g, 0.86 mmol) was added to methyl 3-nitro-4-((4,4,4-trifluoro-1-methoxy-1-oxobutan-2-yl)amino)benzoate (Intermediate 86, 3.0 g, 8.57 mmol) in MeOH (300 mL) under hydrogen. The resulting mixture was stirred at room temperature for 16 hours. The reaction mixture was filtered through celite. The filtrate was evaporated to dryness to afford methyl 3-oxo-2-(2,2,2-trifluoroethyl)-1,2,3,4-tetrahydroquinoxaline-6-carboxylate (Intermediate 87, 2.3 g, 93%) as an off-white solid. $^1H$ NMR (400 MHz, DMSO-$d_6$) δ 2.64-2.83 (2H, m), 3.76 (3H, s), 4.32-4.37 (1H, m), 6.78 (1H, d), 6.90 (1H, d), 7.37 (1H, d), 7.43 (1H, dd), 10.64 (1H, s); m/z ($ES^+$) $[M+H]^+$=289.

Intermediate 88: Methyl 3-oxo-2-(2,2,2-trifluoroethyl)-3,4-dihydroquinoxaline-6-carboxylate DDQ (1.975 g, 8.70 mmol) was added to methyl 3-oxo-2-(2,2,2-trifluoroethyl)-1,2,3,4-tetrahydroquinoxaline-6-carboxylate (Intermediate 87, 2.28 g, 7.91 mmol) in DCM (100 mL). The resulting mixture was stirred at room temperature for 3 hours. The resulting mixture was removed under reduced pressure to obtain a brown solid. Aq. $NaHCO_3$ saturated solution (100 mL) was added to the solid and stirred at room temperature for 1 hour. The precipitate was filtered and rinsed with additional aq $NaHCO_3$ solution (30 mL×3). The solid was dried under vacuum to afford methyl 3-oxo-2-(2,2,2-trifluoroethyl)-3,4-dihydroquinoxaline-6-carboxylate (Intermediate 88, 2.2 g, 97%) as a brown solid. $1_H$ NMR (400 MHz, DMSO-$d_6$) δ 3.88-3.98 (5H, m), 7.81 (1H, dd), 7.86-7.94 (2H, m), 12.75 (1H, s); m/z ($ES^+$) $[M+H]^+$=287.

Intermediate 89: 7-(hydroxymethyl)-3-(2,2,2-trifluoroethyl)quinoxalin-2(1H)-one

A 1 M solution of diisobutylaluminum hydride in THF (20.96 mL, 20.96 mmol) was added portionwise to methyl 3-oxo-2-(2,2,2-trifluoroethyl)-3,4-dihydroquinoxaline-6-carboxylate (Intermediate 88, 1.0 g, 3.49 mmol) in THF (100 mL) at 0° C. The resulting mixture was stirred at room temperature for 16 hours. The reaction mixture was quenched with saturated potassium sodium tartrate aqueous solution (20 mL) and MeOH (10 mL) at 0° C. The resulting mixture was stirred for 1 hour. The reaction mixture was filtered and washed with THF (30 mL×3). The organic layer was evaporated to afford an off-white solid that was purified by flash silica chromatography, elution gradient 5 to 55% MeOH in water (0.4% $HCO_2H$). Pure fractions were evaporated to dryness to afford 7-(hydroxymethyl)-3-(2,2,2-trifluoroethyl)quinoxalin-2(1H)-one (Intermediate 89, 650 mg, 72.2%) as a yellow solid. $^1H$ NMR (300 MHz, DMSO-$d_6$) δ 3.88 (2 H, q), 4.62 (2H, d), 5.45 (1H, t), 7.24 (1H, dd), 7.33 (1H, d), 7.73 (1H, d), 12.62 (1H, s); m/z ($ES^+$) $[M+H]^+$=259.

Example 27: N-methyl-5-[4-[[3-oxo-2-(2,2,2-trifluoroethyl)-4H-quinoxalin-6-yl]methyl]piperazin-1-yl]pyridine-2-carboxamide

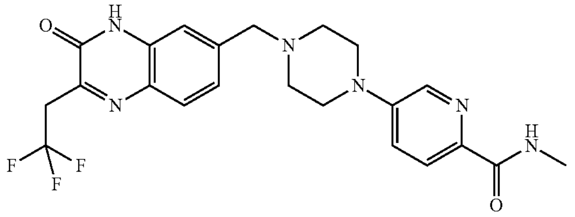 [SMILES: CNC(=O)c1ccc(N2CCN(Cc3ccc4nc(CC(F)(F)F)c(=O)[nH]c4c3)CC2)cn1]

7-(hydroxymethyl)-3-(2,2,2-trifluoroethyl)quinoxalin-2(1H)-one (Intermediate 89, 50 mg, 0.19 mmol) was added to 33% HBr in AcOH (2 mL, 12.15 mmol). The resulting mixture was stirred at 80° C. for 2 hours. The reaction mixture was evaporated under vacuum to afford 7-(bromomethyl)-3-(2,2,2-trifluoroethyl)quinoxalin-2(1H)-one (crude product). The product was used in the next step directly without further purification. DIPEA (0.169 mL, 0.97 mmol) was added to 7-(bromomethyl)-3-(2,2,2-trifluoroethyl)quinoxalin-2(1H)-one (crude product) and N-methyl-5-(piperazin-1-yl)picolinamide (Intermediate 13, 50 mg, 0.23 mmol) in NMP (2 mL) . The resulting mixture was stirred at 80° C. for 1 hour. The reaction mixture was concentrated purified by preparative HPLC (Column: Sunfire prep C18 column, 30×150, 5 um; Mobile Phase A: Water (0.1% $HCO_2H$), Mobile Phase B: ACN; Flow rate: 60 mL/min; Gradient: 10 B to 25 B in 7 min; 254/220 nm; RT: 6.57. Fractions containing the desired compound were evaporated to dryness to afford N-methyl-5-[4-[[3-oxo-2-(2,2,2-trifluoroethyl)-4H-quinoxalin-6-yl]methyl]piperazin-1-yl]pyridine-2-carboxamide (Example 27, 41.5 mg, 46.6%) as an off-white solid. $^1H$ NMR (400 MHz, DMSO-$d_6$) δ 2.56 (4H, m), 2.78 (3H, d), 3.35 (4H, m), 3.65 (2H, s), 3.88 (2H, q), 7.29-7.42 (3H, m), 7.79 (2H, m), 8.25-8.30 (1H, m), 8.38 (1H, m),12.60 (1H, br s); $^{19}F$ NMR (376 MHz, DMSO-$d_6$) δ-61.53; m/z ($ES^+$) $[M+H]^+$=461.

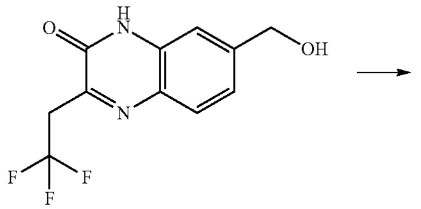

Intermediate 89

-continued

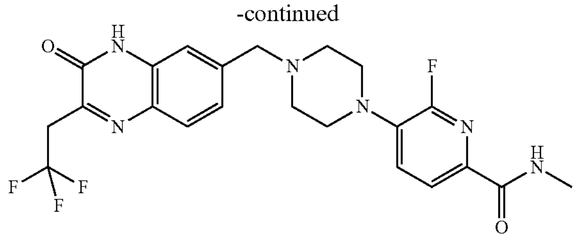

Example 28

Example 28: 6-fluoro-N-methyl-5-[4-[[3-oxo-2-(2,2,2-trifluoroethyl)-4H-quinoxalin-6-yl]methyl]piperazin-1-yl]pyridine-2-carboxamide

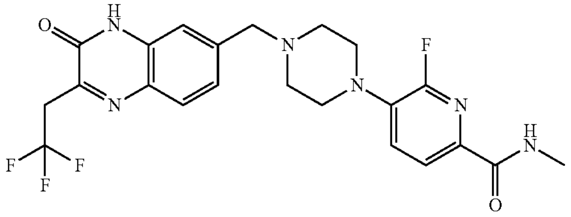 [SMILES: CNC(=O)c1ccc(N2CCN(Cc3ccc4nc(CC(F)(F)F)c(=O)[nH]c4c3)CC2)c(F)n1]

7-(hydroxymethyl)-3-(2,2,2-trifluoroethyl)quinoxalin-2(1H)-one (Intermediate 89, 60 mg, 0.23 mmol) was added to 33% HBr in AcOH (2 mL, 12.15 mmol). The resulting mixture was stirred at 80° C. for 2 hours. The reaction mixture was evaporated under vacuum to afford 7-(bromomethyl)-3-(2,2,2-trifluoroethyl)quinoxalin-2(1H)-one (crude product). The product was used in the next step directly without further purification. DIPEA (0.203 mL, 1.16 mmol) was added to 7-(bromomethyl)-3-(2,2,2-trifluoroethyl)quinoxalin-2(1H)-one (crude product) and 6-fluoro-N-methyl-5-(piperazin-1-yl)picolinamide (Intermediate 23, 60 mg, 0.25 mmol) in NMP (2 mL) . The resulting mixture was stirred at 80° C. for 2 hours. The resulting mixture was purified by preparative HPLC (Column: Sunfire prep C18 column, 30×150, 5 um; Mobile Phase A: Water (0.1% $HCO_2H$), Mobile Phase B: ACN; Flow rate: 60 mL/min; Gradient: 12 B to 30 B in 7 min; 254/220 nm; RT: 6.25. Fractions containing the desired compound were evaporated to dryness to afford 6-fluoro-N-methyl-5-[4-[[3-oxo-2-(2,2,2-trifluoroethyl)-4H-quinoxalin-6-yl]methyl]piperazin-1-yl]pyridine-2-carboxamide (Example 28, 49.0 mg, 43.3%) as an off-white solid. $^1$H NMR (400 MHz, DMSO-$d_6$) δ 2.53-2.63 (4H, m), 2.76 (3H, d), 3.15-3.22 (4H, m), 3.65 (2H, s), 3.88 (2H, q), 7.28-7.35 (2H, m), 7.57 (1H, dd), 7.76 (1H, d), 7.84 (1H, dd), 8.17 (0.185H, s), 8.38 (1H, m), 12.57 (1H, s); $^{19}$F NMR (376 MHz, DMSO-$d_6$) δ-61.54,-72.52; m/z ($ES^+$) $[M+H]^+$=479.

Example 29: 6-(difluoromethyl)-5-[4-[(7-ethyl-6-oxo-5H-1,5-naphthyridin-3-yl)methyl]piperazin-1-yl]-N-methyl-pyridine-2-carboxamide

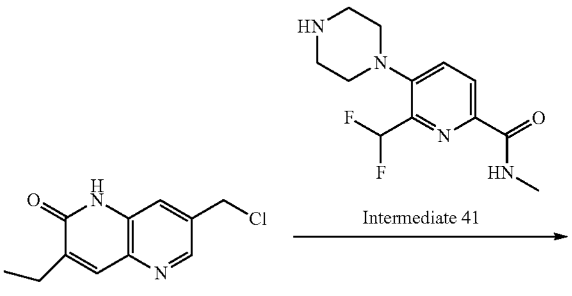

Intermediate 41

Intermediate 17

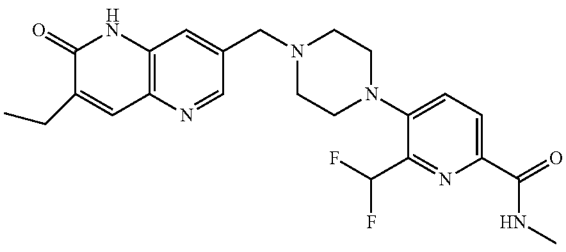

Example 29

DIPEA (330 μl, 1.89 mmol) was added to a stirred solution of 7-(chloromethyl)-3-ethyl-1,5-naphthyridin-2(1H)-one, HCl (Intermediate 17, 70 mg, 0.27 mmol), sodium iodide (4.05 mg, 0.03 mmol) and 6-(difluoromethyl)-N-methyl-5-piperazin-1-yl-pyridine-2-carboxamide, 2 HCl (Intermediate 41, 102 mg, 0.30 mmol) in acetonitrile (2.4 mL) at 20° C. and the resulting solution was stirred at 50° C. for 3 hours. Solvent was removed under vacuum and 50 mL water followed by 3 mL sat $NaHCO_3$ was added. Mixture was extracted with ethyl acetate. After concentration, the resulting residue was purified by flash silica chromatography, elution gradient 0 to 30% MeOH in DCM. Product fractions were concentrated under reduced pressure to dryness to afford 6-(difluoromethyl)-5-[4-[(7-ethyl-6-oxo-5H-1,5-naphthyridin-3-yl)methyl]piperazin-1-yl]-N-methyl-pyridine-2-carboxamide (Example 29, 52.0 mg, 42%) as a pale yellow solid. $^1$H NMR (500 MHz, DMSO-$d_6$) 1.19 (3H, t), 2.54-2.58 (2H, m), 2.63 (4H, br s), 2.84 (3H, d), 3.03 (4H, br t), 3.68 (2H, s), 7.14 (1H, t), 7.62 (1H, d), 7.76 (1H, s), 7.86 (1H, d), 8.10 (1H, d), 8.32-8.45 (2H, m), 11.86 (1H, s); m/z ($ES^+$) $[M+H]^+$=457.

Example 30: 5-[4-[(7-ethyl-6-oxo-5H-1,5-naphthyridin-3-yl)methyl]piperazin-1-yl]-N-methyl-6 (trifluoromethyl)pyridine-2-carboxamide

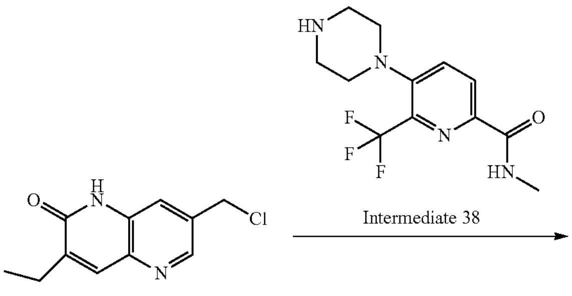

Intermediate 17

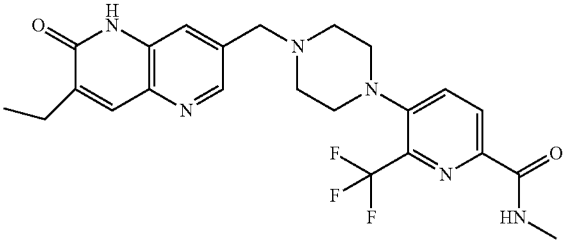

Example 30

DIPEA (330 μl, 1.89 mmol) was added to a stirred solution of 7-(chloromethyl)-3-ethyl-1,5-naphthyridin-2 (1H)-one, HCl (Intermediate 17, 70 mg, 0.27 mmol), sodium iodide (4.05 mg, 0.03 mmol) and N-methyl-5-piperazin-1-yl-6-(trifluoromethyl)pyridine-2-carboxamide, 2 HCl (Intermediate 38,107 mg, 0.30 mmol) in acetonitrile (2.4 mL) at 20° C. and the resulting solution was stirred at 50° C. for 3 hours. Solvent was removed under vacuum and 50 mL water followed by 3 mL sat $NaHCO_3$ was added. Mixture was extracted with ethyl acetate. After concentration, the resulting residue was purified by flash silica chromatography, elution gradient 0 to 30% MeOH in DCM. Product fractions were concentrated under reduced pressure to dryness to afford 5-[4-[(7-ethyl-6-oxo-5H-1,5-naphthyridin-3-yl) methyl]piperazin-1-yl]-N-methyl-6 (trifluoromethyl)pyridine-2-carboxamide (Example 30, 58.0 mg, 45%) as a pale yellow solid. $^1H$ NMR (500 MHz, DMSO-$d_6$) 1.19 (3H, t), 2.54-2.62 (6H, m), 2.83 (3H, d), 3.04 (4H, br t), 3.67 (2H, s), 7.62 (1H, d), 7.75 (1H, s), 8.04 (1H, d), 8.19 (1H, d), 8.31-8.48 (2H, m), 11.85 (1H, s); m/z ($ES^+$) $[M+H]^+$=475.

Example 31: 5-[4-[(7-ethyl-6-oxo-5H-1,5-naphthyridin-3-yl)methyl]piperazin-1-yl]-N,6-dimethyl-pyridine-2-carboxamide

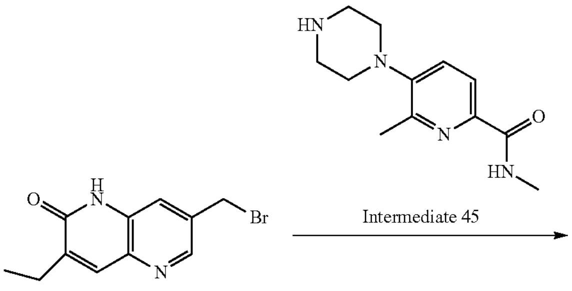

Intermediate 14

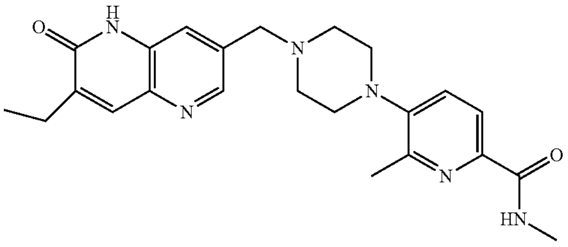

Example 31

DIPEA (0.366 mL, 2.10 mmol) was added to a stirred solution of 7-(bromomethyl)-3-ethyl-1,5-naphthyridin-2 (1H)-one (Intermediate 14, 80 mg, 0.30 mmol) and N,6-dimethyl-5-piperazin-1-yl-pyridine-2-carboxamide, 2 HCl (Intermediate 45, 101 mg, 0.33 mmol) in acetonitrile (2 mL) at 20° C. and the resulting solution was stirred at 70° C. for 3 hours. Solvent was removed under vaccum and 50 mL water followed by 3 mL sat $NaHCO_3$ was added. Mixture was extracted with ethyl acetate. After concentration, the resulting residue was purified by flash silica chromatography, elution gradient 0 to 30% MeOH in DCM. Product fractions were concentrated under reduced pressure to dryness to afford 5-[4-[(7-ethyl-6-oxo-5H-1,5-naphthyridin-3-yl)methyl]piperazin-1-yl]-N,6-dimethyl-pyridine-2-carboxamide (Example 31, 36.0 mg, 29%) as a pale yellow solid. $^1H$ NMR (500 MHz, DMSO-$d_6$) 1.19 (3H, t), 2.50 (3H, s), 2.54-2.57 (2H, m), 2.57-2.64 (4H, m), 2.81 (3H, d), 2.96 (4H, br s), 3.68 (2H, s), 7.49 (1H, d), 7.63 (1H, d), 7.76 (1H, s), 7.80 (1H, d), 8.35-8.47 (2H, m), 11.85 (1H, br s); m/z ($ES^+$) $[M+H]^+$=421.

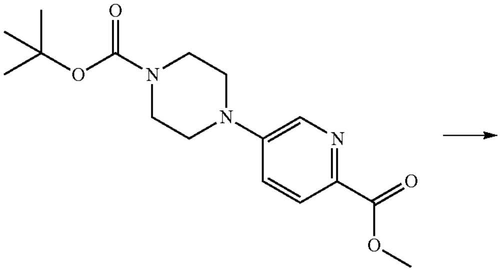

Intermediate 15

-continued

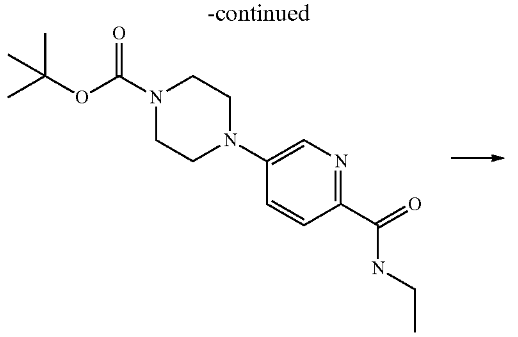

Intermediate 90

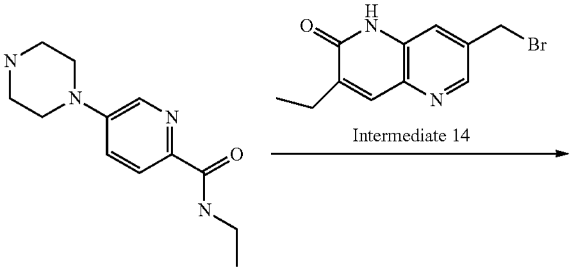

Intermediate 14

Intermediate 91

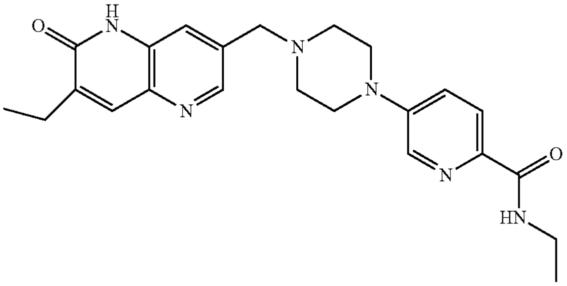

Example 32

Intermediate 90: Tert-butyl 4-[6-(ethylcarbamov1)-3-pyridyl]piperazine-1-carboxylate Ethanamine in methanol (7 M, 7.78 mL, 15.56 mmol) was added to solution of tert-butyl 4-(6-(methoxycarbonyl)pyridin-3-yl)piperazine-1-carboxylate (Intermediate 15, 500 mg, 1.56 mmol) and the resulting solution was stirred at 50° C. for 18 hours. Solvent was removed under vacuum and sample was dried further to afford tert-butyl 4-[6-(ethylcarbamoyl)-3-pyridyl]piperazine-1-carboxylate (Intermediate 90, 0.495 g, 95%). $^1$H NMR (500 MHz, DMSO-d6) 1.11 (3H, t), 1.43 (9H, s), 3.27-3.32 (6H, m), 3.44-3.52 (4H, m), 7.42 (1H, dd), 7.85 (1H, d), 8.28 (1H, d), 8.44 (1H, br t).

Intermediate 91: N-ethyl-5-piperazin-1-yl-pyridine-2-carboxamide

HCl in dioxane (0.473 mL, 15.58 mmol) was added slowly to a stirred solution of tert-butyl 4-(6-(ethylcarbamoyl)pyridin-3-yl)piperazine-1-carboxylate (Intermediate 90, 521 mg, 1.56 mmol), in methanol (10 mL). The resulting solution was stirred at rt for 17 hours. Reaction was concentrated and the solid was dried to give N-ethyl-5-piperazin-1-yl-pyridine-2-carboxamide, 2 HCl (Intermediate 91, 421 mg, 88%); m/z (ES$^+$) [M+H]$^+$=235

Example 32: N-ethyl-5-[4-[(7-ethyl-6-oxo-5H-1,5-naphthyridin-3-yl)methyl]piperazin-1-yl]pyridine-2-carboxamide

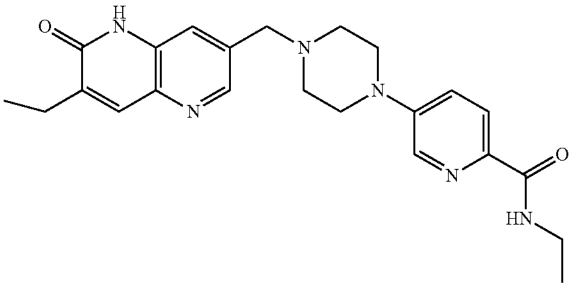 [SMILES: CCNC(=O)c1ccc(N2CCN(Cc3cnc4cc(CC)c(=O)[nH]c4c3)CC2)cn1]

DIPEA (0.320 mL, 1.83 mmol) was added to a stirred solution of 7-(bromomethyl)-3-ethyl-1,5-naphthyridin-2(1H)-one (Intermediate 14, 70 mg, 0.26 mmol), and N-ethyl-5-piperazin-1-yl-pyridine-2-carboxamide, 2 HCl (Intermediate 91, 89 mg, 0.29 mmol) in acetonitrile (2 mL) at 20° C. and the resulting solution was stirred at 70° C. for 3 hours. Solvent was removed under vaccum and 50 mL water followed by 3 mL sat $NaHCO_3$ was added. Mixture was extracted with ethyl acetate. After concentration, the crude product was purified by reverse phase chromatography (column: XbridC18), elution gradient 20 to 50% MeCN in water (with 0.2% NH4OH). Pure fractions were evaporated to dryness to afford N-ethyl-5-[4-[(7-ethyl-6-oxo-5H-1,5-naphthyridin-3-yl)methyl]piperazin-1-yl]pyridine-2-carboxamide (Example 32, 28.0 mg, 25%) as white solid. $^1$H NMR (500 MHz, DMSO-d$_6$) 1.10 (3H, t), 1.19 (3H, t), 2.52-2.55 (2H, m), 2.55-2.59 (4H, m), 3.26-3.30 (2H, m), 3.34 (4H, br d), 3.66 (2H, s), 7.40 (1H, dd), 7.63 (1H, s), 7.76 (1H, s), 7.83 (1H, d), 8.27 (1H, d), 8.36-8.46 (2H, m), 11.74-11.94 (1H, m); m/z (ES$^+$) [M]$^+$=420.

Example 4—Form A

In Example 4, 5-[4-[(7-ethyl-6-oxo-5H-1,5-naphthyridin-3-yl)methyl]piperazin-1-yl]-N-methyl-pyridine-2-carboxamide was obtained as a partially crystalline solid by evaporating a methanol/dichloromethane solution under reduced pressure. The crystalline material so-obtained was characterised as crystalline Form A.

In the case of poor crystallinity, crystalline Form A was obtainable by suspending 20 mg of the crude sample in 0.20 ml of water, methanol, ethanol, acetone, acetonitrile, tetrahydrofuran, ethyl acetate or other solvent for 1 day at the ambient temperature or 50° C.

Form A was analysed by XRPD and the results are tabulated below (Table 1) and shown in FIG. 1.

TABLE 1

XRPD Peaks for Form A

| Angle (2θ ± 0.2°) | Intensity (%) |
|---|---|
| 8.3 | 100.0 |
| 12.4 | 30.9 |
| 19.4 | 26.5 |
| 20.4 | 25.8 |
| 26.3 | 19.2 |
| 21.2 | 17.4 |
| 20.8 | 14.8 |

TABLE 1-continued

| XRPD Peaks for Form A | |
|---|---|
| Angle (2θ ± 0.2°) | Intensity (%) |
| 22.8 | 14.1 |
| 16.8 | 14.0 |
| 10.2 | 13.2 |
| 18.4 | 10.8 |
| 11.4 | 9.9 |
| 28.1 | 8.4 |
| 18.0 | 8.4 |
| 25.2 | 8.2 |
| 24.9 | 6.7 |
| 16.5 | 6.4 |
| 17.3 | 5.3 |
| 22.1 | 4.0 |
| 29.3 | 3.3 |
| 24.3 | 2.7 |
| 30.3 | 2.5 |
| 38.2 | 2.0 |
| 33.9 | 1.4 |
| 14.2 | 1.4 |
| 13.7 | 1.4 |
| 33.0 | 1.3 |
| 36.5 | 1.2 |
| 39.2 | 1.2 |

Form A is characterized in providing at least one of the following 2θ values measured using CuKα radiation: 8.3, 12.4, and 19.4° .

Form A was analyzed by thermal techniques. DSC analysis indicated that Form A has a melting point with an onset at 254° C. and a peak at 255° C. A representative DSC trace of Form A is shown in FIG. 2.

Biological Assays

The following test procedures may be employed to determine the inhibitory properties of the compounds described herein.

PARP Fluorescence Anisotropy binding assays

Recombinant full length 6HIS tagged PARP1 protein was diluted to 6 nM with 50 mM Tris pH 8, 0.001% Triton X100, 10 mM $MgCl_2$, 150 mM NaCl and incubated for four hours with an equivalent volume of 2 nM fluorescent probe diluted with 50 mM Tris pH 8, 0.001% Triton X100, 10 mM $MgCl_2$, 150 mM NaCl. The final DMSO concentration of the probe was kept below 1% (v/v).

Recombinant full length PARP2 protein was diluted to 6 nM with 50 mM Tris pH 8, 0.001% Triton X100, 10 mM $MgCl_2$, 150 mM NaCl and incubated for four hours with an equivalent volume of 2 nM fluorescent probe diluted with 50 mM Tris pH 8, 0.001% Triton X100, 10 mM $MgCl_2$, 150 mM NaCl. The final DMSO concentration of the probe was kept below 1% (v/v).

Recombinant full length PARP3 protein was diluted to 100 nM with 50 mM Tris pH 8, 0.001% Triton X100, 10 mM $MgCl_2$, 150 mM NaCl and incubated for four hours with an equivalent volume of 6 nM fluorescent probe diluted with 50 mM Tris pH 8, 0.001% Triton X100, 10 mM $MgCl_2$, 150 mM NaCl. The final DMSO concentration of the probe was kept below 1% (v/v).

Recombinant PARP5a binding domain was diluted to 160 nM with 50 mM Tris pH 8, 0.001% Triton X100, 10 mM MgCl2, 150 mM NaCl and incubated for four hours with an equivalent volume of 6 nM fluorescent probe diluted with 50 mM Tris pH 8, 0.001% Triton X100, 10 mM $MgCl_2$, 150 mM NaCl. The final DMSO concentration of the probe was kept below 1% (v/v).

Recombinant full length GST tagged PARP6 protein was diluted to 160 nM with 50 mM Tris pH 8, 0.001% Triton X100, 10 mM $MgCl_2$, 150 mM NaCl and incubated for four hours with an equivalent volume of 6 nM fluorescent probe diluted with 50 mM Tris pH 8, 0.001% Triton X100, 10 mM $MgCl_2$, 150 mM NaCl. The final DMSO concentration of the probe was kept below 1% (v/v).

Fluorescence anisotropy of the probe when bound to the proteins was measured using a BMG Pherastar FS® in the presence of test compounds or solvent control and the effect on anisotropy determined. % inhibition values for different test compound concentrations were calculated and fitted to a four parameter logistic plot in order to determine the $IC_{50}$ value. Where necessary, the compound K can be determined from the $IC_{50}$ value using a Munson Rodbard equation defined in *Anal Biochem.* 1980 Sep 1;107(1):220-39 and is based on the known $K_D$ of the probe binding to the relevant PAR P protein hERG Electrophysiological Assay

Electrophysiological recordings (all performed at RT) from stably transfected CHO hKv11.1 cells were obtained using the Nanion Syncropatch 768PE. Test compounds, vehicle or positive controls were added with 6 compound plates each at a different concentration to allow cumulative dosing onto cells (10 mM, 3.167 mM, 1 mM, 0.3167 mM, 0.1 mM, 0.03167 mM). 600 ⍰l of compound is resuspended into 90 µl of reference buffer (in mM, NaCl 80, KCL 4, CaCl 5, MgCl 1, NMDG Cl 60, D-Glucose monohydrate 5, HEPES 10 (pH7.4 HCL, 298 mOsm) for a final compound concentration of 39.6 µM, 13.2 µM, 4.4 µM, 1.46 µM, 0.48 µM, 0.16 µM. For each Nanion Syncropatch 768PE run, the current amplitude in each cell in the presence of extracellular solution (in mM, NaCl 80, KCL 4, CaCl 5, MgCl 1, NMDG Cl 60, D-Glucose monohydrate 5, HEPES 10 (pH 7.4 HCL, 298 mOsm) is measured with all liquid additions performed using the Syncropatch liquid handling system. Add 40 µL external solution (in mM, HBPS, CaCl2 2, MgCl2 1 (pH7.4, NaOH) to 384 well multihole medium resistance recording chip and perfuse internal buffer (in mM, KF 130, KCl 20, MgCl2 1, EGTA 10 , HEPES 10, Escin 25 (all Sigma-Aldrich; pH 7.2-7.30 using10 M KOH, 320 mOsm) to the underside of plate. Dispense 20 µL of cells at a density of 1 e6 cells/ml maintained at ~9° C. into each well of the chip followed by 20 µL of seal enhancer (in mM, NaCl 80, KCl 3, CaCl 10, HEPES 10, MgCl 1 (pH7.4 NaOH). Perform wash step leaving a residual volume of 40 µL. Dispense 40 µL of reference buffer to establish a stable baseline prior to the addition of test compounds, with a removal step of 40 µL after 3 min, repeat this step. Dispense 40 µL of compound concentration 1 (0.16 µM), 'real time' recordings for 3 min exposure prior to removal of 40 µL. This step is repeated for 5 further subsequent compound plates to generate cumulative curve analysis. All data is leak subtracted, 2 pulses to −80 mV 100 ms with 100 ms delay. Outward K+ currents are then evoked by a voltage step to +60 mV from a holding potential of −90 mV, Each pulse is delivered at a frequency of 2 Hz with a 15 s pulse interval.

PARP Proliferation Assay (4 day compound dosing)

DLD1 and BRCA2 (−/−) DLD1 cells were harvested to a density of 1.875E4 cells/ml and 6.25E4 cells/ml respectively in complete media, 40 µL/well seeded into 384-well plates (Greiner, Kremsmunster, Austria; 781090) using a Multidrop Combi then incubated at 37° C., 5% $CO_2$ overnight. Next day (Day 1) using a Multidrop Combi add sytox green (5ul, 2 uM) and saponin (10 ul, 0.25% stock) to a day 0 plate, seal the plate using a black adhesive lid and incubate for >3 hrs at RT. Cells were imaged using Cell Insight (Thermo Fisher) fitted with a 4× objective. Test compounds are added using an Echo 555 and placed in incubator maintained at 37° C., 5% $CO_2$ and incubated for 4 days. On Day 5 add sytox green (5 ul, 2 uM) and then saponin (10 ul, 0.25% stock) to plates, seal the plate using a black adhesive lid and incubate for >3 hrs at RT. Read all cells on the Cell Insight with 4× Objective. The rate of proliferation is determined in Genedata by assessing the total cell number output from the Cell Insight for Day 0 and Day 5 plates

TABLE 2

| Example No. | PARP1 IC50 (μM) | PARP2 IC50 (μM) | PARP3 IC50 (μM) | PARP5a IC50 (μM) | PARP6 IC50 (μM) | BRCA2 −/− DLD-1 prolif 4 d IC50 (μM) | WT DLD-1 prolif 4 d IC50 (μM) | hERG IC50 (μM) |
|---|---|---|---|---|---|---|---|---|
| 1 | 0.003 | 1.7 | 4 | >100 | 34 | 0.010 | >30 | >40 |
| 2 | 0.004 | 0.88 | 9.9 | 20 | 14 | 0.008 | >30 | >40 |
| 3 | 0.005 | 1.3 | 12 | >100 | 14 | 0.004 | >30 | 22 |
| 4 | 0.004 | >1.5 | 4.7 | >100 | 19 | >0.017 | >30 | >40 |
| 5 | 0.002 | 0.65 | 7.1 | >100 | 23 | 0.006 | >30 | >40 |
| 6 | 0.003 | 0.84 | 9.3 | >100 | 8.2 | 0.006 | >30 | >40 |
| 7 | 0.002 | 1.3 | 2.6 | 94 | 22 | 4.14 | | |
| 8 | 0.003 | 11 | 55 | 93 | 18 | 0.011 | >19 | >40 |
| 9 | 0.009 | 22 | >100 | >100 | 47 | 0.010 | 17 | >40 |
| 10 | 0.005 | 17 | 48 | 56 | 26 | 0.006 | >30 | >40 |
| 11 | 0.005 | 4 | 13 | >100 | 22 | 0.184 | >30 | >40 |
| 12 | 0.004 | 1.6 | 19 | 89 | 11 | 0.008 | >30 | >40 |
| 13 | 0.007 | 8.5 | 30 | >100 | 30 | 0.005 | >26 | >40 |
| 14 | 0.004 | 2.9 | 30 | 50 | 11 | 0.006 | >30 | >40 |
| 15 | 0.011 | 3.6 | 35 | >100 | 80 | 0.090 | >30 | >40 |
| 16 | 0.007 | 3.3 | 74 | 61 | 31 | 0.018 | >22 | >40 |
| 17 | 0.007 | 1.7 | 96 | >100 | 59 | 0.020 | >30 | >40 |
| 18 | 0.031 | 17 | >100 | >100 | >29 | 4.90 | >30 | 5.2 |
| 19 | 0.015 | >100 | >100 | >100 | >29 | 0.015 | >30 | 21 |
| 20 | 0.014 | 28 | >100 | >100 | >100 | 0.016 | >24 | 38 |
| 21 | 0.004 | 9.5 | >100 | >100 | 33 | 0.016 | >30 | >40 |
| 22 | 0.006 | 1 | 2.6 | 26 | 16 | 0.012 | >30 | >40 |
| 23 | 0.004 | 4.4 | 60 | 60 | >100 | | 4.2 | 36 |
| 24 | 0.003 | 5.1 | >100 | 93 | >100 | 0.010 | 14 | 37 |
| 25 | 0.002 | 6 | 43 | >100 | >100 | | >25 | >40 |
| 26 | 0.005 | 6.7 | >100 | >100 | >100 | 0.005 | 23 | >40 |
| 27 | 0.007 | 16 | >100 | 71 | >100 | 10.3 | >10 | 26 |
| 28 | 0.006 | 14 | >100 | >29 | >100 | 0.027 | >30 | >40 |
| 29 | 0.004 | 6.1 | 9.9 | >100 | 14 | 0.007 | >30 | >40 |
| 31 | 0.003 | 7.6 | 4.5 | >100 | 10 | 0.004 | >30 | >40 |
| 32 | 0.005 | 3.7 | 2.6 | >100 | 28 | | | >40 |
| 33 | 0.003 | 2.1 | 1.9 | >100 | 10 | | | >40 |

The invention claimed is:

1. A compound of formula (Ia)

(Ia)

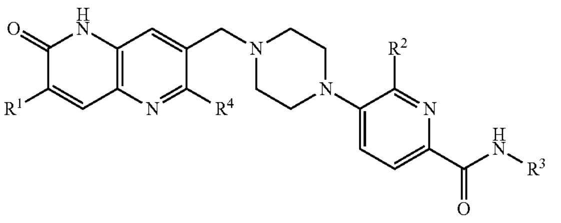

wherein $R^1$ is $C_{1-4}$ alkyl, $R^2$ is selected from H, halo, $C_{1-4}$ alkyl, and $C_{1-4}$ fluoroalkyl $R^3$ is H or $C_{1-4}$ alkyl, and $R^4$ is H, or a pharmaceutically acceptable salt thereof.

2. A compound according to claim 1 wherein $R^2$ is selected from difluoromethyl, trifluoromethyl, and methyl, or a pharmaceutically acceptable salt thereof.

3. A compound according to claim 1 wherein $R^2$ is H or halo, or a pharmaceutically acceptable salt thereof.

4. A compound according to claim 1 wherein $R^1$ is ethyl, $R^2$ is selected from H, chloro and fluoro, and $R^3$ is methyl, or a pharmaceutically acceptable salt thereof.

5. A compound according to claim 1 selected from:

5-[4-[(7-ethyl-6-oxo-5H-1,5-naphthyridin-3-yl)methyl]piperazin-1-yl]-N-methyl-pyridine-2-carboxamide, 5-[4-[(7-ethyl-6-oxo-5H-1,5-naphthyridin-3-yl)methyl]piperazin-1-yl]-6-fluoro-N-methyl-pyridine-2-carboxamide, 6-chloro-5-[4-[(7-ethyl-6-oxo-5H-1,5-naphthyridin-3-yl)methyl]piperazin-1-yl]-N-methyl-pyridine-2-carboxamide, 5-[4-[(7-ethyl-6-oxo-5H-1,5-naphthyridin-3-yl)methyl]piperazin-1-yl]pyridine-2-carboxamide, or a pharmacutically acceptable salt thereof.

6. A compound according to claim 1 which is selected from:

6-(difluoromethyl)-5-[4-[(7-ethyl-6-oxo-5H-1,5-naphthyridin-3-yl)methyl]piperazin-1-yl]-N-methyl-pyridine-2-carboxamide, 5-[4-[(7-ethyl-6-oxo-5H-1,5-naphthyridin-3-yl)methyl]piperazin-1-yl]-N-methyl-6 (trifluoromethyl)pyridine-2-carboxamide, 5-[4-[(7-ethyl-6-oxo-5H-1,5-naphthyridin-3-yl)methyl]piperazin-1-yl]-N,6-dimethyl-pyridine-2-carboxamide, N-ethyl-5-[4-[(7-ethyl-6-oxo-5H-1,5-naphthyridin-3-yl)methyl]piperazin-1-yl]pyridine-2-carboxamide, or a pharmaceutically acceptable salt thereof.

7. A pharmaceutical composition comprising a compound or a pharmaceutically acceptable salt thereof according to any of claim 1, and at least one pharmaceutically acceptable diluent, excipient or inert carrier.

* * * * *